US009878036B2

(12) United States Patent
Coulter et al.

(10) Patent No.: US 9,878,036 B2
(45) Date of Patent: Jan. 30, 2018

(54) IMMUNOMODULATORY COMPOSITIONS COMPRISING A POLYMER MATRIX AND AN OIL PHASE

(75) Inventors: Ivan Coulter, Dublin (IE); Bernard Francis McDonald, Dublin (IE); Vincenzo Aversa, Dubin (IE); Monica Torres Rosa, Dublin (IE); Edward Charles Lavelle, Dublin (IE)

(73) Assignee: Sigmoid Pharma Limited, Dublin (IE)

( * ) Notice: Subject to any disclaimer, the term of this patent is extended or adjusted under 35 U.S.C. 154(b) by 153 days.

(21) Appl. No.: 13/390,085

(22) PCT Filed: Aug. 12, 2010

(86) PCT No.: PCT/EP2010/061791
§ 371 (c)(1),
(2), (4) Date: Feb. 10, 2012

(87) PCT Pub. No.: WO2011/018504
PCT Pub. Date: Feb. 17, 2011

(65) Prior Publication Data
US 2012/0141585 A1    Jun. 7, 2012

Related U.S. Application Data

(60) Provisional application No. 61/233,170, filed on Aug. 12, 2009.

(30) Foreign Application Priority Data

Aug. 12, 2009  (IE) ..................................... 2009/0618

(51) Int. Cl.
| A61K 39/395 | (2006.01) |
| A61K 39/39 | (2006.01) |
| A61K 9/16 | (2006.01) |
| A61K 9/50 | (2006.01) |
| A61K 9/107 | (2006.01) |
| A61K 39/00 | (2006.01) |

(52) U.S. Cl.
CPC ............ *A61K 39/39* (2013.01); *A61K 9/1617* (2013.01); *A61K 9/1652* (2013.01); *A61K 9/1658* (2013.01); *A61K 9/5026* (2013.01); *A61K 9/107* (2013.01); *A61K 9/1075* (2013.01); *A61K 2039/542* (2013.01); *A61K 2039/55561* (2013.01); *A61K 2039/55566* (2013.01)

(58) Field of Classification Search
None
See application file for complete search history.

(56) References Cited

U.S. PATENT DOCUMENTS

| 3,971,852 A | 7/1976 | Brenner et al. |
| 4,279,632 A | 7/1981 | Frosch et al. |
| 4,379,454 A | 4/1983 | Campbell et al. |
| 4,422,985 A | 12/1983 | Morishita et al. |
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamás et al. |
| 4,749,574 A | 6/1988 | Ueda et al. |
| 4,751,241 A | 6/1988 | Motoyama et al. |
| 4,857,335 A | 8/1989 | Bohm |
| 5,102,668 A | 4/1992 | Eichel et al. |
| 5,145,684 A | 9/1992 | Liversidge et al. |
| 5,330,835 A | 7/1994 | Kikuchi et al. |
| 5,342,625 A | 8/1994 | Hauer et al. |
| 5,362,564 A | 11/1994 | Suzuki et al. |
| 5,385,737 A | 1/1995 | Shigeno et al. |
| 5,401,502 A | 3/1995 | Wunderlich et al. |
| 5,411,952 A | 5/1995 | Kaswan |
| 5,418,010 A | 5/1995 | Janda et al. |
| 5,478,508 A | 12/1995 | Suzuki et al. |
| 5,480,655 A | 1/1996 | Jizomoto et al. |
| 5,492,701 A | 2/1996 | Cervos et al. |

(Continued)

FOREIGN PATENT DOCUMENTS

| AU | 31116/77 | 12/1976 |
| AU | 627220 B2 | 8/1992 |

(Continued)

OTHER PUBLICATIONS

Al-Meshal et al., "Oral administration of liposomes containing cyclosporine: a pharmacokinetic study," *International Journal of Pharmaceutics* 168:163-168, 1998.
Anderberg et al., "Sodium Caprate Elicits Dilatations in Human Intestinal Tight Junctions and Enhances Drug Absorption by the Paracellular Route," *Pharmaceutical Research* 10(6):857-864, 1993.
Barnes et al., "Theophylline: New Perspectives for an Old Drug," *AM J Respir Crit Care Med* 167:813-818, 2003.
Borel et al., "Carotenoids in biological emulsions: solubility, surface-to-core distribution, and release from lipid droplets," *Journal of Lipid Research* 37:250-261, 1996.
Cannon, "Oral Solid Dosage Forms of Lipid-based Drug Delivery Systems," *AM Pharm Rev* 8(1):108-115, 2005.

(Continued)

*Primary Examiner* — Yunsoo Kim
(74) *Attorney, Agent, or Firm* — Klarquist Sparkman, LLP

(57) ABSTRACT

A pharmaceutical composition comprising a water-soluble polymer matrix in which are dispersed droplets of oil, the composition comprising at least one immunomodulator selected from an adjuvant, an antigen or a combination thereof. A method of manufacturing shaped compositions comprises mixing an aqueous solution of a water-soluble polymer with an oil-based liquid to form a water-in-oil emulsion, at least one of the aqueous solution and the oil-based liquid comprising an antigen or an adjuvant or a combination thereof, and then causing or allowing the resultant suspension to solidify into one or more beads or other shaped elements.

64 Claims, 6 Drawing Sheets

(56) References Cited

U.S. PATENT DOCUMENTS

| | | | |
|---|---|---|---|
| 5,498,439 A | 3/1996 | Bonner et al. |
| 5,500,224 A | 3/1996 | Vranckx et al. |
| 5,510,118 A | 4/1996 | Bosch et al. |
| 5,529,777 A | 6/1996 | Andrianov et al. |
| 5,529,783 A | 6/1996 | Burke et al. |
| 5,571,533 A | 11/1996 | Santus et al. |
| 5,589,455 A | 12/1996 | Woo et al. |
| 5,645,856 A | 7/1997 | Lacy et al. |
| 5,650,232 A | 7/1997 | Glenn et al. |
| 5,665,386 A | 9/1997 | Benet et al. |
| 5,674,495 A | 10/1997 | Bowersock et al. |
| 5,795,590 A | 8/1998 | Kiefer et al. |
| 5,827,531 A | 10/1998 | Morrison et al. |
| 5,843,347 A | 12/1998 | Nguyen et al. |
| 5,851,275 A | 12/1998 | Amidon et al. |
| 5,858,401 A | 1/1999 | Bhalani et al. |
| 5,871,774 A | 2/1999 | Lemelson |
| 5,882,680 A | 3/1999 | Suzuki et al. |
| 5,914,132 A | 6/1999 | Kelm et al. |
| 5,958,876 A | 9/1999 | Woo et al. |
| 5,961,970 A | 10/1999 | Lowell et al. |
| 6,022,562 A | 2/2000 | Autant et al. |
| 6,113,936 A | 9/2000 | Takebayashi et al. |
| 6,121,234 A | 9/2000 | Benet et al. |
| 6,146,663 A | 11/2000 | Bissery et al. |
| 6,174,466 B1 | 1/2001 | Kiefer et al. |
| 6,190,692 B1 | 2/2001 | Busetti et al. |
| 6,251,661 B1 | 6/2001 | Urabe et al. |
| 6,267,985 B1 | 7/2001 | Chen et al. |
| 6,284,271 B1 | 9/2001 | Lundberg et al. |
| 6,309,663 B1 | 10/2001 | Patel et al. |
| 6,361,298 B1 | 3/2002 | Kiefer et al. |
| 6,429,089 B1 | 8/2002 | Matsuki |
| 6,457,339 B2 | 10/2002 | Komura |
| 6,531,150 B1 | 3/2003 | Sunohara et al. |
| 6,585,997 B2 | 3/2003 | Moro et al. |
| 6,555,372 B1 | 4/2003 | Motoki |
| 6,569,463 B2 | 5/2003 | Patel et al. |
| 6,761,903 B2 | 7/2004 | Chen et al. |
| 6,923,988 B2 | 8/2005 | Patel et al. |
| 6,972,132 B1 | 12/2005 | Kudo et al. |
| 7,097,857 B2 * | 8/2006 | Tracy et al. ............... 424/489 |
| 7,267,813 B2 | 9/2007 | Watanabe et al. |
| 7,374,779 B2 | 5/2008 | Chen et al. |
| 2001/0003589 A1 | 6/2001 | Neuer et al. |
| 2001/0024658 A1 | 9/2001 | Chen et al. |
| 2002/0009457 A1 | 1/2002 | Bowersock et al. |
| 2002/0098242 A1 | 6/2002 | Darder |
| 2003/0045516 A1 | 3/2003 | Luly et al. |
| 2003/0078194 A1 | 4/2003 | Cho et al. |
| 2003/0104048 A1 | 6/2003 | Patel et al. |
| 2003/0124061 A1 | 7/2003 | Roberts |
| 2003/0180352 A1 | 9/2003 | Patel et al. |
| 2003/0193102 A1 | 10/2003 | Yan |
| 2003/0232076 A1 | 12/2003 | Makino et al. |
| 2003/0235595 A1 | 12/2003 | Chen et al. |
| 2004/0029855 A1 | 2/2004 | Klaveness et al. |
| 2004/0062802 A1 | 4/2004 | Hermelin |
| 2004/0126428 A1 | 7/2004 | Hughes et al. |
| 2004/0230183 A1 | 11/2004 | Breegi et al. |
| 2004/0258701 A1 | 12/2004 | Dominowski et al. |
| 2004/0258702 A1 | 12/2004 | Blonder et al. |
| 2005/0095288 A1 | 5/2005 | Honea |
| 2005/0249807 A1 | 11/2005 | Brown et al. |
| 2006/0018965 A1 | 1/2006 | Moodley et al. |
| 2006/0034937 A1 | 2/2006 | Patel |
| 2006/0135441 A1 | 6/2006 | Khodadoust et al. |
| 2006/0222701 A1 | 10/2006 | Kulkarni et al. |
| 2007/0292523 A1 | 12/2007 | Moodley et al. |
| 2008/0020018 A1 | 1/2008 | Moodley et al. |
| 2008/0107694 A1 | 5/2008 | Trogden et al. |
| 2008/0113031 A1 | 5/2008 | Moodley et al. |
| 2008/0124279 A1 | 5/2008 | Andremont et al. |
| 2008/0311201 A1 | 12/2008 | Der-Yang et al. |
| 2008/0317769 A1 * | 12/2008 | Kang et al. ............ 424/184.1 |
| 2008/0318912 A1 | 12/2008 | Fox et al. |
| 2010/0136105 A1 | 6/2010 | Chen et al. |
| 2010/0203120 A1 | 8/2010 | Coulter |
| 2010/0215737 A1 | 8/2010 | Coulter |
| 2010/0239665 A1 | 9/2010 | Coulter |
| 2010/0255087 A1 | 10/2010 | Coulter |
| 2010/0297221 A1 | 11/2010 | Coulter |
| 2011/0052645 A1 | 3/2011 | Coulter |
| 2012/0213854 A1 | 8/2012 | Fetzer |

FOREIGN PATENT DOCUMENTS

| | | |
|---|---|---|
| CA | 2170748 | 3/1995 |
| CA | 2376261 | 6/2000 |
| CN | 1557283 | 12/2004 |
| DE | 19848849 | 10/1998 |
| EP | 0396425 | 11/1990 |
| EP | 0525731 | 2/1993 |
| EP | 0550067 | 7/1993 |
| EP | 0621775 | 11/1994 |
| EP | 0650721 | 5/1995 |
| EP | 0760237 | 3/1997 |
| EP | 0778083 | 6/1997 |
| EP | 0922451 | 6/1999 |
| EP | 0813876 | 3/2002 |
| EP | 0789561 | 4/2004 |
| EP | 1811979 | 11/2008 |
| EP | 2105129 | 9/2009 |
| GB | 2257359 | 1/1993 |
| JP | 58013508 | 1/1983 |
| JP | 58077810 | 5/1983 |
| JP | 59-088420 | 5/1984 |
| JP | 61151119 | 7/1986 |
| JP | 64-000015 | 1/1989 |
| JP | H0549899 A | 3/1993 |
| JP | 7247215 A | 9/1995 |
| JP | 2000-247911 | 9/2000 |
| JP | 2000-302654 | 10/2000 |
| WO | WO 93/00063 | 1/1993 |
| WO | WO 94/15636 | 7/1994 |
| WO | WO 96/36322 | 11/1996 |
| WO | WO 97/02042 | 1/1997 |
| WO | WO 98/18610 | 5/1998 |
| WO | WO 98/50018 | 11/1998 |
| WO | WO 98/50033 | 11/1998 |
| WO | WO 99/06024 | 2/1999 |
| WO | WO 99/13914 | 3/1999 |
| WO | WO 00/00179 | 1/2000 |
| WO | WO 2000/33862 | 6/2000 |
| WO | WO 2000/69420 | 11/2000 |
| WO | WO 2001/008666 | 2/2001 |
| WO | WO 01/32142 | 5/2001 |
| WO | WO 2001/37808 | 5/2001 |
| WO | WO 2001/051008 | 7/2001 |
| WO | WO 02/064162 | 8/2002 |
| WO | WO 03/009812 | 2/2003 |
| WO | WO 2003/018134 | 3/2003 |
| WO | WO 2003/020243 | 3/2003 |
| WO | WO 03/030878 | 4/2003 |
| WO | WO 03/053404 | 7/2003 |
| WO | WO 03/056938 | 7/2003 |
| WO | WO 2003/092741 | 11/2003 |
| WO | WO 2004/022220 | 3/2004 |
| WO | WO 2004/042024 | 5/2004 |
| WO | WO 2004/052339 | 6/2004 |
| WO | WO 2004/064997 | 8/2004 |
| WO | WO 2004/084870 | 10/2004 |
| WO | WO 2005/020994 | 3/2005 |
| WO | WO 2005/030205 | 4/2005 |
| WO | WO 05/048998 | 6/2005 |
| WO | WO 2005/072088 | 8/2005 |
| WO | WO 2005/074913 | 8/2005 |
| WO | WO 2005/100454 | 10/2005 |
| WO | WO 2006/026592 | 3/2006 |
| WO | WO 2006/027685 | 3/2006 |
| WO | WO 2006/035416 | 4/2006 |
| WO | WO 2006/110802 | 10/2006 |
| WO | WO 2007/012478 | 2/2007 |
| WO | WO 2007/014445 | 2/2007 |

(56) References Cited

FOREIGN PATENT DOCUMENTS

| WO | WO 2007/018943 | 2/2007 |
|---|---|---|
| WO | WO 2009/014774 | 1/2009 |
| WO | WO 2009/060305 | 5/2009 |
| WO | WO 97/02017 | 9/2011 |

OTHER PUBLICATIONS

Chourasia et al., "Pharmaceutical approaches to colon targeted drug delivery systems," *J. Pharm. Pharmaceut. Sci.* 6(1):33-66-2003.

Chowdary et al., "Controlled Nifedipine Release from Microcapsules of its Dispersions in PVP-MCC and HPC-MCC," *Drug Development and Industrial Pharmacy* 21(10):1183-1192, 1995.

Drewe et al., "The absorption site of cyclosporine in the human gastro-intestinal tract," *Br. J. clin. Pharmac.* 33:39-43, 1992.

Gao et al., "Physiochemical characterization and evaluation of a microemulsion system for oral delivery of cyclosporin A," *International Journal of Pharmaceutics* 161:75-86, 1998.

Gursoy et al., "Self-emulsifying drug delivery systems (SEDDS) for improved oral delivery of lipophilic drugs," *Biomedicine & Pharmacotherapy* 58:173-182, 2004.

Ikegawa et al., Inhibition of P-glycoprotein by flavonoid derivatives in Adriamycin-resistant human myelogenous leukemia (K562/ADM)cells, *Cancer Letters* 177:89-93, 2002.

Kim et al., "Once-a-Day Oral Dosing Regimen of Cyclosporin A: Combined Therapy of Cyclosporin A Premicroemulsion Concentrates and Enteric Coated Solid-State Premicroemulsion Concentrates," *Pharmaceutical Research* 18(4):454-459, 2001.

Liu et al., "Gelatin-Stabilised Microemulsion-Based Organogels Facilitates Percutaneous Penetration of Cyclosporin A In Vitro and Dermal Pharmacokinetics In Vivo," *Journal of Pharmaceutical Sciences* 96(11):3000-3009, Nov. 2007.

Manakova et al., "Failure of FK506 (tacrolimus) to alleviate apomorphine-induced circling in rat Parkinson model in spite of some cytoprotective effects in SH-SY5Y dopaminergic cells," *Brain Research* 1038:83-91, 2005.

McGinity et al., Aqueous Polymeric Coatings for Pharmaceuticals Dosage Forms, *Marcel Dekker, Inc.*, 1997.

Miller et al., "Controlled Trial of Nimodipine in Amyotrophic Lateral Sclerosis," *Neuromusc. Disord.*, 6(2):101-104, 1996.

Ribeiro et al., "Microencapsulation of lipophilic drugs in chitosan-coated alginate microspheres," *International Journal of Pharmaceutics* 187:115-123, 1999.

Strowig et al., Comparison of Insulin Monotherapy and Combination Therapy with Insulin and Metformin or Insulin and Troglitazone in Type 2 Diabetes, *Diabetes Care* 25(10):1691-1698, 2002.

Sweetman and Martindale, "Nimodipine," *Cardiovascular Drugs* p. 946, 2002.

Yang et al., "Transport and uptake characteristics of a new derivative of berberine (CPU-86017) by human intestinal epithelial cell line: Caco-2," *Acta Pharmacol Sin* 24(12):1185-1191, 2003.

Yeh et al., "Effect of Medium-Chain Glycerides on Physiological Properties of Rabbit Intestinal Epithelium in Vitro," *Pharmaceutical Research* 11(8):1148-1154, 1994.

Zhang et al., "P-glycoprotein restricted transport of nimodipine across blood-brain barrier," *Acta Pharmacol Sin* 24(9):903-906, 2003.

Zuber et al., "Reversible cerebral angiopathy," *J. Neurol* 253:1585-1588, 2006.

International Search Report of PCT Application No. PCT/EP2010/061791 dated Apr. 13, 2011.

Final Office Action dated Jun. 17, 2011, from U.S. Appl. No. 11/663,834, filed Mar. 27, 2007.

Non-Final Office Action dated Jul. 15, 2011, from U.S. Appl. No. 11/236,549, filed Sep. 28, 2005.

Non-Final Office Action from U.S. Appl. No. 11/236,549 dated May 5, 2009.

Non-Final Office Action from U.S. Appl. No. 11/236,549 dated Oct. 6, 2010.

Final Office Action from U.S. Appl. No. 11/236,549 dated Apr. 1, 2011.

Non-Final Office Action from U.S. Appl. No. 11/663,834 dated Mar. 3, 2010.

Dhara et al., "Stability of Sodium Dodecyl Sulfate Micelles in the Presence of a Range of Water-Soluble Polymers: A Pressure-Jump Study," *J Phys. Chem. B.*, 105: 7133-7138; 2001.

Greener et al., "Interaction of Anionic Surfactants with Gelatin: Viscosity Effects," *Macromolecules*, 20: 2490-2498; 1987.

Holmberg et al., *Surfactants and Polymers in Aqueous Solution*. John Wiley & Sons, Ltd. 2002.

Muller et al. "Competitive Adssorption of Gelatin and Sodium. Dodecylbenzenesulfonate at Hydrophobic Surfaces," *Langmuir*, 14: 3107-3114; 1998.

Wesley et al., "Structure of Polymer/Surfactant Complexes Formed by Poly(2-(dimethylamino)ethyl metharylate) and Sodium Dodecyl Sulfate," *Langmuir* 18:5704-5707; 2002.

Non-Final Office Action dated Jun. 21, 2012, from corresponding U.S. Appl. No. 12/597,154.

McGinty et al. "Enteric Film Coating of Soft Gelatin Capsules" *Drug Development*, 3(6), 2008.

Newman et al. "Use of Nonioinic Block Copolymers in Vaccines and Therapeutics" *Critical Reviews in therapeutic Drug Carrier Systems*, 15(2): 89-142, 1998.

Westerink et al. "ProJuvant™ (Pluronic F127®/chitosan) enhances the immune response to intranasally administered tetanus toxoid" *Vaccine*, 20: 711-723, 2002.

Madene et al., "Flavour encapsulation and controlled release—a review," *International Journal of Food Science and Technology* 41:1-21, 2006.

Non-Final Office Action from co-pending U.S. Appl. No. 12/594,542 dated Oct. 5, 2012.

Final Office Action from co-pending U.S. Appl. No. 12/594,553 dated Sep. 10, 2012.

Non-Final Office Action from co-pending U.S. Appl. No. 13/321,149 dated Nov. 9, 2012.

Non-Final Office Action from co-pending U.S. Appl. No. 13/441,780 dated Nov. 28, 2012.

Milojevic et al., "Amylose as a coating for drug delivery to the colon: Preparation and in vitro evaluation using 5-aminosalicylic acid pellets," *Journal of Controlled Release* 38:75-84, 1996.

Murthy et al., "Treatment of Dextran Sulfate Sodium-Induced Murine Colitis by Intracolonic Cyclosporin," *Digestive Diseases and Sciences* 38(9):1722-1734, Sep. 1993.

Non-final Office action from U.S. Appl. No. 12/594,534, dated Mar. 30, 2012, 31pp.

Non-final Office action from U.S. Appl. No. 12/598,395, dated Mar. 26, 2012, 11pp.

Final Office action from U.S. Appl. No. 11/236,549, dated Mar. 15, 2012, 25pp.

Rodriguez et al., "Colonic budesonide delivery from ph-dependent microcapsules containing lipidic cores," *Acta Technologiae et Legis Medicamenti* 11(1):45-52, 2000.

Xu et al. "Structure Evolution of Gelatin Particles Induced by pH and Ionic Strength," *Microscopy Research and Technique*, 79:272-281, 2013.

Xu et al. "Effect of anionic surfactants on grafting density of gelatin modified with PDMS-E," *Colloids and Surfaces B: Biointerfaces*, 144:310-315, 2014.

Shioji, Yusaku "Manufacturing technology of solid formulation", CMC Publishing Co. Ltd., pp. 46-48 and 174-177, Jan. 27, 2003.

Office action issued for Japanese Patent Application No. 2006-507572.

Holmgren et al., "Mucosal immunity and vaccines," *Nature Medicine*, 11(4): 545-553, 2005.

Wakerly et al., "Pectin/Ethylcellulose Film Coating Formulations for Colonic Drug Delivery," Pharmaceutical Research, 13(8): 1210-1212, 1996.

(56) References Cited

OTHER PUBLICATIONS

Labarafil® M1944CS http://www.gattefosse.com/en/applications/labrafil-m1944cs.html, 2016.
Strickley, "Solubilizing Excipients in Oral and Injectable Formulations," *Pharmaceutical Research*, 21(2): 201-230, Feb. 2004.

* cited by examiner

IMMUNOMODULATORY COMPOSITIONS COMPRISING A POLYMER MATRIX AND AN OIL PHASE

CROSS REFERENCE TO RELATED APPLICATIONS

This is the U.S. National Stage of International Application No. PCT/EP2010/061791 filed Aug. 12, 2010, which was published in English under PCT Article 21(2), which in turn claims the benefit of U.S. Provisional Application No. 61/233,170, filed Aug. 12, 2009, and Ireland Patent Application No. IE 2009/0618, filed Aug. 12, 2009. The provisional application and Ireland patent application are incorporated herein in their entirety.

The present invention pertains to compositions for immune modulation, for example vaccination, and methods for preparing and delivering or administering such compositions in particular onto mucosal surfaces by, for example, oral administration, and to other subject matter.

BACKGROUND

Vaccination is mostly by injection. Injection requires complex and expensive logistics. For example, vaccinating large numbers of animals by injection, such as cattle, swine and poultry as well as fish, is either impossible or extremely labour intensive. It would be advantageous in terms of time and expense if the vaccine could be administered, simultaneously, with feed or water to a large number of animals, particularly as repeat doses must usually be given at intervals. Injectable vaccines also generally must be maintained (stored and shipped) at reduced temperature from factory to point of injection. This so-called "cold chain" is a further logistical complexity adding cost.

Apart from the risk of infection and cross-contamination arising from needle use, vaccination by injection is also uncomfortable or painful for the recipient person or animal and alternative administrative routes would be preferable.

Vaccines administered orally or nasally exist and transcutaneous vaccines are in development. However, for a variety of reasons, not all vaccines are available for administration orally, intranasally etc and it would be a significant step forward if more vaccines could be administered other than by injection.

Those oral vaccines that exist are generally live attenuated or killed whole cell preparations which rely on elements of the infectious agent stimulating an immune response through contact with the mucosa in the GI tract or beneath the dermis or other component of the mucosa-associated lymphoid tissue (MALT).

However, many modern vaccines include subunits of the infectious agent which may not by themselves have sufficient immunogenic power to elicit the desired immune response even when injected. Immunogenic power is increased by co-formulation of antigens with immunostimulants such as adjuvants, a phenomenon demonstrated above all for injectable vaccines.

Adjuvant systems to enhance an animal's immune response to a vaccine antigen are well known in the art. Likewise, systems for the delivery of vaccine and drugs to mucosal surfaces are known in the art. Various methods have been described to protect the vaccine antigen and drugs from degradation by stomach acid and digestive enzymes and to adsorb the antigen to the mucosal surface.

Yet mucosal delivery of vaccines has been underutilized because of remaining problems associated with effectively delivering vaccine components to mucosal surfaces and to the underlying mucosal lymphoid tissue, these problems being linked to the formulation complexities of combining various components to be released in active form at the appropriate site. Oral delivery of vaccines giving rise to a mucosal immune response remains a highly desirable goal given the fact that many pathogens invade via mucosal surfaces.

Barriers to achieving effective oral absorption of vaccines include their low permeability across the plasma membrane of intestinal epithelial cells, susceptibility to degradation by peptidases and proteases in the gastrointestinal tract (GIT), and hepatic and biliary clearance of absorbed components from the portal circulation. In the case of protein components, susceptibility to denaturation in the acidic environment of the stomach is also a barrier to oral delivery. Where oral administration of vaccines has successfully elilcited a potentially beneficial immune response, the dose of antigen is often very high. This negatively affects the economics since the cost of goods is high. Dose sparing technologies are therefore required.

Protection of macromolecular vaccine components from acid and enzymatic attack through encapsulation in nano- and microparticulate dosage forms such as polylactide (PLA), polylactide-coglycolide (PLGA), or liposomal-based systems and use of enteric-coated capsules or tablets may offer some protection from enzymatic degradation and acidic attack. However, vaccine encapsulation into particulates such as PLA, PLGA, liposomes, or other particulates may not always be successful as delivery systems owing to their poor absorption into and across intestinal epithelial cells. More generally, even if high quantities of antigen and/or adjuvant can be delivered to the appropriate target (eg M cells and/or Peyer's patches in the GIT), they may not be in appropriate or optimal physico-chemical form (eg appropriately or sufficiently solubilized) to be effective.

Examples of prior art encapsulation and formulation of antigens for oral formulation include the following.

U.S. Pat. No. 5,352,448, Bowersock et al., issued Oct. 4, 1994, describes an oral vaccine formulation for ruminants comprising an antigen in a hydrogel matrix which protects the antigen from degradation in the rumen. The matrix results from cross linking methacrylic acid and methylene bis-acrylamide either in the presence of antigen or for subsequent impregnation by antigen following rehydration. The matrix is preferably pelletized by carrying out polymerisation in a 3-5 mm diameter cylinder followed by cutting the resulting solid cylinder into 3-5 mm thick discs. Ammonium persulfate and sodium bisulfite are exemplified as polymerisation initiators U.S. Pat. No. 5,674,495, Bowersock et al, issued Oct. 7, 1997, describes a vaccine composition for oral administration comprising an alginate gel in the form of discrete 1-100 μm microparticles made by spraying antigen plus alginate solution into a solution of calcium chloride to effect gelation of the droplets or by adding calcium chloride to an alginate/antigen emulsion. Polymers having functional groups which react with or have an affinity for the alginate surface may be used to coat the particles. Polylysine is an example of such a coating polymer. The microparticles may be formulated by dispersing them in hydrophilic carrier matrices such as classical hydrogels or alginate gel matrices to yield carrier matrix pellets (alginate microparticles in alginate carrier matrix) ranging in size from 2 to 8 mm. The pellets may be coated like the microparticles. This patent also describes a variant in which the microparticles are made with vaccine-containing gelatine in which case gelatine microparticles arise from solidification (via temperature reduction) of an emulsion with an unspecified oil. Stabilization of these gelatine microparticles is achieved by coating with poly-1-lysine.

U.S. Pat. No. 5,500,161, Andrianov et al., issued Mar. 19, 1996, describes microparticles made by dispersing a substantially water insoluble polymer in an aqueous solution in which the substance to be delivered (such as an antigen) is also dissolved, dispersed or suspended, and then coagulating the polymer together with the substance by impact forces (eg shear coagulation) or by chemical coagulation (eg by use of electrolytes, pH changes etc) to form both spherical and non-spherical microparticles. Although the term "microparticle" used in this patent is defined to mean a solid particle ranging in size between 1 and 1000 microns, the largest exemplified microparticles have diameters of 20 microns. According to the patent, microparticles of between 1 and 10 microns are used for certain biological applications such as vaccines.

U.S. Pat. No. 6,015,576, See et al., issued Jan. 18, 2000, describes lyophilized multilamellar liposomes which contain antigen. The liposomes are preferably larger than 20 nm and smaller than 20 μm to ensure adequate processing by macrophages. The liposome preparation is lyophilised before being packaged for oral administration as a pill or capsule which may be enteric coated.

U.S. Pat. No. 5,811,128, Tice et al., issued Sep. 22, 1998, describes compositions for delivering a bioactive agent (especially vaccine antigens) to an animal entailing the steps of encapsulating effective amounts of the agent in a biocompatible excipient such as poly (DL-lactide-co-glycolide), to form microcapsules having a size less than approximately ten micrometers. They are made by dispersing an aqueous solution of antigen in polymer solution in methylene chloride. This polymer solution is then added to an aqueous poly(vinyl alcohol) solution to form an oil-in-water emulsion from which the microcapsules are collected by centriguation and freeze drying. Suspensions of the microcapsules were administered using an intubation needle.

Chitosan microparticles may also be useful for oral vaccines. Van de Lubben et al in J. Drug Target, 2002, describe 1.7 μm chitosan microparticles being transported by M cells in an ex-vivo human cell model.

Li et al. in BMC Biotechnology, 2008, describe alginate-coated chitosan microparticles (initially 300 nm in mean size) for vaccine delivery. Antigen (bovine serum albumin) was loaded on the chitosan microparticles by incubating the microsparticles in albumin (resulting mean size 404 nm). Drops of a suspension of antigen-loaded microparticles were then introduced into sodium alginate solution to yield alginate-coated (antigen-loaded) microparticles which were re-dispersed into calcium chloride to crosslink the alginate layer on the surface of the microparticles (resulting mean size: 1324 nm).

One approach to enhance drug and particulate delivery into and/or across the intestinal epithelial barrier is to target particulate formulations to receptor sites of the intestine. For example, Higgins et al. in Pharmaceutical Research Vol 21, 2004, employ small organic peptido-mimetics of the glycoprotein UEA-1 lectin to target M-cells. These mimetics are adsorbed to fluorescein isothiocyante-loaded streptavidin polystyrene particles with a diameter of 0.289 μm using biotinylated peptides. Roth-Walter et al. in Vaccine, Vol 23, 2005, use 1-3 μm sized vaccine-loaded poly(D,L-lactic-co-glycolic acid) microspheres functionalized with alpha-L-fucose specific *Aleuria aurantia* lectin (AAL). Both these documents (Higgins et al. and Roth-Walter et al.) are incorporated herein by reference in their entirety.

Polylactide-coglycolide (PLG) systems, such as those described above, have been tested as potentially useful in both injectable and oral vaccine formulations as described by Vajdy et al. in Immunology and Cell Biology, Vol. 82, 2004, the entirety of which is incorporated herein by reference. This paper also describes use of emulsions as adjuvants for injectable vaccines and points out that potential toxicity of emulsion components constrains their use although adjuvants such as MF59 (squalene oil-in-water emulsion) by Chiron/Novartis and AS03 ie. squalene (10.68 milligrams), DL-α-tocopherol (11.86 milligrams) and polysorbate 80 (4.85 milligrams) by GSK have been registered e.g. as components of injectable flu vaccines. See for example the product information for Preprandrix™ on EMEA's website.

It would be desirable to be able to use emulsions as components of (or as adjuvants in) oral vaccine formulations.

U.S. Pat. No. 5,961,970 (Lowell et al) describes vaccine adjuvant compositions in the form of an emulsion of a plurality of submicron oil-in-water droplets having a particle size in the range of between about 30 nm to about 500 nm to effect enhanced immunogenicity of antigens incorporated intrinsically or extrinsically into the droplets. To achieve mucosal immunity, the emulsion may also comprise a mucoadhesive macromolecule. To facilitate intestinal uptake, the emulsions may be encapsulated in gelatin capsules or otherwise enterocoated to prevent their exposure to gastric fluids when the oral route of administration is selected. Furthermore, the emulsions may be lyophilized prior to their encapsulation in order to achieve added stability of the antigen. The emulsion particles have a hydrophobic core comprising a lipid or lipid-like composition (eg MCT) and are stabilized with amphiphilic and/or non-ionic surfactants which may be a natural biologically compatible surfactant such as phospholipid (e.g., lecithin) or a pharmaceutically acceptable non-natural surfactant such as TWEEN-80. The surfactant assists in maintaining particles within the desired size range and preventing their aggregation.

US patent application 2001/0043949 (Delgado et al) describes a microparticulate composition comprising a biodegradable synthetic polymer microparticle, an antigen and an enteric polymer forming a coating on the microparticle surface.

Oral vaccines should preferably be solid or substantially solid in order to facilitate processing and storage, enhance stability (especially antigen stability) and to avoid the need for cold chain handling—liquids tend to be less stable than solids while liquids require more elaborate filling and containment in vessels, vials, syringes etc than do solid dose vaccines.

PCT application WO/2008/122967 (Sigmoid Pharma Limited) describes an oral composition comprising minicapsules having a liquid, semi-solid, or solid core and FIG. 2 therein is a schematic of a semi-solid- or solid-filled minicapsule/minisphere wherein the active principle is solubilised or in a suspension form, with controlled release polymer coatings. Example 20 describes beads of an extruded emulsion drug suspension made from mixing an aqueous solution with an oil solution made up of squalene (a natural unsaturated hydrocarbon), Gelucire 44/14 and Labrafil MS1944 CS. The water-soluble active principle hydralazine is in the aqueous phase and the oil phase is 1.12 dry weight % of the formulation.

Dry powder vaccines exist for intra-nasal delivery as described for example by Garmise et al in AAP PharmSciTech, Vol. 7, 2006. Solid dose vaccines for oral delivery also exist but are rare with the principal example being cholera vaccine tablets in which heat-killed whole cells of *V. cholera* are tabletted using traditional techniques.

If it is desired to incorporate surfactants in a minicapsule or minisphere formulation of an emulsion, a particular challenge arises. The need for surface tension to create and maintain capsules during manufacture can preclude or limit use of surfactants as the reduction in surface tension caused by the surfactant can destroy the integrity of the capsule or cause a more monolithic format where for example a shell or capsular layer is desired. Thus it can be difficult to formulate liquid, emulsified or pre-solubilized active principles with surfactants.

It may be desirable that vaccine compositions release active principles (eg antigens and adjuvants) in the colon following oral administration. Such colon-specific delivery systems must prevent the release of the active principles in the upper part of the GIT yet release them on reaching the colon. In the art of pharmaceutical delivery, there are a number of formulation approaches including pH and time-dependent polymer-mediated technologies. However, while variations in pH between the small intestine and the colon are well documented, the differences can be small and can vary between individuals. This can make pH-dependent systems unreliable in obtaining a predictable drug release profile. Time-dependent systems depend on the transit time of the delivery system in the GIT. A major limitation with these systems is that in vivo variation in the small intestinal transit time may lead to release of the active principles in the small intestine (too early) or in the terminal part of the colon (too late). The patho-physiological state of the individual recipient of such oral drug delivery systems also has a significant effect on the performance of these time-dependent systems—patients with irritable bowel syndrome and inflammatory bowel disease (including Crohn's disease and ulcerative colitis) exhibit accelerated transit through the colon. Independently of these considerations, the size of the dosage form at the point of entry into the small intestine (pylorus) can have a significant effect on GI transit time and/or variability of response.

The intestinal mucosal immune network has evolved an ability to maintain relative unresponsiveness or tolerance (or "oral tolerance") to a wide array of antigens derived from dietary sources and commensal bacteria. According to Friedman et al., PNAS USA 1994; 91:6688-92, oral tolerance is mediated by the generation of active cellular suppression or clonal anergy and the determining factor is the dose of antigen fed orally. Oral tolerance is dose-specific and loss of tolerance occurs with increased dosages according to Nagler-Anderson et al., PNAS USA 1986; 83:7443-6. Low dose of antigen administration favours the induction of active cellular regulation according to Chen et al., 1994 Science; 265:1237-1240. Higher doses favour the induction of clonal anergy or deletion according to Chen et al., 1995 Nature; 376:177-180. In a particular study, high doses of myelin basic protein (MBP) to mice whose T-cells carry a T-cell receptor (TCR) specific for MBP resulted in T-cell activation and receptor down modulation (Benson et al., 2000 J Clin Invest, 106:1031-1038). Additionally, oral tolerance can be enhanced by feeding immune adjuvants such as lipopolysaccharide or cholera toxin subunit B, which appear to stimulate additional populations of cells to down-regulate immune responses (Khoury et al., J Exp Med 1992; 176:1355-64).

Oral tolerance has been shown to prevent or treat a variety of T-cell mediated autoimmune disorders. For example, in a double-blind pilot trial involving 30 patients with multiple sclerosis, oral administration of bovine myelin antigens decreased the number of T-cells that reacted with myelin basic protein, with no measurable toxicity (Werner et al., Science 1993; 259:1321-4). Trentham et al demonstrated clinical efficacy of oral tolerance by feeding type II collagen to 60 patients with severe, active rheumatoid arthritis (Trentham et al., Science 1993; 261:1727-30). In an animal model of trinitrobenzene sulfonic acid (TNBS), Th1-mediated colitis, it was reported that feeding colonic extracts haptenated with TNBS prevented the development of mucosal inflammation (Neurath et al., J Exp Med 1996; 183:2605-16). In a Phase I study to evaluate the safety and efficacy of autologous colonic protein extract feeding for the treatment of moderate-to-severe Crohn's Disease, Margalit et al. demonstrated safety and induced remission in 7 out of 10 subjects (Am J Gastroenterol 2006; 101). Other animal disease models, including stroke, Alzheimer's disease and atherosclerosis as well as type 1 diabetes have responded to mucosal administration of antigens.

Various responses are induced or suppressed during oral tolerance beginning when antigen first encounters gut-associated lymphoid tissue (GALT), a well developed immune network consisting of lymphoid nodules (Peyer's Patches), epithelial villi, intraepithelial lymphocytes, and other lymphocytes scattered throughout the lamina propria in the GIT.

More generally, the lamina propria is a constituent of the moist linings (mucous membranes or mucosa) which line various tubes in the body (such as the respiratory tract, the gastrointestinal tract, and the urogenital tract). Thus, the lamina propria (more correctly lamina propria mucosae) is a thin layer of loose connective tissue which lies beneath the epithelium and together with the epithelium constitutes the mucosa. The lamina propria contains capillaries and a central lacteal (lymph vessel) in the small intestine, as well as lymphoid tissue. Lamina propria also contains glands with the ducts opening on to the mucosal epithelium, that secrete mucus and serous secretions.

Antigens may act directly at the level of the GALT or may exert their effects after absorption. Oral tolerance and mucosal immunization form part of an immunologic continuum related to antigen presenting cell interactions with T cells in the GALT. Distinct sections of the GI tract can be distinguished. The rectum/colon is a mix of immune inductive (organised lymphoid tissues) and effector sites (diffuse lamina propria) whereas the jejunum contains almost no immune inductive sites. This is reflected in the lymphoid composition of each tissue: the jejunum contains mostly memory $CD4^+$ T cells, while the colon contains a larger proportion of naïve $CD4^+$ T cells (Veazey and Lackner, 2006; PLoS Medicine; 3:12-2188-9).

In acute HIV infection, a rapid and profound loss of $CD4^+$ $CCR5^+$ T cells occurs within days of infection, whereas peripheral lymphoid tissues such as blood and lymph nodes, which harbour mainly naïve $CD4^+$ T cells, are less severely affected (Brenchley et al., 2004 J Exp Med 200:749-759). Mehandru et al. studying lymphocyte populations from the intestine and peripheral blood obtained from recently HIV-infected patients as well as uninfected volunteers demonstrated that most patients who initiate high activity anti-retroviral therapy (ART) as early as possible after HIV infection still do not experience complete restoration of intestinal $CD4^+$ T cells to baseline levels, regardless of the duration of therapy. Instead, HIV infection results in a continuous state of activation in the intestinal immune system that is not reflected in peripheral lymphoid tissues (Mehandru et al., 2006; PLoS Med 3(12): e484). The data from Mehandru et al. provide evidence that intestinal inflammation and continual infection, destruction, and turnover of CD4+ T cells occur in patients on ART. This would suggest that drugs with better intestinal tissue distribution, together with, perhaps, mechanisms to reduce or prevent immune activation in mucosal tissues may more effectively combat HIV infection.

A number of colon targeted delivery systems have been investigated. These systems include: intestinal pressure-controlled colon delivery capsules which rely on peristaltic waves occurring in the colon but not in the stomach and small intestine; combination of pH-sensitive polymer coatings (remaining intact in the upper GIT) with a coating of polysaccharides degradable only by bacteria found in the colon; pectin and galatomannan coating, degraded by colonic bacteria; and azo hydrogels progressively degraded by azoreductase produced by colonic bacteria. The preceding four systems are reviewed by Yang et al., International Journal of Pharmaceutics 235 (2002) 1-15, the entirety of which is incorporated herein by reference. Polysaccharide based delivery systems are of particular interest—see e.g. Kosaraju, Critical Reviews in Food Science and Nutrition, 45:251-258 (2005) the entirety of which is incorporated herein by reference. Nevertheless, for systems solely reliant on specific enzymatic activity in the colon, disease state can once again cause variability in the drug release profile as a result of pathological derangements in colonic flora (eg resulting from pH changes and changing amounts/activity of bacterial enzymes).

It is not unusual that multiple immunizations are required for many vaccines to be successful. For paediatric population, up to five immunizations may be needed, as is the case for diphtheria, tetanus, and pertussis (DTP) vaccine, which is given three times during the first six months after birth, followed by a fourth dose in the second year of life, and a final boost between four and six years of age. However, some of the vaccines need additional boosts even in adults who have already received the complete immunization series, for example, the tetanus-diphtheria (Td) vaccine, for which a boost is recommended every 10 years throughout a person's lifespan. The "prime-boost" principle applies to live attenuated vaccines (e.g. oral polio vaccine), inactivated vaccines (e.g. hepatitis A vaccine), recombinant protein subunit vaccines (e.g. hepatitis B vaccine), and polysaccharide vaccines (e.g. *Haemophilus influenzae* type b vaccine). For these vaccines, the prime-boost is 'homologous' because the same vaccines given in the earlier priming immunizations are used for subsequent boost immunizations. For more detailed discussion, see Curr Opin Immunol. 2009 June; 21(3):346-51. Epub 2009 Jun. 6, the entirety of which is incorporated herein by reference.

Over the past decade, studies have shown that prime-boost immunizations can be given with unmatched vaccine delivery methods while using the same antigen, in a 'heterologous' prime-boost format. The most interesting and unexpected finding is that, in many cases, heterologous prime-boost is more effective than the 'homologous' prime-boost approach. The rapid progress of novel vaccination approaches, such as DNA vaccines and viral vector-based vaccines, has certainly further expanded the scope of heterologous prime-boost vaccination and frequently used heterologous prime-boost vaccinations include DNA priming followed by boosting with recombinant protein, inactivated vaccine, viral vectors and BCG; priming with viral vector followed by boosting with recombinant protein; and priming with BCG followed by boosting with viral vector.

It is known that effective B cell-mediated immunity and antibody responses often require help from CD4+ T cells. It is thought that a distinct CD4+ effector T cell subset, called T follicular helper ($T_{FH}$) cells, provides this help. According to Johnston et al's work published online in Science on Jul. 16, 2009 (DOI: 10.1126/science.1175870) the entirety of which is incorporated herein by reference, expression of the transcription factor Bcl6 in CD4+ T cells is both necessary and sufficient for in vivo $T_{FH}$ differentiation and T cell help to B cells in mice. These researches also state that in contrast, the transcription factor Blimp-1, an antagonist of Bcl6, inhibits $T_{FH}$ differentiation and help, thereby preventing B cell germinal center and antibody responses. Thus $T_{FH}$ cells are required for proper B cell responses in vivo and that Bcl6 and Blimp-1 play central yet opposing roles in $T_{FH}$ differentiation.

BRIEF SUMMARY OF THE DISCLOSURE

In accordance with the present invention there is provided a composition comprising a water-soluble polymer matrix in which are dispersed droplets of oil, the composition comprising an active principle for immune modulation e.g. vaccination. The active principle is an immunomodulator and in many embodiments comprises, or is, an adjuvant and/or an antigen. A composition may contain a plurality of active principles. The invention includes embodiments in which the active principle is included in at least some of the oil droplets as well as embodiments in which the oil droplets are free of active principle. The oil droplets are released as the matrix containing them dissolves in an aqueous medium. In one embodiment, the oil droplets are substantially immobilized in or by the matrix and the immobilizing feature is lost as the matrix dissolves in aqueous media. In certain embodiments, the oil drops may collectively be referred to as the oil phase of the composition of the invention. The composition may be for oral administration, by way of example.

As explained later in this specification, the oil drops (oil phase) may consist of a single liquid oleo-phase or be a water-in-oil emulsion. In either case, it is considered (without being bound by theory) that the oil drops have an external oily medium which interfaces with the aqueous phase (matrix phase) of the composition; the external oily medium optionally contains an internal water phase such that the oil drops comprise a water-in-oil emulsion or such an internal water phase is absent such that the oil drops have a single liquid oleo-phase.

The composition may be in the form of a mini-bead. The mini-bead may have a diameter of from 0.5 mm to 5 mm, e.g. from 0.5 mm to 2.5 mm. The invention includes population of minibeads (e.g. 10 or more minibeads and optionally at least 100 or more minibeads) consisting essentially of, or comprising, minibeads of the disclosure. The invention includes a product comprising a multiplicity of minibeads, e.g. containing minibeads all of which are minibeads of the disclosure; such a product may be a dosage product, for example a capsule, a suppository, a pessary, a sachet or a tablet, In a preferred embodiment, the composition of the invention comprises at least one antigen and at least one adjuvant described in more detail below.

In another embodiment, the present invention provides a vehicle for delivery of active principles for vaccination which can be of various types in particular antigens, antigenic material or adjuvants, or a combination thereof.

In particular, the invention provides intestinal/colonic mucosal vaccine compositions or immunotherapeutics. Included also, therefore, are compositions of the invention, e.g. vaccine compositions or immunotherapeutics, for delivery of an immunomodulator to the intestinal mucosa and/or colonic mucosa. The invention also provides a composition as described herein for the development and/or induction of oral tolerance.

The invention also provides a number of immune-mediated approaches, including methods, for the prevention, delay in progression of and/or treatment of disease. Such approaches and methods also allow combination with non-immune-mediated approaches, for example combination with release (especially controlled release) of non-immune-mediated therapeutics, e.g. small or large pharmaceutical molecules, optionally for delivery along the entire intestinal and colonic/rectal tract or to pre-specified sites along same. The non-immune mediated drugs may therefore be "small molecules" or "biologicals".

In a particular embodiment, the disease is HIV/AIDS, although the invention is not limited thereto and many other diseases are contemplated, for example as described elsewhere herein. In the case of HIV/AIDS for example, the invention allows combination of such immune-mediated approaches and methods with release (especially controlled release) of ARTs (anti-retroviral therapeutics) along the entire intestinal and colonic/rectal tract or to pre-specified sites along same. Thus the invention provides, in one embodiment, a combination ART/immune system modulation approach.

The invention relates also to the treatment, prevention or delay in progression of conditions, particularly gastro-intestinal conditions, exacerbated or caused directly or indirectly by an infectious agent, for example one or more of those listed elsewhere herein comprising administering a composition of the invention, particularly a vaccine composition, to an animal e.g. orally.

The invention also provides a means of preventing or reducing the development of antibodies against otherwise immunogenic pharmaceuticals e.g. biologics, such as peptide or protein therapeutics and antibodies, e.g. by tolerising a patient to the relevant pharmaceutical prior to administration of therapeutic doses of the pharmaceutical.

The extent to which dissolution may affect the composition's physical form and features depends on the initial shape, size and make-up of the composition. Where the composition bears a coat, the rate and manner of dissolution can be modified (see below) and/or it can be modified by inclusion of a retardant/protectant as described below in relation to HPMC derivatives.

In one aspect, the present invention can be described as a dried oil-in-water (o/w) emulsion, one embodiment of which is non-powdered. Another embodiment is moulded and/or shaped and/or extruded e.g. in the form of beads, especially mini-beads. The composition of the invention generally comprises multiple oil drops or droplets within a moulded or shaped form, e.g. a mini-bead.

In another embodiment, the composition comprises beads, e.g. mini-beads, coated with a polymer to alter the release profile. The composition of the invention may therefore be in the form of uncoated beads or coated beads, e.g. beads coated with a polymer; the beads may be mini-beads. In a related embodiment, the present invention provides a vaccine composition or an immunotherapeutic composition comprising a plurality of optionally coated mini-beads of a water-soluble polymer matrix. In a particular embodiment, the present invention provides a composition comprising a plurality of mini-beads of dried oil-in-water emulsion. For all mini-bead compositions disclosed herein, the invention includes an individual bead and, as another aspect, a population of beads.

In the case both of a vaccine composition comprising a population of beads and an immunotherapeutic composition comprising a population of beads, at least some of the mini-beads may comprise an active principle for immune modulation, i.e. an immunomodulator; the mini-beads may comprise a single active principle or a combination of active principles provided that they comprise an immunomodulator, particularly an antigen or hapten. Thus, the invention includes compositions in which a first population of mini-beads comprises an immunomodulator, whether as a sole active principle contained in the first population or a combination of active principles contained in the first population, and a second population of mini-beads, different from the first population, comprises an active principle (whether a sole active principle or a combination of active principles) which may be the same as or different from the active principle or active principle combination of the first population; the second population may comprise an active principle which is an immunomodulator or may be free of immunomodulators. In some embodiments, there is at least one population of mini-beads comprising an active principle (for example one, two or three populations comprising an active principle, provided that there is at least one immunomodulator in the composition) and at least one population be free of active principles. In related embodiments, the composition of the invention may comprise multiple populations of mini-spheres or mini-beads. The active principles may be the same or different as between populations and where more than one active principle or category of active principle is present, each such principle or category may be the same or different as between populations.

In a specific embodiment, one or more active principle(s) for immune modulation is (are) incorporated in the oil phase of the composition or dried emulsion. In another specific embodiment, one or more active principle(s) for immune modulation is (are) incorporated in the aqueous phase of the composition or dried emulsion. In a related embodiment, the one or more active principle(s) is (are) incorporated in both the oil phase and the aqueous phase. Some sub-classes of the embodiments mentioned in these paragraphs additionally have non-immunomodulatory active principles incorporated in them.

The composition of the invention is of particular interest for active principles for immune modulation, in particular vaccine active principles, of low aqueous solubility and/or liposoluble compounds (active principles) where incorporation into the oil phase brings particular advantages.

Thus in one aspect, the relation relates to formulating active principles for immune modulation, in particular vaccine active principles, for oral administration as mini-beads of dried oil-in-water emulsions in which the active principle can be incorporated in the oil phase of the emulsion and with the beads being optionally coated with a polymer.

The water-soluble immobilizing polymer matrix (or in one aspect, the aqueous phase of a dried emulsion) comprises, in one embodiment, a cross-linked water-soluble polymer e.g. resulting from chemical or physico-chemical (eg drying) solidification of a fluid aqueous continuous phase such that, in the matrix or dried emulsion, water is substantially absent and the oil droplets are immobilized. In this embodiment, the dried aqueous phase can therefore be referred to as an immobilization matrix.

In the presence or absence of a polymer coat, the composition of the invention may include a component to protect the active principles for immune modulation, in particular vaccine active principles, from exposure to gastric (stomach) fluids. Such component may for example prevent the disaggregation or dissolution of the composition in the stomach and allow such disaggregation or dissolution only once the small intestine has been reached. A preferred component in this embodiment is a polymer which is water-soluble or substantially water-soluble only above a certain pH such as derivatives of hydroxypropyl methylcellulose (HPMC) described in more detail below. An optional additional component in relation to this embodiment is inclusion in the composition of compounds to maintain the pH above such threshold. Such inclusion may for example result from inclusion in the composition of the invention during manufacture of basic or alkalinic compounds in conjunction with the polymer having pH-dependent solubility. In other embodiments dispersion is sufficient e.g. at pH below the dissolution threshold. In a related embodiment, substances may be included to maintain the pH below the dissolution threshold in order to slow dissolution.

In one embodiment the invention therefore provides a composition which protects the one or more active principle(s), e.g. protein or peptide, from degradation or stabilizes it/them and/or provides delivery of such active principle(s) to the colon.

The term "dried emulsion" generally means an emulsion whose internal (discontinuous) phase has been immobilized in a substantially solid or solidified external phase. The solid external phase dissolves on contact with an aqueous medium.

The term "matrix" is a term well-known in the art and generally means, according to context, a solid, semi-solid, undissolved or not-yet-dissolved material which provides structure and volume to a composition. In some contexts, the term "matrix" may mean a scaffold.

Solidification of the external phase may have arisen through various means including chemically (eg by cross-linking) or physically (eg by cooling or heating). By use of the term "dried", it is not sought to imply that a drying step is necessary to produce the dried emulsion (although this is not excluded) rather that the solid or solidified aqueous external phase is substantially free of water or free of available water. In this respect, the term "aqueous phase" is nevertheless employed in this document to denote the external (continuous) phase of the composition of the invention even though water, in certain embodiments, is largely absent from (or trapped within the matrix of) the composition of the invention, particularly when in the form of mini-beads. The external phase of the composition of the invention is however water-soluble and dissolves in aqueous media. In one embodiment, the oil droplets are released when the aqueous phase dissolves or is exposed to aqueous media.

The term "released" in relation to the oil droplets means free to move, egress, coalesce, dissolve, (re)emulsify etc. although actual movement, egression, coalescence, association or (re)emulsification is not a requirement ie. may not occur and indeed may intentionally be constrained e.g. by presence of a coat or coating.

In one embodiment, the composition comprises one or more surfactants, preferably comprising or selected from non-ionic surfactants, described in more detail below.

Another aspect of the present invention is the make-up of the optional polymeric coating. For instance, inclusion of a polymer which degrades in the presence of bacterial enzymes present in the colon (and/or a polymer which encourages the formation of pores in the coating—a "pore-former") with a pH-independent polymer leads to availability of vaccine components in active form substantially in the colon or other pre-determined site of the GI tract. In a particular embodiment, the above mentioned polymer degradable by bacterial enzymes is water-soluble.

In one embodiment of the invention, the dried emulsion forms a matrix or net-like structure which is effective in trapping or encapsulating vaccine antigen.

In one embodiment, the invention provides a composition comprising a solid phase comprising a water-soluble polymer matrix material and an oil phase dispersed in the solid phase.

In one embodiment, the composition of the invention further comprises one or more agents to enhance adsorption of vaccine antigen onto, and absorption by, mucosal surfaces and/or the underlying mucosal lymphoid tissue, M-cells, Peyer's patches or other immune relevant cells or cell systems. The absorption-enhancing agent may be as described in the prior art such as for example Swenson, E S and Curatolo, W J Means to Enhance Penetration (2) Intestinal permeability enhancement for proteins, peptides and other polar drugs: mechanisms and potential toxicity. *Advanced Drug Delivery Reviews.* 1992. 8:39-92 the entirety of which is hereby incorporated herein by reference. An example of such an agent is lecithin. Other examples of such agents are lectins (Jepson M A et al., *Advanced Drug Delivery Reviews*, Volume 56, Issue 4, 3 Mar. 2004, pages 511-525). See also Davis I C et al., The immunopathology of M cells, Springer Seminars in Immunopathology Volume 18, Number 4, 421-448.

The vaccine composition of this invention makes it possible to vaccinate via a mucosal surface, such as oral cavity, gut, nasal, rectal, or vaginal surfaces. For rectal administration, the vaccine composition may be in the form of a suppository. For vaginal administration, the vaccine composition may be in the form of a pessary (or vaginal suppository) e.g. in the form of a ring which may be biodegradable. For oral administration, the vaccine composition may be in the form of a pill or tablet form (as moulded or e.g. comprising a plurality of mini-beads). The composition may also be in paste form or in fluid form and may be administered using a dropper or needle less syringe. The vaccine composition of the invention also allows a method of vaccination via food and/or water (or drink) as well as solid dose administration.

Compositions of the invention may be for administration to human subjects.

In certain embodiments, the composition of the invention is suitable for administering a vaccine to an animal, for example a human or an animal selected from the following groups: cattle, swine, poultry and fish. The vaccine may be administered as part of feed or drink to such animals or introduced into the water in which fish reproduce, eat or otherwise dwell. The composition of the invention may be formed into shapes of animal, poultry or fish foodstuffs and/or contain attractants such as glitter, scent and/or flavour.

The present invention also provides methods of vaccinating or inducing an immune response in an animal e.g. fish or human or other mammal and/or of one or more of the diseases described elsewhere herein comprising administering to the animal the composition according to the invention. Administration to a human can be by the patient him/herself, by a health care worker or indirectly, e.g. in the case of animals, by addition to food or drinking water.

Vaccines for and vaccination of non-mammalian animals including fish or other aquatic life forms is also contemplated by the present invention.

The composition of the invention may be formulated in capsules, suppositories, pessaries or may be used in extracorporeal devices or other health-related e.g. medical or other devices.

In accordance with the invention, there is also provided a method for preparing an immune modulating (eg vaccine) composition comprising mixing an aqueous solution of the water-soluble polymer matrix with an oil-based liquid to form a water-in-oil emulsion and then causing the resultant suspension to solidify into one or more shaped elements e.g. beads. The active principles may be initially present in either the oil phase or the liquid phase, or both.

In this embodiment, the method preferably involves adding one or more immunomodulators, in particular antigens and/or adjuvants, to the oil phase before emulsion formation. In a related embodiment, the method preferably involves adding one or more immunomodulators, in particular antigens and/or adjuvants, to the aqueous phase before emulsion formation. In another related embodiment, the same or different immunomodulators, in particular antigens and/or adjuvants, can be included in either the oil phase or aqueous phase or both prior to emulsion formation.

In accordance with the present invention there is also provided a vaccine delivery composition that adsorbs the vaccine onto a mucosal surface of a mammal, and optionally, following absorption of some or all of the components of the vaccine composition, that brings the vaccine into contact with mucosal-associated lymphoid tissue (MALT). The invention also includes vaccine compositions that, after administration, result in or achieve presentation of vaccine active principle to a mucosal surface of a mammal, e.g. MALT.

In an embodiment of the present invention there is provided oral administration of a vaccine against a gut pathogen comprising presentation or delivery of the vaccine to the gut-associated lymphoid tissue (GALT).

In an embodiment of the present invention there is provided oral administration of a vaccine against an upper respiratory pathogen comprising presentation or delivery of the vaccine to the mucosal-associated lymphoid tissue in the oral cavity or nasal passages.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The readers attention is directed to all papers and documents which are filed concurrently with or previous to this specification in connection with this application and which are open to public inspection with this specification, and the contents of all such papers and documents are incorporated herein by reference.

At least in embodiments, the invention ameliorates or solves one or more of the shortcomings of the prior art. In particular, the invention comprises formulations or compositions which enable multiple problems of the prior art to be solved. In various embodiments of the invention, certain components or features mentioned above in the review of the prior art may also be included in the composition of the invention.

BRIEF DESCRIPTION OF THE DRAWINGS

Embodiments of the invention are further described hereinafter with reference to the accompanying drawings, in which.

DETAILED DESCRIPTION

Figure 1:
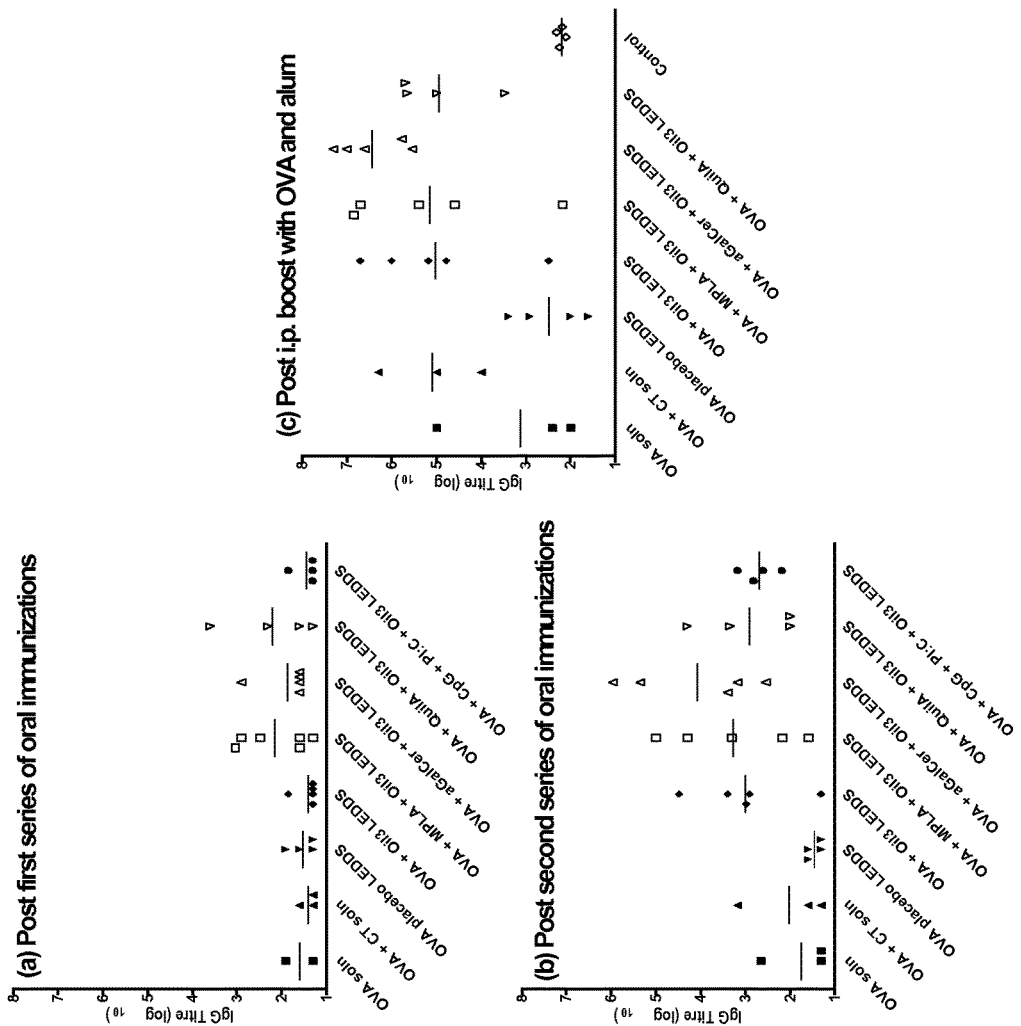
FIG. 1 comprises plots of individual end-point IgG titres of BALB/c mice immunised orally with mini-bead compositions of the invention designated "LEDDS" in the legend and with comparative solutions, as described in Example 7.

The present invention in one aspect concerns a composition comprising an immunomodulator, particularly an immunostimulant, e.g. an antigen or hapten. The composition is suitably administered by a route other than injection and, at least when administered into a human or animal by such a non-injection route, normally induces a more intense immune response to the immunomodulator than when the immunomodulator (e.g. antigen or hapten) is administered alone. The present invention also concerns vaccines comprising an antigen or group of or combination of antigens and one or more adjuvants described below. As will appear, the present invention also concerns methods of making and using the foregoing immunomodulating compositions.

The present invention includes within its ambit a pharmaceutical composition comprising a water-soluble polymer matrix in which are dispersed droplets of oil, the composition comprising an active principle. The composition may be described as comprising a water-soluble polymer matrix and an oil phase in the form of oil droplets dispersed in the matrix, the composition comprising an active principle. The active principle is an immunomodulator and may be an antigen or an adjuvant. More than one active principle may be comprised in the composition. In one implementation of the invention, both an antigen and an adjuvant are included in the composition, and optionally more than one antigen and/or more than one adjuvant. The invention therefore includes within its scope (i) pharmaceutical compositions comprising a water-soluble polymer matrix in which are dispersed droplets of oil, the composition comprising at least one active principle for immune modulation selected from an adjuvant, an antigen or a combination thereof, and (ii) pharmaceutical compositions comprising a water-soluble polymer matrix and an oil phase in the form of oil droplets dispersed in the matrix, the composition comprising at least one active principle for immune modulation selected from an adjuvant, an antigen or a combination thereof. The oil phase (i.e. at least some of the oil droplets) may include active principle.

The distribution of active principle and other constituents between the matrix and the oil phase is not known. Whilst it is known in which phase(s) (oil phase or future matrix phase) constituents are incorporated in the manufacture of a composition, it is not known to what extent, if any, constituents will have changed phase in the final composition. However, since oleophilic substances are included in the oil phase during manufacture and hydrophilic substances in the aqueous phase (the future matrix), it is assumed that at least a portion of each constituent, and possibly all of it, will in the solidified composition remain in its initial phase.

The invention includes compositions which comprise one or more surfactants, the surfactants optionally being selected from non-ionic surfactants. It is considered that, in embodiments, at least a portion of the one or more surfactants and optionally the whole surfactant content of the composition is in the oil droplets. (It will be understood by the skilled reader that, when the whole surfactant content of the composition is in the oil droplets, trace amounts of surfactant may enter the matrix, and this specification is to be read in a practical manner which appreciates that trace amounts of any component may enter one phase of the composition from another phase thereof).

Across the entire scope of the disclosure, the invention includes compositions having one or more coatings on the matrix; in embodiments, the compositions have a polymeric coating (for example a single coating or two coatings). Polymeric coatings may serve to modulate, e.g. control, release of the active principle, and for example may degrade in the presence of bacterial enzymes in the colon or may be enteric coatings (coatings of both these types may be present). Compositions may include a coating which comprises a pore-former. As is known, a pore-former promotes the formation of pores in the coating at the desired release site. The pore-former is typically soluble when it is exposed to GI tract fluid at the release site. In embodiments, compositions have a coating which comprises a pH-independent polymer and a pore former; for example, the pore-former may promote pore formation in the colon. A composition may have both a coating comprising a pore-former effective in the colon and a coating degradable in the colon.

The compositions of the invention may comprises one or more agents to enhance adsorption of vaccine antigen onto, and absorption by, mucosal surfaces and/or the underlying mucosal lymphoid tissue, M-cells, Peyer's patches or other immune relevant cells or cell systems. The agents used may be ones known in the art. Examples of such agents are lecithin and lectins.

Compositions of the invention may be suitable for oral administration. Compositions of the invention may be adapted for oral administration, optionally to the exclusion of any other route of administration.

In one embodiment, the compositions are adapted for oral administration and for release of the oil droplets in the intestine. For example, such compositions may comprise an enteric polymer in the matrix.

The invention includes compositions as disclosed herein which have a coat (e.g. a single coat or two coats) to provide controlled or targetted release of the oil droplets. In one class of implementations, the composition includes an enteric polymer, e.g. an HPMC such as HPMCP, for example.

One class of compositions comprise a water-soluble matrix and an oil phase in the form of oil droplets dispersed in the matrix, the oil phase comprising an antigen and an adjuvant and the composition comprising an enteric material to protect the antigen and adjuvant against gastrointestinal proteolysis. The enteric material may form or be comprised in an outer coating, or it may be included in the matrix or it may be included in the oil phase, or it may be in a combination of two or three of these locations (e.g. form or be comprised in an outer coating and be included in the oil phase). In some embodiments the enteric material forms or is comprised in an outer coating and is absent from the matrix and the oil phase.

As previously indicated, the compositions of the disclosure, including those mentioned in the immediately preceding two paragraphs, may take the form of minibeads, which minibeads may by way of example have a diameter of from 0.5 mm to 5 mm, e.g. from 0.5 mm to 2.5 mm. The invention therefore includes compositions in the form of a minibead and wherein the droplets of oil constitute an oil phase and the oil phase comprises an antigen and an adjuvant, the minibead optionally further comprising an enteric material to protect the antigen and adjuvant against gastrointestinal proteolysis, such enteric minibeads being suitable for oral administration. In some embodiments, enteric material forms or is comprised in an outer coating, or is included in the matrix and/or in the oil phase. In other embodiments, the enteric material forms or is comprised in an outer coating and the composition does not contain a base; the disclosure includes compositions in which the matrix which is free of base. The disclosure also includes compositions which do contain base, e.g. in the matrix (aqueous phase). The invention includes across its entire scope embodiments in which the oil phase comprises one or more surfactants, optionally selected from, or comprising, non-ionic surfactants.

As demonstrated in the examples, the invention comprises compositions which are immunogenic and are effective in providing protection against challenge by a toxic antigen when administered orally. It is not known which feature(s) of the compositions of the invention contribute to the achievement of such immunogenic effect but, without being bound by theory, it is believed that the presentation of the oil phase as droplets may be one factor. In this regard, data suggest a possible link between smaller droplet size and enhanced immunostimulatory effect. It has also been observed that incorporation of antigen (ovalbumin) into beads of a water-soluble matrix without an oil or an adjuvant is ineffective, i.e. that mere protection of the antigen is insufficient to obtain an immunostimulatory effect.

Available data suggest that, for compositions in which the oil phase comprises an antigen and an adjuvant, the immunostimulatory effect is facilitated by the presence of the oil phase as droplets and the inclusion of the antigen in the oil phase, such that the antigen is presumably presented to the body in the form of small oil droplets. The adjuvant, which in this embodiment is also in the oil droplets, serves to enhance immunogenicity to a better level and is therefore preferred. As regards the theory presented in this paragraph, the reader is reminded that the interpretation of this invention is not bound by theory.

In a further aspect of the disclosure, there is provided a product comprising a first population of minibeads comprising a water-soluble polymer matrix in which are dispersed droplets of oil and a second population of minibeads comprising a water-soluble polymer matrix in which are dispersed droplets of oil, wherein the first and second populations of minibeads are different and at least the minibeads of the first population are minibeads of the invention. The two populations may be composed of mini-beads of the invention and differ as to active principle(s) and/or excipients (e.g. the presence, absence, amount, location and/or identity of release-modulating polymer). The product may be a pharmaceutical formulation, for example a capsule, a tablet, a suppository or a pessary, or a paste or a fluid.

An aspect of the invention resides in the use of a liquid aqueous external phase comprising a water-soluble polymer in which is dispersed oil droplets to make a composition of the disclosure by causing or allowing the aqueous phase to undergo solidification, e.g. by cross-linking, cooling or heating.

Further provided by the invention is a method for preparing an immune modulating (e.g. vaccine) composition comprising mixing an aqueous solution of a water-soluble polymer with an oil-based liquid to form a water-in-oil emulsion, at least one of the aqueous solution and the oil-based liquid comprising an antigen or an adjuvant or a combination thereof, and then causing or allowing the resultant suspension to solidify into one or more beads or other shaped elements.

The oil-based liquid used in the method of preparation may comprise an antigen or an adjuvant or a combination thereof; in one embodiment it comprises a combination thereof. In certain implementations of the method, the aqueous solution does not comprise an antigen or an adjuvant or a combination thereof. In other implementations of the method, the aqueous solution comprises an adjuvant (in which case the oil-based liquid may be free of adjuvant or may contain adjuvant). The disclosure includes implementations of the method in which the aqueous solution comprises an antigen (in which case the oil-based liquid may be free of antigen or may contain antigen).

The method may further comprise coating the beads or other shaped elements, for example with a coating material described herein, e.g. with an enteric and/or other polymer coating. The shaped elements are in one class of methods beads having a diameter as described herein, e.g. of from 0.5 mm to 2.5 mm. In one embodiment, the method comprises further comprises processing the shaped elements into a capsule, a tablet, a suppository, a pessary or another dosage form for administration. All embodiments and features of the compositions of the invention described elsewhere herein are applicable to the just-described preparation and the products thereof.

One embodiment excludes the subject matter of Examples 51-53 of the applicant's application PCT/EP2010/056838. Accordingly, in an optional embodiment of the invention, the composition is not one set out in the following tables reproduced from Examples 51-53 of PCT/EP2010/056838:

| Composition | mg/g |
| --- | --- |
| Ovalbumin | 6-10 |
| alphaGalCer | 0.1-0.5 |
| Montanide ISA 720 | 70-120 |
| Labrafil M 1944 CS | 280-320 |
| Span 85 | 1-5 |
| Tween 80 | 1-5 |
| Gelatin | 450-550 |
| D-Sorbitol | 50-80 |
| NaOH | 1-10 |
| HPMCP | 30-80 |

| Composition | mg/g |
| --- | --- |
| rCTB | 1-5 |
| alphaGalCer | 1-5 |
| Montanide ISA 720 | 80-120 |
| Labrafil M 1944 CS | 250-300 |
| Span 85 | 10-20 |
| Tween 80 | 25-35 |
| Gelatin | 450-550 |
| D-Sorbitol | 30-60 |
| NaOH | 5-10 |
| HPMCP | 30-60 |

| Composition | mg/g |
| --- | --- |
| rCTB | 1-5 |
| alphaGalCer | 1-5 |
| Montanide ISA 720 | 60-100 |
| Labrafil M 1944 CS | 200-260 |
| Span 85 | 5-20 |
| Tween 80 | 20-50 |
| Gelatin | 500-600 |
| D-Sorbitol | 50-70. |

Also included in the disclosure are optional embodiments of the invention in which the formulations do not contain 6-10 mg/g ovalbumin or, alternatively, do not contain 1-5 mg/g of subunit B of cholera toxin and, in either case, do not contain D-sorbitol. Further included in the disclosure are optional embodiments of the invention in which the formulations do not contain 6-10 mg/g ovalbumin or 1-5 mg/g of subunit B of cholera toxin.

The invention includes methods for the treatment or prevention of a gastro-intestinal condition exacerbated or caused directly or indirectly by an infectious agent, comprising administering the composition according to the invention to an animal e.g. orally. Also included are methods of boosting immune response comprising orally administering a vaccine composition of the disclosure to an animal which has received a priming vaccination non-orally. Another aspect of the invention resides in methods of vaccination or inducing an immune response, comprising bringing the composition the disclosure into contact with a mucosal surface, such as oral cavity, gut, nasal, rectal, or vaginal surfaces, the method for example comprising administering the composition orally, nasally, rectally or vaginally. Further included are methods of vaccination comprising administering the composition of the disclosure as part of feed or drink to animals or introduced into the water in which fish reproduce, eat or otherwise dwell. An aspect of the invention is methods of vaccinating or inducing an immune response in an animal (e.g. mammal or fish) comprising administering to the animal the composition of the disclosure.

Figure 2:
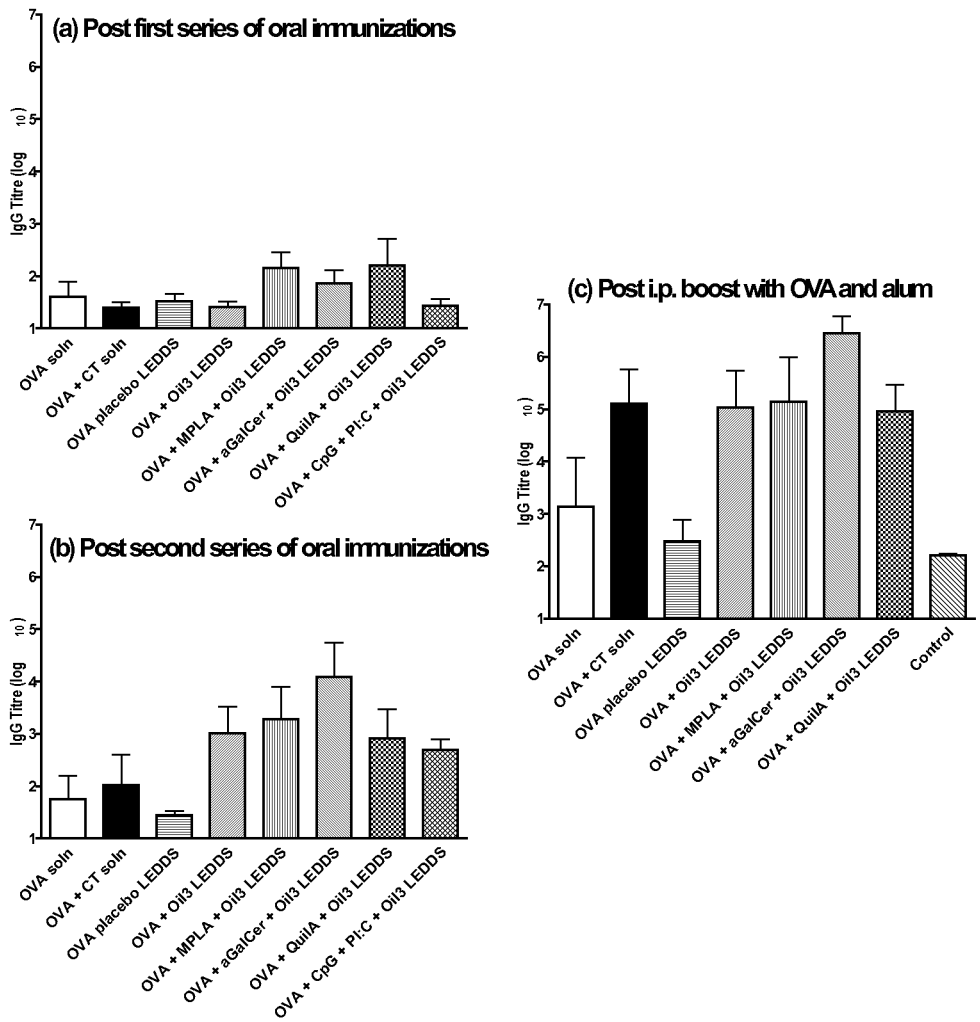
FIG. 2 comprises plots of mean end-point IgG titres of BALB/c mice immunised orally with mini-bead compositions of the invention designated "LEDDS" in the legend and with comparative solutions, as described in Example 8.

The acronym "LEDDS" as used herein means "Liquid Emulsion Drug Delivery System" and designates mini-beads of the invention. (Whilst the mini-beads of the invention may themselves be considered to be solidified emulsions, it will be appreciated that it is believed—without being bound by theory—that drug delivery in the body involves a liquid emulsion). Thus the term "LEDDS" featured in FIGS. 1 and 2 refers to mini-beads of the disclosure.

"Antigen" is herein defined as a compound which, when introduced into a non-human animal or a human, will result in the formation of antibodies against the antigen and cell-mediated immunity.

"Adjuvant" is herein defined as a compound or compounds that, when used in combination with an antigen, augment or otherwise alter or modify the resultant immune responses generally in a non-antigen-specific way.

Some active principles can act as both antigen and adjuvant. An example is cholera toxin and its derivatives. Bearing this in mind, while the above definitions are generally adhered to, the context in which these words are employed is the ultimate guide to construction. Antigens and adjuvants together or individually may be referred to as "(an) active ingredient(s)". Any mention hereunder of an active ingredient also includes a derivative thereof.

It is to be further appreciated that the present invention may be used to deliver a number of vaccines, antigens or adjuvants or other component, singly or in various combinations. The term "antigen" or "adjuvant" used herein includes but is not limited to peptides or proteins (and mimetics as well as covalent, non-covalent or chemical analogues thereof), nucleic acid e.g. DNA, RNA or DNA/RNA molecules or derivatives (eg methylated derivatives) to support gene or other nucleic acid-based vaccines and entities leading to various immunotherapies, including antigenic and nucleic acid-based vaccines or immunotherapies, primers and adjuvants of such as well as organisms that synthesize and secrete therapeutic or health modulating entities.

Suitable classes of therapeutic agents which can be delivered using this invention include but are not limited to peptides, proteins, vaccines, and oligonucleotides, including non-covalent or covalent modified versions thereof.

Moreover, the active principle(s), i.e. immunomodulator(s), included in the composition of the invention may be in a solubility-modified form so that when released in the colon or other target part of the GI tract, it (they) is (are) more or less readily absorbed (depending on the extent to which absorption is or is not desired).

It is not essential that all the active principles be solubilized in the composition of the invention. Complete, partial or no solubilisation are all possible according to the formulator's objectives.

As noted above, the active principle(s) may be a small molecule, a macromolecule or biopharmaceutical and includes any variant, derivative or conjugate designed to enhance immunogenicity, permeability, increase lipophilicity, and/or increase hydrophilicity or the like (or counterintuitively to reduce immunogenicity and increase stability in the case of a biopharmaceutical such as a peptide, protein, nucleic acid or carbohydrate where non-specific adjuvant effect only is desired).

"Vaccine" is herein defined as a composition comprising an antigenic substance, in particular comprising modified-live (live attenuated) or inactivated infectious agent, or some part (subunit) of an infectious agent (subunit vaccine), that is administered, most often with an adjuvant, into an animal to produce an immunologically mediated effect such as active immunity, induction of tolerance, breaking of tolerance, altering the course of an auto-immune disease etc. The composition of the invention is variously described herein as a vaccine composition or an immunomodulating composition. Unless the context so demands, the term "vaccine composition" includes immunomodulation which is not necessarily vaccination e.g. toleration or other immunotherapy.

Mucous membranes include those of the oral cavity (buccal, sublingual), nose (nasal), gut (intestinal), rectum (rectal), or vagina (vaginal). Other mucous surfaces suitable for application of the compositions of the present invention may include ocular (corneal, conjunctival) routes of administration.

The vaccine composition of the invention may be delivered to a mucosal surface by direct application, ingestion through the oral cavity, insertion, injection, and through other conventional means known in the art. When administered in a food or beverage carrier, the adjuvant/vaccine composition of this invention is generally included in the carrier composition in a concentration ranging from about 0.0001-10% by weight/volume (w/v) in case of a beverage carrier and weight/weight (w/w) in case of a food carrier, with about 0.01-1.0% w/v or w/w respectively, being preferred.

The vaccine composition of the invention may be administered in conventional solid dosage forms, such as in tablets, capsules, granules, troches, and vaginal or rectal suppositories (pessaries).

If not otherwise stated, ingredients, components, excipients etc of the composition of the invention are suitable for the intended purposes of immunomodulation e.g. vaccination (ie. pharmaceutically acceptable) discussed elsewhere herein in more detail.

The active principle(s) may be incorporated and/or may reside in the aqueous phase and/or the oil phase of the composition of the invention.

Antigens

The antigen for use in this invention may be any desired antigen falling within the definition set forth above. Antigens are commercially available or one of skill in the art is capable of producing them. The one or more antigenic moieties comprised in the vaccine can be, for example, either a modified-live or killed microorganism (eg chemically or heat-killed); or a natural product purified from a microorganism or other cell including, but not limited to, tumor cells; a synthetic product; a genetically engineered protein, peptide, polysaccharide or similar product; or an allergen, an antibody or fragment thereof. The antigenic moiety can also be a subunit of a protein, peptide, polysaccharide, antibody or similar product optionally conjugated, admixed or associated with another similar or different molecular entity. The antigen may also be a nucleic acid e.g. DNA or RNA that engenders an immune response directly or indirectly or which interferes with or affects mediation of an immune response. For example, the nucleic acid may encode a protein antigen.

Representative antigens that can be used according to the present invention include, but are not limited to, natural, recombinant or synthetic products derived from viruses, bacteria, fungi, parasites and other infectious agents including prions. Examples of antigens also include human antigens which it might be desirable to use in prophylactic or therapeutic vaccines e.g. which are involved in or relevant to autoimmune diseases, in particular autoantigens; hormones;

tumour antigens; and allergens. The microbial (eg viral or bacterial) products can be components which the organism produces or can be induced to produce e.g. by enzymatic cleavage or can be components of the organism that were produced by recombinant DNA techniques that are well known to those of ordinary skill in the art.

The antigenic materials may for example be derived from or based on an infectious agent selected from the following infectious agents: *Helicobacter pylori*, *Vibrio cholerae*, enterotoxigenic *Escherichia coli* (ETEC), *Shigella* spp., *Clostridium difficile*, rotaviruses and calici viruses; or causative agents of respiratory infections including those caused by *Mycoplasma pneumoniae*, influenza virus, and respiratory syncytial virus; and causative agents of sexually transmitted genital infections including those caused by HIV, *Chlamydia trachomatis*, *Neisseria gonorrhoeae* and herpes simplex virus. Other infectious agents from which antigenic materials may be drawn include *Streptococcus* spp and *Staphylococcus* spp e.g. *S. aureus*. A further infectious agent from which antigenic materials may be drawn include the poliomyelitis virus (polio).

The composition of the invention may be a vaccine for example to prevent, treat or delay the progression of disease caused directly or indirectly or exacerbated by an infectious, infecting or other such agent including but not limited to those enumerated in the above list. The invention, in certain embodiments also provides a means of treating and/or preventing or delaying the progression of such disease.

Adjuvants

In certain embodiments, the composition of the invention itself has adjuvant properties. However, whether or not such embodiments are chosen, the composition may include adjuvants such as, but not limited to, saponins, fractions of saponins, synthesized components of saponins, ISCOMS, muramyl dipeptide and analogues, pluronic polyols, trehalose dimycolate, amine containing compounds, cytokines and lipopolysaccharide derivatives, for example. Adjuvants may be chosen for example from the ceramides (eg α-galactosylceramide also known as alphaGalCer), chitosan, cholera toxin e.g. rCTB (recombinant B subunit of cholera toxin), *E. coli* heat labile enterotoxin e.g. mLT, oligonucleotides e.g. oligodeoxynucleotides such as CpG (cytosine phosphate guanine) and ODN1a (deoxy-inosine/deoxycytosine) whether or not derivatised, monophospholipid (MPL) e.g. MPLA, BCG, saponins including those derived from the soap bark tree (*Quillaja saponaria*) such as QS21 and QuilA, Poly I:C (polyinosinic:polycytidylic acid or polyinosinic-polycytidylic acid sodium salt), etc. Derivatives of all the preceding substances are also included whether or not derivatives are mentioned in a specific context. Substances identified here as adjuvants may have or play other roles in the invention or may play more than one role simultaneously. For example, rCTB may also, in certain embodiments, play the role of an antigen.

Thus adjuvants for use in the invention may also be chosen from derivatives of any of the foregoing adjuvants or adjuvant types. Adjuvants also include marine derivatives, sponges etc and their derivatives. In general, toll-like receptor ligands may be included as adjuvants and include LPS, lipoproteins, lipopeptides, flagellin, double-stranded RNA, unmethylated CpG islands and various other forms of DNA and RNA classically released by bacteria and viruses. TLR3 and TLR9 ligands are preferred in one embodiment. Substances which bind to the CD1d protein on antigen-presenting cells are particularly contemplated as are mistletoe extracts, particularly detoxified mistletoe extracts. Other adjuvants contemplated include the Nod-like receptor (NLR) ligands described by Wagner et al in PLoS ONE, April 2009, Vol 4, Issue 4, the entirety of which is incorporated herein by reference. Muramyl dipeptide is also envisaged as is KLKL5KLK described by Li et al in DNA and Cell Biology, Vol 27, No. 8, 2008 the entirety of which is incorporated herein by reference. Also contemplated is KLKL5KLK in combination with ODN1a as described by Schellack et al in Vaccine 24 (2006) 5461-5472, the entirety of which is incorporate herein by reference.

Preferred adjuvants include the ceramides and other lipid molecules (especially non-ionic lipid molecules) which specifically stimulate natural killer T (NTK) cells. A ceramide is composed of sphingosine and a fatty acid and are found in high concentrations within the cell membrane of cells being one of the component lipids that make up sphingomyelin, one of the major lipids in the lipid bilayer. Ceramide can act as a signaling molecule eg. regulating the differentiation, proliferation, programmed cell death (PCD), and apoptosis (Type I PCD) of cells. Preferred ceramides include alpha-galactosylceramides including agelasphins and derivatives. A particularly preferred alpha-galactosylceramide is the product known as KRN7000 commercially available from Funakoshi, Japan, and originally synthesised by Kirin Pharmaceuticals, Japan. Derivatives of KRN7000 are also contemplated as components of the composition of the invention and are described in detail by Dere et al (2008) in Organic Letters, Vol 10, no. 20, pp 4641-4644, the entirety of which is incorporated herein by reference. The thiolated derivative of alpha-galactosylceramide (in which the glycosidic oxygen atom has been replaced by a sulphur atom) described by Dere et al is particularly preferred as are racemates, enantiomers or distereoisomers thereof and of closely related derivatives.

In one embodiment, the inclusion in the composition of the invention of more than one adjuvant may aid in the stimulation of a mucosal immune response.

Adjuvants may be present in a concentration of up to about 5% by weight of the composition, with less than about 1% by dry weight being preferred and less than 0.1% being more preferred.

Other Active Components

The heading of this section is for convenience only and does not imply strict categorisation. For example, a category, substance or active principle described within this "other active components" section may also be considered to fall within another section or category in this patent specification. The word "excipient" is sometimes used herein to denote "another active component" bearing in mind that some excipients can be active and that some active principles can have excipient character. It is also contemplated that certain substances described in this section and elsewhere herein may play dual roles e.g. be both a bioadhesive and an adjuvant. It is also contemplated that substances described in this section may be incorporated and/or may reside in the aqueous phase and/or the oil phase of the composition of the invention.

In general terms, the invention foresees incorporation into the composition of one or more of the following substances or categories of substances in addition to the one or more primary active principles (immunomodulator(s), particularly antigen and/or adjuvant). For example, the composition may contain a protectant such as a proteolytic enzyme inhibitor; an adhesive entity such as a muco- or bio-adhesive; and adsorption enhancer; a probiotic; excipients to maximize solubility of vaccine component(s); excipients to maximize permeability and/or absorption of the vaccine component(s)

in the small intestine, ileum or colon especially in relation to immune competent cells such as M cells and/or Peyer's patches.

The antigen-containing composition of the invention may comprise one or more agents to enhance adsorption of antigen onto, and absorption by, mucosal surfaces, such as lecithin. Thus vaccine compositions of the invention may comprise one or more agents to enhance such vaccine antigen adsorption and absorption. The lecithin may be lecithin lipoidal material, such as phosphatidylcholine, that can be used to form liposomes. Phospholipids, lysophospholipids, glycolipids and neutral lipids comprise the typical composition of lecithin. Lecithins are molecules that, when completely hydrolyzed, yield two molecules of fatty acid, and one molecule each of glycerol, phosphoric acid, and a basic nitrogenous compound, which is usually choline. The fatty acids obtained from lecithins on hydrolysis are usually, but not limited to, oleic, palmitic, and stearic acids. The phosphoric acid may be attached to the glycerol in either an a- or the 3-position, forming a-glycerophosphoric acid or (3-glycerophosphoric acid, respectively, and producing the corresponding series of lecithins which are known as a- and 3-lecithins.

Commercial lecithin is obtained by extraction processes from egg yolk, brain tissue, or soybeans. Ovolecithin (vitelin) from eggs and vegilecithin from soybeans, as well as purified lecithin from calf's brains have been used as emulsifiers, antioxidants, and stabilizers in foods and pharmaceutical preparations. Commercial lecithin may be obtained from a variety of sources, for example Central Soya (Fort Wayne, Ind.). One of ordinary skill in the art would be able to determine an appropriate lecithin for a desired application.

The invention may also include cationic phospholipids such as 1,2-di-(9Z-octadecenoyl)-3-trimethylammonium-propane (chloride salt) also known as DOTAP.

The invention may also include one or more pro-biotics. Probiotics are bacteria or microorganisms that are beneficial to the health of the individual or animal. Examples of commonly used probiotics include, but are not limited to, various beneficial strains of *Lactobacillus, Bifidobacterium, Streptococcus*, etc. If present, each of the organisms should be administered in a concentration ranging from about 103 to 10 s CPU each. Such pro-biotics may be genetically engineered to express certain antigens against which it is desirable to elicit an immune response in an animal. Examples of such antigens and/or of organisms from which such antigens may be drawn, are enumerated above. Well known techniques of molecular biology can be used to introduce such exogenous genes into probiotic microorganisms.

A concentration of an attenuated viral vaccine will comprise about 103 to 109 TCID50 per animal. Preferable the amount will be from about 104 to 107 TCID50 per animal. The concentration of killed antigen or subunit antigen may range from nanogram to milligram quantities of antigen with about 1 microgram to 1 milligram preferred.

Regarding permeability enhancement, possible excipients include but are not limited to medium chain triglycerides (MCTs) such as C8-C20, sodium caprate, sodium dodecanoate, sodium palmitate, SNAC, chitosan and derivatives thereof, fatty acids, fatty acid esters, polyethers, bile salts, hydroxylase inhibitors, antioxidants (eg ascorbic citric, fumaric and other acids) and/or nitric oxide donors, including nitric oxide donor groups covalently attached to various active pharmaceutical ingredients. The preceding list is of particular interest to enhance permeability in the ileum e.g. when an immune response is mediated by immune competent cells in that portion of the GI tract.

To enhance permeability in the colon, typical excipients including, but not limited to sodium caprate, sodium dodecanoate, sodium palmitate, SNAC, chitosan and derivatives thereof, fatty acids, fatty acid esters, polyethers, bile salts, hydroxylase inhibitors, antioxidants and/or nitric oxide donors, including nitric oxide donor groups covalently attached to various active pharmaceutical ingredients. Such excipients are relevant when an immune response is desired in the colon or when the vaccine composition of the invention is combined with a non-vaccine active principle.

The composition may further comprise excipients to enhance the therapeutic potential of active principles for immunomodulation or other active pharmaceutical agents in the ileum and colon including, but not limited to absorption limiters, essential oils such as omega 3 oils, natural plant extracts such as neem, ion-exchange resins, bacteria degradable conjugation linkers such as azo bonds, polysaccharides such as amylose, guar gum, pectin, chitosan, inulin, cyclodextrins, chondroitin sulphate, dextrans, guar gum and locust bean gum, nuclear factor kappa B inhibitors, acids such as fumeric acid, citric acid and others, as well as modifications thereof.

The composition may further comprise excipients or other active pharmaceutical or other ingredients to enhance systemic bioavailability following absorption in the small intestine including efflux pump inhibitors, including, but not limited to PgP pump inhibitors, and metabolism inhibitors, including, but not limited to, cytochrome P450 3A inhibitors.

The composition may further comprise excipients to reduce any systemic side effects associated with absorption in the small intestine including, but not limited to, antioxidants, such as curcuminoids, flavanoids or more specifically including curcumin, beta-carotene, α-tocopherol, ascorbate or lazaroid.

The composition may further or separately comprise antioxidants (such as ascorbic citric, fumaric and other acids) taste-masking or photosensitive components or photoprotective components. Such acid components may instead or additionally act as retardants of dissolution when used in combination with polymers which dissolve in aqueous media only above a certain pH threshold e.g. HPMC derivatives described elsewhere herein.

The composition may further or separately include an adhesive to ensure that if desired eg. for the mini-bead embodiment, that the mini-beads remain, or remain for longer, in the gastric environment. Mini-beads according to the invention may also comprise materials facilitating or enabling floating or density reduction e.g. as a means of localising mini-beads in desired GI sites. The invention may also, in the mini-bead embodiment, have the means to swell and/or aggregate in the stomach or other GI site.

One embodiment to further enhance delivery of the vaccine composition according to the invention into and/or across the intestinal epithelial barrier comprises inclusion of receptor site targeting means ie. means to target receptor sites of the intestine such as M cells.

M cells are professional antigen sampling cells that are found in the epithelium of the gut-associated lymphoid tissue or Peyer's patch and play an important role in sampling foreign materials, particulates, and antigens from the lumen of the GIT (gastro-intestinal tract), resulting in downstream mucosal immune responses. "Targeting means" includes means to target M cells including the transcytotic capacity of M cells. An embodiment in which the composition is so targeted also has the advantage of prolonging residence time in the GIT so producing a high local concentration of vaccine at the epithelial cell surface and promoting absorption to the underlying lymphoid tissue. Examples of such targeting means according to the invention are small organic mimetics of the glycoprotein UEA-1 lectin (see e.g. Higgins et al Pharmaceutical Research, Vol 21, No 4, 2004, the entirety of which is incorporated herein by reference). The mimetics may be incorporated with the aqueous or oil phase of the composition of the invention and/or may be adsorbed on to the surface of the mini-beads or included in the coating if one is present. Alternatively, the mimetics may be incorporated into (eg dispersed or dissolved in) the aqueous or oil phase of the mini-bead e.g. without presence in the coating. Another approach is to conjugate with streptavidin/biotinylated linkers as is known in the art and described in Higgins et al. Other targeting means include other molecular entities which target M cells including the GM1 receptor (the receptor for the B subunit of cholera toxin), the sialyl Lewis A antigen, reovirus antigens and ligands for the IgA receptor. A further example is the *Aleuria aurantia* lectin (AAL), a fucose-binding lectin from the fruiting bodies of the edible "orange peel fungus" as described by Roth-Walter et al in Vaccine, Vol. 23, 2005, the entirety of which is incorporated herein by reference. AAL may be incorporated into the composition of the invention as just described for other targeting means. Alternatively surface active groups, if any, of the matrix or coating, may be activated to couple to AAL e.g. by using carbodiimide/N-hydroxysuccinimide as described by Roth-Walter et al. Other such targeting means include components of mammalian (including human) milk protein e.g. lactadherin or other integrin-like molecules and/or which target dendritic cells. Such proteins may include those found in human post-natal milk. Dendritic-cell targeting substances are also contemplated as means of targeting intestine receptor sites.

In one embodiment the aqueous phase may contain a disintegrant where it is particularly desired to enhance the rate of disintegration of the composition of the invention. Examples of disintegrants which may be included are alginic acid, croscarmellose sodium, crospovidone, low-substituted hydroxypropyl cellulose and sodium starch glycolate.

A crystalisation inhibitor (eg approximately 1% by dry weight of the composition) may also be included in the composition of the invention, preferably in the aqueous phase. An example is hydroxy propyl/methyl cellulose (HMC or HPMC, hypromellose etc) which may play other roles such as emulsifier (see above) or to delay dissolution (see below).

The aqueous phase may also include one of the polymers described below in the section on coatings. Such inclusion may be in a composition with or without a coating. In one embodiment without a coating, such polymer may be incorporated into the body of the composition of the invention e.g. dispersed or dissolved in the aqueous phase. In this embodiment, it is preferred to select one or more derivatives of hydroxypropyl methylcellulose (HPMC) as these polymers exhibit pH dependent solubility and may therefore be included within the matrix to delay dissolution instead of or in addition to a coating. It is desirable to include a polymer which dissolves at a pH higher than stomach pH. Especially preferred examples include hydroxypropyl methylcellulose phthalate (HPMCP), which rapidly dissolves in the upper intestinal tract below (distal to) the stomach and hydroxypropyl methylcellulose acetate succinate (HPMCAS) in which the presence of ionizable carboxyl groups causes the polymer to solubilize at high pH (>5.5 for the LF grade and >6.8 for the HF grade). These polymers are commercially available from Shin-Etsu Chemical Co. Ltd.

The aqueous phase may therefore include an enteric polymer (the term "enteric polymer" is a term of the art referring to a polymer which is preferentially soluble in the less acid environment of the intestine relative to the more acid environment of the stomach). An enteric polymer may for example be any known enteric polymer, for example HPMCP, cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer.

The aqueous phase may also comprise a base such as sodium bicarbonate ($NaHCO_3$) or sodium hydroxide (NaOH) or a mixture of more than one such base. In this embodiment, the base or bases is/are present in an amount up to 10% by dry weight of the composition, preferably up to 5%, more preferably around 1%. Such bases may optimally be included in the aqueous phase. In particular, the aqueous phase may contain a base where an enteric material (e.g. enteric polymer, for example HPMCP) is to be dissolved in the aqueous phase, since such polymers dissolve only at alkaline pH. As an alternative to dissolving an enteric material in the aqueous phase, one (or more than one) may provided in the polymer matrix and/or be comprised in a coating.

The aqueous phase may include one or more active principles as discussed in more detail elsewhere herein particularly in the section entitled "Active Ingredients" et seq. Such active principles may be introduced in manufacture (see below) in either the oil phase or the aqueous phase. They may be dissolved in the aqueous phase or in the oil phase or both independently of the phase in which they were introduced during manufacture.

Where this specification does not indicate where an active component or other entity is located (the oil phase, the matrix phase or a coating) then the disclosure is not restricted as to the location of incorporation and all possibilities are embraced. The reader will recall in this regard that distributions described herein of constituents between the oil and matrix phases in the solidified composition is deduced from the manufacturing process and lipophilicity/hydrophilicity of the constituents, rather than the result of observation.

Immune Modulation

Innate immune response cells such as dendritic cells (DCs) engulf pathogens through a process called phagocytosis. DCs then migrate to the lymph nodes where T cells (adaptive immune cells) wait for signals to trigger their activation. In the lymph nodes, DCs "mince" the engulfed pathogen and then express the pathogen "clippings" as antigen on their cell surface by coupling them to a special receptor known as a major histocompatibility complex (MHC). T cells can then recognize these clippings and undergo a cellular transformation resulting in their own activation. Gamma-delta T cells possess characteristics of both the innate and adaptive immune responses. Macrophages can also activate T cells in a similar approach. Among other things, the composition of the invention, in at least some embodiments, provides a means of delivering active principles to the lymphatic system.

In various embodiments, the vaccine composition of this invention serves at least one of, and suitably all of, the following multiple functions when it is delivered orally 1) it protects the vaccine antigen from degradation by the stomach acid and digestive enzymes; 2) transports the antigen to the mucosal surfaces (especially GALT); 3) facilitates adsorption of the antigen onto the mucosal surfaces; 4) enhances absorption of the antigen; and 5) enhances the immune response to the antigen due to the adjuvant properties of the composition. In the case of delivery to nasal, oral cavity, vaginal and rectal mucosa, the composition of the invention functions as a system to deliver and adsorb the antigen to the mucosal surface. Once adsorbed onto the mucosal surface and absorbed, an immune response is engendered.

The combination of aspects and components in this invention unexpectedly enables an improved vaccine delivery system for vaccine antigens. The current invention enables a more simple and efficient method of incorporation of antigen into a delivery system with no, or minimal damage, to vaccine epitopes. The vaccine formulation can be done at low cost and can be easily commercialized as a feed or water additive or as an oral paste or tablet.

In some embodiments, the invention enables the translocation of antigens to the lymph nodes where they can be recognized by T cells following contact with relevant mucosa e.g. after oral administration. In other embodiments, the invention provides physical protection to antigens which grants the antigen a prolonged delivery. This means that the organism will be exposed to the antigen for a longer duration, making the immune system more robust as it makes use of the additional time by upregulating the production of B and T cells needed for greater immunological memory in the adaptive immune response. In another embodiment, the invention increases the capacity to cause local reactions at the site of contact with immunological mucosa such as GALT. In another embodiment, the invention induces the release of inflammatory cytokines which helps to not only recruit B and T cells at sites of infection but also to increase transcriptional events leading to a net increase of immune cells as a whole. In another embodiment, the invention increases the innate immune response to antigen by interacting with pattern recognition receptors (PRRs), specifically Toll-like receptors (TLRs), on accessory cells.

In another embodiment, the invention provides prime-boost immunizations (including a method for immunizing an animal, e.g. humans) wherein the priming vaccine is unmatched with the boosting vaccine, ie. following a 'heterologous' prime-boost format and using the same or different antigens in the booster vaccination as in the priming vaccination. Either the priming or (one of the) booster dose(s) may be a composition according to the invention. In more specific embodiments, the invention includes heterologous prime-boost vaccinations including DNA priming followed by boosting with recombinant protein, inactivated vaccine, viral vectors, BCG or recombinant modified vaccinia Ankara virus (MVA); priming with viral vector followed by boosting with recombinant protein; and priming with BCG followed by boosting with viral vector; wherein a composition according to the invention is used for at least one of the priming or boosting immunisations. In one embodiment, the invention is a composition for use in eliciting an immunological profile (and/or an immunological response having a particular profile) in an animal as described above or elsewhere herein. In a related embodiment, the invention provides an oral boost immunisation after a non-oral (eg intravenous) priming immunization comprising administering a composition according to the invention to an animal e.g. man which has already received a priming immunization.

The invention also relates to a method of enhancing the IgG1 and/or IgG2A response in an animal comprising administering a composition according to the invention to the animal with or without prior priming immunization.

The invention also relates to a method of switching the immune response away from (and/or switching off) a TH1-type immune response in an animal comprising administering a composition according to the invention to the animal with or without prior priming immunization. A reciprocal method may also be used ie. switching the immune response towards (and/or switching on) a TH1-type response. The invention also relates to a method of switching the immune response away from (and/or switching off) a TH2-type immune response in an animal comprising administering a composition according to the invention to the animal with or without prior priming immunization. A reciprocal method may also be used ie. switching the immune response towards (and/or switching on) a TH2-type response.

In a preferred embodiment, the composition of the invention includes a component for lymphatic targeting and/or lymphatic delivery in order to further enhance the immune response and optionally to reduce the extent of hepatic clearance. In another preferred embodiment, the composition of the invention may be used to prevent or slow metastasis or other immunotherapy intended to treat or slow the progression of malignancy e.g. solid or haematological malignancies.

In another embodiment of the invention, (one of) the active principle(s) is a transcription factor (or derivative thereof) e.g. transcription factor Bcl6 which is able to bind to DNA and cause the expression of other genes to cause T helper cells to develop to produce B cells and antibodies. In a variant embodiment, the composition comprises a substance which stimulates the production (eg in vivo) of transcription factor Bcl6. The invention also comprises an embodiment in which the composition includes a Blimp1 or related protein or derivative (or other antagonist of Bcl6) which binds to Bcl6 and prevents it from binding to DNA.—preventing Bcl6 from binding to DNA prevents maturation of TFH cells, leaving B cells unable to make antibodies (using such a composition according to the invention involves a method of treating certain diseases such as autoimmune disease e.g. rheumatoid arthritis which are triggered by antibody-induced inflammation). Thus compositions of the invention which incorporate such transcription factors, stimulants of transcription factor expression and/or antagonists thereof may be used for enhancing vaccines or conversely blocking autoantibody responses.

In a further application of the invention, the induction of production of antibodies and T-cells is contemplated. In addition it is contemplated that the invention includes compositions which comprise e.g. antibodies or other active agent which bind(s) to e.g cancer cells, and also at least one other active agent which attracts and binds T-cells. Such a composition has utility e.g. in the killing of cancer cells. The invention also contemplates inclusion of an antigen against a certain epitope and an antigen again a T-cell marker such that the resulting composition acts in situ e.g. in vivo as a bi-functional antibody (similar to antibodies made from the small binding domains by which antibodies recognize their antigens on T cells or target cells, all such domains being linked together on one polypeptide chain). For example such a bi-functional antibody may have two specific binding sites, one of which attaches to e.g. the CD3 antigen on T cells and the other of which binds to a surface antigen e.g. on tumour cells. One embodiment of the composition of the invention acts as a functional equivalent to such a bi-functional antibody.

The invention in one embodiment also relates to a method of enhancing local antigen-specific IgA response and/or systemic T cell response in an animal comprising administering to the animal a composition as described herein.

Oral Tolerance

In one embodiment, the present invention provides means to exploit the phenomenon of oral tolerance (described in the section above on prior art) in treating oral autoimmune or inflammatory diseases. Thus, in certain embodiments the invention permits oral delivery of antigens to be modulated in relation to the following characteristics antigen dose, the nature of the antigen, the innate immune system, the genetic background and immunological status of the host, and mucosal adjuvants described in more detail elsewhere herein. In a specific embodiment, the invention provides targeted delivery to specific regions of the intestinal tract to induce or break oral tolerance. In particular the invention provides a means (eg a composition) able to release vaccine active components, e.g. following oral administration, to the rectum/colon where a mix and/or a concentration (especially relative to other sections of the GIT) of immune inductive (organised lymphoid tissues) and effector sites (diffuse lamina propria) are located as described in the section above on prior art. In addition the invention provides a composition which prevents or reduces normal ingestion of (eg food) peptides and proteins such that when such components reach the colon they activate an appropriate, desirable, tolerising or therapeutic immune response e.g. in naïve $CD4^+$ T cells present in such locations.

The composition of the invention may therefore be utilised in the generation of active cellular suppression or clonal anergy by modulating the dose of antigen fed orally and/or avoidance of loss of tolerance through increased antigen dose. The invention also provides means of enhancing oral tolerance by feeding to an affected person the composition of the invention comprising immune adjuvants such as lipopolysaccharide or cholera toxin subunit B, in order to stimulate certain populations of cells to down-regulate immune responses. The composition of the invention may for example be used in the treatment of T-cell mediated autoimmune disorders. Autoimmune diseases which may be treated using compositions according to the invention include multiple sclerosis, rheumatoid arthritis, colitis (including Th1-mediated colitis), Crohn's disease, stroke, Alzheimer's disease, atherosclerosis and type 1 diabetes. The invention also permits tolerance induction to be used to prevent antibodies being raised against peptide, protein and antibody therapeutics (biological pharmaceuticals or "biologicals") by administering a tolerising amount of such therapeutic in a composition according to the invention to an animal e.g. man on one or more occasions before such biological pharmaceutical is administered.

Compositions for use in inducing oral tolerance may contain an antigen selected from (i) antigens involved in an autoimmune or other disease and (ii) biological therapeutics. Examples of antigens and their associated diseases are:
Arthritis: type II collagen
Autoimmune uveitis: S-antigens
Autoimmune myasthenia gravis: Torpedo acetyl-choline receptor
Insulin-dependent diabetes mellitus: insulin
Transplantation rejection: allogenic cells/allopeptides
Allergies: dietary specific peptides/proteins/antigens
Thyroiditis: thyroglobulin
Celiac: tissue transglutaminase/gliadin/HLA-DQ218
Multiple sclerosis: copolymer I/myelin antigens.

The invention includes the use of disease- or allergenic-specific peptides in the presence or absence of immunomodulatory agents to induce appropriate immune effects. Thus, composition of the invention may comprise a disease- or allergenic-specific peptide, and additionally in some embodiments include one or more further immunomodulatory agents (e.g. selected from immunosuppressants and adjuvants and optionally others) whilst in other embodiments the composition contains no additional immunomodulatory agents.

The composition of the invention may be utilized in order to bring antigen into contact with the gut-associated lymphoid tissue (GALT) either directly or after absorption. The composition of the invention is intended, in one embodiment, to allow antigens and/or adjuvants to interact with or facilitate their interaction with T cells in the GALT. In one embodiment, the section of the GI tract where this interaction occurs is the rectum and/or colon. In another embodiment, the section is the jejunum or other site having almost no immune inductive sites.

The present invention provides compositions and/or formulations comprising the necessary antigenic peptides (including any covalently or non-covalently modified peptides) to be formulated, with or without adjuvants and optionally other ingredients as described elsewhere herein. Such other ingredients e.g. permeability enhancers, along with the composition of the invention being optionally encapsulated (eg coated) with a single or multiple layer(s) of (for example) a polymer, with the layers or polymer coatings being modified permit release of the active components at the most appropriate location along the intestine or colon/rectum. In addition to the auto-immune and other diseases mentioned above and in the section describing the prior art, the current invention also provides, in some embodiments formulations for use in treating and/or preventing such diseases as celiac disease, food allergies and general allergies.

In particular the invention provides a composition wherein the active components or principles modulate oral tolerance and may include additional components to modulate oral tolerance. Such additional components may be gluten or a gluten derivative.

Methods of inducing oral tolerance may include delivering an antigen (a single antigen or a plurality of antigens) in the lower GI tract, for example in the colon and/or rectum. The aim of the method is to deliver the antigen intact (i.e. without significant degradation). Additionally or alternatively, oral tolerance may be induced by including both an antigen and an immunosuppressant, for example a cyclosporin, in the composition such that when the antigen is exposed to the mucosal intestinal cells they are in a more naïve state and therefore will permit the induction of tolerance rather than a vaccine/immune boosting reaction.

Accordingly, the invention includes a method of inducing oral tolerance in a mammal, e.g. a human, comprising:
  administering to the mammal an antigen-containing composition of the disclosure which is adapted to release the antigen in the colon or rectum; and/or
  administering to the mammal an antigen-containing composition of the disclosure which further comprises a cyclosporin or another immunosuppressant.

As adaptations for release in the colon or rectum may be mentioned by way of example:

formulating the composition as a suppository
formulating the composition for oral administration and including release-controlling agents.

As examples of release-controlling agents, the composition may comprise a polymer which is degraded by bacterial enzymes in the colon or which otherwise acts as a barrier until the composition reaches the colon (e.g. which is dissolved or degraded in the conditions of the colon), Retardant polymers which are degraded or eroded during passage down the GI tract may be used and/or pH-independent polymers comprising pore-formers which are dissolved or degraded in the conditions of the colon. The composition may include an enteric polymer to prevent degradation in the stomach such that the composition is exposed to further dissolution, erosion or degradation only when it has entered the intestine. Polymers mentioned in this paragraph may be included in the matrix and/or may form or be comprised in one or more coatings.

In the case of compositions containing immunosuppressants, the invention is not limited as to the identity or release site(s) of the immunosuppressant. In some embodiments, the immunosuppressant is released in the intestine and optionally at one or more other sites in the GI tract (e.g. the colon). In other embodiments, the immunosuppressant is released in the colon and optionally at one or more other sites in the GI tract (e.g. the intestine).

Where an immunosuppressant is used, it may be a cyclosporin. Cyclosporins form a class of polypeptides commonly possessing immunosuppressive and anti-inflammatory activity. The most commonly known cyclosporin is cyclosporin A (International Non-Proprietary Name ciclosporin A). Other forms of cyclosporins include cyclosporin B, C, D, and G and their derivatives. It should be understood that herein the terms "cyclosporin" or "cyclosporins" refers as used herein to any of the several cyclosporins derivatives or prodrugs thereof, or to any mixture of any of the above. Cyclosporins may be incorporated in compositions of the invention by including them in the oil phase during manufacture.

Other immunosuppressants useful in the invention are, amongst others, tacrolimus, gancyclovir, etanercept, rapamycin, cyclophosphamide, azathioprine, mycophenolate mofetil, methotrexate, cortisol, aldosterone, dexamethasone, a cyclooxygenase inhibitor, a 5-lipoxygenase inhibitor, and leukotriene receptor antagonist. Immunosuppressants may be incorporated in compositions of the invention by including them in the oil phase and/or aqueous phase during manufacture. The choice of phase may in practice depend on the immunosuppressant's solubilities in the respective phases.

It will therefore be understood that, whilst cyclosporin A is a preferred immunosuppressant, other immunomodulating/suppressing entities, for example methotrexate may be used to control immune cells, mainly dendritic cells, maintaining or pushing them towards being immature or naïve which is preferential for the induction of mucosal tolerance.

Also included in the disclosure are preparations selected from the compositions, minibead populations and products of the disclosure, wherein the preparation comprises an antigen and: (i) the preparation is adapted to release the antigen in the colon or rectum; and/or (ii) the preparation further comprises a cyclosporin or another immunosuppressant. Such preparations may be for inducing oral tolerance. The disclosures herein relating to oral tolerance apply mutatis mutandis to the preparations mentioned in this paragraph. The invention includes methods of inducing oral tolerance in a mammal, comprising administering to the mammal a preparation as described in this paragraph.

Surfactants

In the description and claims of this specification, the term "surfactant" is employed as a contraction for "surface active agent". For the purposes of this description and claims, it is assumed that there are four major classifications of surfactants: anionic, cationic, nonionic, and amphoteric (zwitterionic). The nonionic surfactant remains whole, has no charge in aqueous solutions, and does not dissociate into positive and negative ions. Anionic surfactants are water-soluble, have a negative charge and dissociate into positive and negative ions when placed in water. Cationic surfactants have a positive charge, and also dissociate into positive and negative ions when placed in water. The amphoteric (zwitterionic) surfactant assumes a positive charge in acidic solutions and performs as a cationic surfactant, or it assumes a negative charge in an alkaline solution and acts as an anionic surfactant.

Surfactants can also be classified according to their hydrophilic-lipophilic balance (HLB) which is a measure of the degree to which the surfactant is hydrophilic or lipophilic, determined by calculating values for the different regions of the molecule, as described (originally for non-ionic surfactants) by Griffin in 1949 and 1954 and later by Davies. The methods apply a formula to the molecular weight of the whole molecule and of the hydrophilic and lipophilic portions to give an arbitrary (semi-empirical) scale up to 40 although the usual range is between 0 and 20. An HLB value of 0 corresponds to a completely hydrophobic molecule, and a value of 20 would correspond to a molecule made up completely of hydrophilic components. The HLB value can be used to predict the surfactant properties of a molecule:

| HLB Value | Expected properties |
| --- | --- |
| 0 to 3 | antifoaming agent |
| from 4 to 6 | W/O emulsifier |
| from 7 to 9 | wetting agent |
| from 8 to 18 | an O/W emulsifier |
| from 13 to 15 | typical of detergents |
| 10 to 18 | solubiliser or hydrotrope |

Although HLB numbers are assigned to surfactants other than the non-ionic, for which the system was invented, HLB numbers for anionic, cationic, nonionic, and amphoteric (zwitterionic) surfactants can have less significance and often represent a relative or comparative number and not the result of a mathematical calculation. This is why it is possible to have surfactants above the "maximum" of 20. HLB numbers can however be useful to describe the HLB requirement of a desired application for a given emulsion system in order to achieve good performance.

Surfactants which may be included in the inventive composition are preferably readily diffusing or diffusible surfactants to facilitate manufacturing and processing of the composition of the invention. Such surfactants can be of any particular type (ionic, non-ionic, zwitterionic) and may comprise as a proportion of dry weight of the composition from 0.01% to 10%, more preferably between 0.05 and 5%, ideally within or just outside the 0.1-1% range, for example from 0.2 to 0.5%.

Unless otherwise stated or required, all percentages and ratios are by weight.

In one embodiment, non-ionic surfactants are preferred. Possible non-ionic surfactants include perfluorocarbons, polyoxyethyleneglycol dodecyl ether (eg Brij such as Brij 35), Myrij, and compounds derived from polyethoxylated sorbitan and oleic acid including polyoxyethylene (20) sorbitan monooleate (available as Tween 80 or Polysorbate 80) and polyoxyethylene derivatives of sorbitan monolaurate including polyoxyethylene (20) sorbitan monolaurate (available as Tween 20 or Polysorbate 20). The invention foresees use of the commercially available products in which case additional components may be included with the principal molecular species as described in more detail by Ayorinde et al (2000) in an article entitled "Rapid Communications in Mass Spectrometry", Volume 14 Issue 22, Pages 2116-2124, the entirety of which is incorporated herein by reference. Other possible non-ionic surfactants include esters of sorbitan (a sorbitol derivative) and stearic acid such as octadecanoic acid [(2R)-2-[(2R,3R,4S)-3,4-dihydroxyoxolan-2-yl]-2-hydroxyethyl](Z)-octadec-9-enoate, available commercially as Span 80. Another possible non-ionic surfactant is sorbitan trioleate available commercially as Span 85. Brij, Myrij and Tween products are available from ICI. Span products are available from Sigma Aldrich. An alternative or additional non-ionic surfactant or emulsifier is mannide monooleate which, in a method of making the composition of the invention, may be introduced into the oil or aqueous phase before emulsification by itself or pre-mixed with another component of the composition of the invention. For example, if it is also desired to utilise squalene as a component of the composition, it is possible to introduce both components into the composition of the invention during manufacturing by using a commercially available water-in-oil emulsion which includes mannide monooleate (Montanide ISA 720 by Seppic Inc, France, based on squalene).

A mixture of non-ionic surfactants is particularly preferred. The mixture may combine one or more of those enumerated above. In one embodiment, the mixture is of a first non-ionic surfactant having a low HLB (approx <3) and a second non-ionic surfactant having a high HLB (approx >10). In another embodiment, a first non-ionic surfactant is oil-soluble and a second is aqueous soluble. A particularly preferred combination of non-ionic surfactants is polyoxyethylene (20) sorbitan monooleate (eg Tween 80) and sorbitan trioleate (eg Span 85)

Other categories of surfactant are also contemplated such as anionic surfactants bearing in mind that in some embodiments it is preferred that the composition be free of anionic surfactants. However, when they are present, preferred anionic surfactants for inclusion include perfluoro-octanoate (PFOA or PFO), perfluoro-octanesulfonate (PFOS), sodium dodecyl sulphate (SDS), ammonium lauryl sulphate, and other alkyl sulfate salts, sodium laureth sulphate, also known as sodium lauryl ether sulphate (SLES) and alkyl benzene sulphonate. Mixtures of anionic surfactants are also contemplated.

In one embodiment of the invention, the physical form of the surfactant at the point of introduction plays a role in the ease of manufacture of the composition according to the invention. As such, although liquid surfactants can be employed, it is preferred to utilize a surfactant which is in solid form (eg crystalline or powder) (semi solid) at room temperature, particularly when the aqueous phase comprises gelatin.

In general, mixtures of surfactants can be utilised eg. to achieve optimum long term stability of the composition of the invention with shorter chain surfactants being in general preferred according to the invention to facilitate shorter term stability (an aid to processing) and longer chain surfactants being in general preferred according to the invention to facilitate longer term stability (an aid to shelf life).

When anionic surfactants are incorporated in the composition of the invention, it may be in the aqueous phase. However, instead of (or as complement to) a surfactant in the aqueous phase, the invention also contemplates use of surfactant-like emulsifiers (also known as crystalisation inhibitors) such as HPMC (also known as hypromellose) although their use is generally contemplated in relatively smaller amounts to avoid high viscosity which may constrain processing options.

Non-ionic surfactants which may optionally be included in the aqueous phase include poloxamers which are nonionic triblock copolymers composed of a central hydrophobic chain of polyoxypropylene (poly(propylene oxide)) flanked by two hydrophilic chains of polyoxyethylene (poly(ethylene oxide)). Poloxamers are available commercially under the trade name Pluronics™. Such surfactants or similar larger polymeric surfactants are aqueously soluble and are therefore presented here as optional components of the aqueous phase. However, they may be used to reduce the amount of or to replace a higher HLB polymeric component of the oil phase (see also separate section) such as, for example, polyethoxylated castor oils (polyethylene glycol ethers) exemplified commercially as Cremophor™.

Another type of polymeric aqueous soluble surfactant which may be used in a similar way are anionic copolymers based on methacrylic acid and methyl methacrylate in which the ratio of the free carboxyl groups to ester groups is approx. 1:1 and with average molecular weight is approx. 135,000. Such a polymeric surfactant is available from Degussa under the trade name EUDRAGIT® L 100.

The invention includes embodiments in which one or more surfactants are included in the oil phase. In some embodiments, the aqueous phase does not have surfactants incorporated in it.

Oil Phase

Any pharmaceutically suitable oil or oils may be used to constitute the oil phase (oil drops) according to the invention. The oil phase comprises one or more pharmaceutically acceptable oils (water immiscible liquids) and may include other substances as described herein; the other substances may often be oleophilic or oil soluble but may be an internal aqueous phase of a water-in-oil emulsion. In terms of dry weight of the composition of the invention, the oil phase generally comprises a proportion from 10% to 85%, preferably 15% to 50%, more preferably 30% to 40%.

The oil phase may comprise one or more oils selected from: fatty acids; fatty acid esters; esters of polyethylene glycols, for example mono- and di-esters; hydrocarbon oils, for example natural hydrocarbon oils; and steroids, for example cholesterol. In one embodiment, the one or more oils are selected from fatty acids; fatty acid esters; esters of polyethylene glycols; and hydrocarbon oils. It is contemplated that such oils may form at least 50 weight percent of the oil phase. As fatty acids may be mentioned mono- or poly-unsaturated fatty acids. As fatty acid esters may be mentioned triglycerides, as well as esters of glycerol (particularly tri-esters) with a combination of fatty acids and lower molecular weight acids e.g. succinic acid (fatty acid triglycerides are a particular example of glycerides). Suitable fatty acids have from 6 to 24 carbon atoms, and particularly to be mentioned are long chain $C_{12}$-$C_{24}$ fatty acids e.g. $C_{15}$-$C_{22}$ acids. Also to be mentioned are medium chain $C_6$-$C_{12}$ fatty acids. Hydrocarbon oils may be terpenes and particularly triterpenes such as, for example, squalene and squalane (squalene being a preferred hydrocarbon oil).

Oils containing triglycerides may also contain mono- and/or di-glycerides, e.g. as a minor part of the glyceride content (less than 50 mol %). The oil phase typically comprises a mixture of oils, for example fatty acid macrogolglycerides, also known as polyoxylglycerides, which are mixtures of fatty acid monoesters, diesters and triesters of glycerol and fatty acid monoesters and diesters of polyethylene glycol; examples are oleoyl macrogolglycerides and linoeoyl macrogolglycerides. One class of oil phases disclosed herein comprises fatty acid macrogolglycerides and particularly oleoyl macrogolglyceride, e.g. in an amount of at least 15% by weight and optionally in an amount of at least 20%, at least 30%, at least 40%, at least 50% by weight, or at least 60% of the oil phase, e.g. 15%-60%, 20%-50%, 30%-50% or 30%-40%.

Oils which may be included in the oil phase, singly or in combination, include poly-unsaturated fatty acids such as omega-3 oils such as eicosapentanoic acid (EPA), docosohexaenoic acid (DHA), alpha-linoleic acid (ALA). Combinations of such components are also contemplated e.g. a mixture of EPA and DHA in a ratio of 1:5 available commercially under the trade name Epax 6000.

Alternative or additional oils which may be included (singly or in combination) in the oil phase include cholesterol-related or cholesterol-derived oils such as squalene (IUPAC name: (6E,10E,14E,18E)-2,6,10,15,19,23-hexamethyltetracosa-2,6,10,14,18,22-hexaene). One class of oil phases disclosed herein comprises squalene, e.g. in an amount of at least 10% by weight and optionally in an amount of at least 20%, at least 30%, at least 40% or at least 50% by weight of the oil phase, e.g. 10%-50%, 10%-40%, 15%-40% or 20%-30%.

Oils may be introduced into the oil phase of the composition of the invention during manufacture by using commercially available combinations of such oils with other components. For example, if squalene is used, it may conveniently be introduced into the composition using a water-in-oil (w/o) emulsion used in manufacture (see below for more detail). Such a w/o emulsion may desirably contain one or more emulsifiers in which case the emulsifier is also preferably present in the composition of the invention. A 30:70 aqueous to oil based on volume water-in-squalene oil emulsion which also contains mannide monooleate emulsifier is particularly preferred e.g. the product available commercially under the name Montanide ISA 720 from Seppic.

Other possible (alternative or additional) oils which may be included (singly or in combination) include linoleoyl macrogolglycerides (polyoxylglycerides) such as Labrafil M 2125 CS by Gattefosse, oleoyl macrogolglycerides (polyoxylglycerides) such as Labrafil® M 1944 CS and caprylocaproyl macrogolglycerides such as Labrasol by Gattefosse.

In a preferred embodiment more than one oil is used and it is particularly preferred to combine two oil compositions to provide an oil phase containing oil components belonging to two or more classes. As an example of such a combination may be mentioned combinations of oleoyl macrogolglycerides (polyoxylglycerides) e.g. Labrafil M 1944 CS, and squalene e.g. as supplied in Montanide ISA 720. Thus, the oil phase may comprise a combination of macrogolglyceride and hydrocarbon (e.g. terpene) oil. Particular oil phases comprise a combination of macrogolglyceride, e.g. oleoyl macrogolglycerides, and squalene.

Alternative or additional oils which may be included in the oil phase singly or in combination include natural triglyceride-based oils which include olive oil, sesame oil, coconut oil, palm kernel oil. Oils which are particularly preferred include saturated coconut and palm kernel oil-derived caprylic and capric fatty acids and glycerin e.g. as supplied under the trade name Miglyol™ a range of which are available and from which one or more components of the oil phase of the invention may be selected including Miglyol™ 810, 812 (caprylic/capric triglyceride); Miglyol™ 818: (caprylic/capric/linoleic triglyceride); Miglyol™ 829: (caprylic/capric/succinic triglyceride; Miglyol™ 840: (propylene glycol dicaprylate/dicaprate). Note that Miglyol™ 810/812 differ only in $C_8/C_{10}$-ratio and because of its low $C_{10}$-content, the viscosity and cloud point of Miglyol™ 810 are lower. The Miglyol™ range is available commercially from Sasol Industries.

Alternative or additional oils which may be included in the oil phase according to the invention are medium chain tryglycerides such as for example Labrafac™ Lipophile manufactured by Gattefosse in particular product number WL1349.

The oil phase may also include a solubilizer (which may also be referred to as an amphiphilic oil or a surfactant) and examples include polyethoxylated castor oils (polyethylene glycol ethers) which can be prepared by reacting ethylene oxide with castor oil. Commercial preparations may also be used as the solubilizer of the composition of the invention e.g. those commercial preparations which contain minor components such as polyethyelene glycol esters of ricinoleic acid, polyethyelene glycols and polyethyelene glycol ethers of glycerol. The preferred example is Cremophor by BASF Corp. also known as Cremophor EL.

In one embodiment of the invention, the oil phase comprises more than one component. For example, as just mentioned, the oil phase may comprise a solubilizer.

The oil phase preferably also comprises a solubilizer or co-solvent for the active principle (antigen or adjuvant). Examples of suitable co-solvents are 2-(2-ethoxyethoxy) ethanol available commercially under trade names Carbitol™, Carbitol cellosolve, Transcutol™, Dioxitol™, Polysolv DE™, and Dowanal DE™; or the purer Transcutol™ HP (99.9). Transcutol P or HP by Gattefosse are preferred.

The oil phase may also be a water-in-oil (w/o) emulsion so that the composition of the invention becomes a water-in-oil-in-water (w/o/w) emulsion. In other words, the oil phase is considered by theory to present an oil to the aqueous phase of the composition (thereby at least in manufacture forming an oil-water interface) and may either consist of a single liquid oleo-phase or contain an additional internal water phase.

The oil phase may include one or more active principles as discussed in more detail elsewhere herein particularly in the section entitled "Active Ingredients" et seq.

Aqueous Phase (Matrix Phase)

The aqueous phase (or "matrix phase") of the solid composition is derived from an aqueous liquid used during manufacture and in the solid composition may comprise a significant proportion of water or it may be essentially dry. The principal component of the aqueous phase of the composition according to the invention (preferably between 20% and 70%, more preferably between 30% and 60%, still more preferably between 35% and 55%, by dry weight thereof) is a water-soluble polymer matrix material although other components may also be included as described below.

While mixtures of water-soluble polymer matrix materials are contemplated by the invention, preferably the composition of the present invention comprises a matrix material which is substantially a single material or type of material among those described herein and/or a matrix which can be solidified without inclusion of specific additional polymeric components in the aqueous phase.

In one embodiment, the water-soluble polymer matrix material may be of one or more of those selected from gelatine, agar, a polyethylene glycol, starch, casein, chitosan, soya bean protein, safflower protein, alginates, gellan gum, carrageenan, xanthan gum, phtalated gelatine, succinated gelatine, cellulosephtalate-acetate, oleoresin, polyvinylacetate, hydroxypropyl methyl cellulose, polymerisates of acrylic or methacrylic esters and polyvinylacetate-phthalate and any derivative of any of the foregoing.

In a preferred embodiment, the polymer matrix material is a hydrocolloid ie. a colloid system wherein the colloid particles are dispersed in water and depending on the quantity of water available can take on different states, e.g., gel or sol (liquid). It is preferred to use reversible hydrocolloids (eg agar, gelatin etc) as opposed to irreversible (single-state) hydrocolloids. Reversible hydrocolloids can exist in a gel and sol state, and alternate between states with the addition or elimination of heat. Gelatin is a thermoreversible, rehydratable colloid and is particularly preferred. Gelatin derivatives such as succinated or phtalated gelatins are also contemplated. Hydrocolloids which may be used according to the invention include those derived from natural sources such as carrageenan (extracted from seaweed), gelatin (extracted from bovine, porcine, fish or vegetal sources), agar (from seaweed) and pectin (extracted from citrus peel, apple and other fruits). A non-animal based hydrocolloid may be preferred for certain applications e.g. administration to vegetarians or to individuals not wishing to ingest animal products for religious reasons. In relation to the use of carrageenan, reference is made to US patent application 2006/0029660 A1 (Fonkwe et al), the entirety of which is incorporated herein by reference. In one embodiment, the water soluble polymer is selected from selected from gelatin, agar and carrageenan (and in particular is gelatin or agar), or in another embodiment is a combination of two or all three thereof.

The aqueous phase may be referred to in one embodiment as the immobilized aqueous phase of the composition and according to one embodiment of the invention is preferably a gel ie. a substantially dilute crosslinked system, which exhibits no flow when in the steady-state. The internal network structure of the solidified aqueous phase may result from physical or chemical bonds, as well as crystallites or other junctions that remain intact within an extending fluid e.g. water.

In an alternative preferred embodiment, the polymer matrix is a non-hydrocolloid gum. Examples are the crosslinked salts of alginic acid. For example, aqueous solutions of sodium alginate gums extracted from the walls of brown algae have the well known property of gelling when exposed to di- and trivalent cations. A typical divalent cation is calcium, often in the form of aqueous calcium chloride solution. It is preferred in this embodiment that the crosslinking or gelling have arisen through reaction with such a multivalent cation, particularly calcium.

In an alternative preferred embodiment, the polymer matrix is chitosan which can exist in the form of biogels with or without additives as described e.g. in U.S. Pat. No. 4,659,700 (Johnson & Johnson); by Kumar Majeti N.V. Ravi in Reactive and Functional Polymers, 46, 1, 2000; and by Paul et al. in ST.P. Pharma Science, 10, 5, 2000, the entirety of all 3 of which is incorporated herein by reference. Chitosan derivatives e.g. thiolyated entities are also contemplated.

In the embodiment in which gelatin is the polymer matrix of the invention, reference is hereby made to "bloom strength", a measure of the strength of a gel or gelatin developed in 1925 by O. T. Bloom. The test determines the weight (in grams) needed by a probe (normally with a diameter of 0.5 inch) to deflect the surface of the gel 4 mm without breaking it. The result is expressed in Bloom (grades) and usually ranges between 30 and 300 Bloom. To perform the Bloom test on gelatin, a 6.67% gelatin solution is kept for 17-18 hours at 10° C. prior to being tested.

According to the invention, in the embodiment in which gelatin is the polymer matrix, it is preferred to use gelatin with bloom strength between 200 and 300, preferably between 210 and 280.

According to the invention, in the embodiment in which gelatin is the water-soluble polymer matrix material, the gelatin may be sourced by a variety of means. For example, it can be obtained by the partial hydrolysis of collagenous material, such as the skin, white connective tissues, or bones of animals. Type A gelatin is derived mainly from porcine skins by acid processing, and exhibits an isoelectric point between pH 7 and pH 9, while Type B gelatin is derived from alkaline processing of bones and animal (bovine) skins and exhibits an isoelectric point between pH 4.7 and pH 5.2. Type A gelatin is somewhat preferred. Gelatin for use in the invention may also be derived from the skin of cold water fish. Blends of Type A and Type B gelatins can be used in the invention to obtain a gelatin with the requisite viscosity and bloom strength characteristics for mini-bead manufacture.

Commercially gelatin can be obtained from the Sigma Chemical Company, St. Louis, Mo. USA or from Nitta (http://www.nitta-gelatin.com).

Lower temperature gelatin (or gelatin derivatives or mixtures of gelatins with melting point reducers) or other polymer matrices able to be solidified at lower temperatures (eg sodium alginate described above) are preferred for example when the active principle to be incorporated in the composition of the invention is temperature-labile or whose activity may be affected by exposure to higher temperatures.

According to the invention, in the embodiment in which gelatin is the polymer, the starting gelatin material is preferably modified before manufacture to produce "soft gelatin" by the addition of a plasticizer or softener to the gelatin to adjust the hardness of the composition of the invention. The addition of plasticizer achieves enhanced softness and flexibility as may be desirable to optimise dissolution and/or further processing such as coating. Useful plasticizers of the present invention include glycerin (1,2,3-propanetriol), D-sorbitol (D-glucitol), sorbitol BP (a non-crystallizing sorbitol solution) or an aqueous solution of D-sorbitol and sorbitans (eg Andidriborb 85/70). Other or similar low molecular weight polyols are also contemplated. Polyethylene glycol may also be used although this is less preferred and indeed particularly preferred compositions of the invention are free or substantially free of PEG or derivatives thereof. Glycerin and D-sorbitol may be obtained from the Sigma Chemical Company, St. Louis, Mo. USA or Roquette, France.

Softeners, if utilized, can be ideally incorporated in a proportion rising to 30%, preferably up to 20% and more preferably up to 10% by dry weight of the composition of the invention, even more preferably between 3 and 10%, and most preferably between 5% and 8%.

As noted in more detail above in the section on surfactants, it is preferred to include one or more surfactants in the composition of the invention, and more particularly at least a portion of the surfactant content of the composition, e.g. the whole surfactant content, is included in the oil phase. Certain surfactants may also act as plasticisers or softeners or vice versa. Surfactants can be ideally incorporated in a proportion rising to 15%, preferably up to 10% and more preferably up to 8% by dry weight of the composition of the invention, even more preferably between 2 and 8%, and most preferably between 3 and 6%.

A preferred surfactant is Tween 80 (Polysorbate 80).

Shape, Size and Geometry

The composition of the invention can be formed into a limitless number of shapes and sizes. In the section below describing the process for making the composition, various methods are given including pouring or introducing a fluid emulsion into a mould where it hardens or can be caused to harden. Thus the composition can be created in whichever form is desired by creating an appropriate mould (eg in the shape of a disc, pill, tablet or suppository). However, it is not essential to use a mould. For example, the composition may be extruded in the form of a droplet or bead which hardens or can be caused to harden.

Thus, the composition may be in the form of spheres or spherical-like shapes made as described below. Preferably, the composition of the invention is in the form of substantially spherical, seamless beads, especially mini-beads. The absence of seams on the mini-bead surface is an advantage e.g. in further processing such as coating since it allows more consistent coating. The absence of seams on the mini-beads also enhances consistency of dissolution of the mini-beads.

The preferred size or diameter range of mini-beads according to the invention can be chosen to avoid retention in the stomach upon oral administration of the mini-beads. Larger dosage forms are retained for variable periods in the stomach and pass the pyloric sphincter only with food whereas smaller particles pass the pylorus independently of food. Selection of the appropriate size range (see below) thus makes the prediction of therapeutic effect ie. immune response post-dosing more accurate. Compared to a single large monolithic oral format such as a traditional compressed pill, a plurality of mini-beads released into the GI tract (as foreseen by the present invention) permits greater intestinal lumen dispersion so enhancing absorption and adsorption via exposure to greater epithelial area, prevents irritation (e.g as otherwise seen with NSAIDs) and achieves greater topical coating (e.g. as may be desired for to target immune cells, such as M cells, in certain parts of the GI tract e.g. small intestine, ileum or colon).

The composition of the invention is preferably monolithic meaning internally (ie. cross-sectionally) homogeneous. This is particularly preferred for the mini-bead embodiment.

In the embodiment of the present invention which is in the form of mini-beads, the mini-beads generally range in diameter from 0.5 mm to 10 mm with the upper limit preferably 5 mm, e.g. 2.5 mm. A particularly convenient upper limit is 2 mm with 1.7 mm being particularly preferred. The lower limit can preferably be 1 mm, e.g. 1.2 mm, more preferably from 1.3 mm, most preferably from 1.4 mm. In one embodiment the diameter is from 0.5 to 2.5 mm, for example from 1 mm to 2 mm.

In embodiments, mini-beads of the invention are monodisperse. In other embodiments, mini-beads of the invention are not monodisperse. By "monodisperse" is meant that for a plurality of mini-beads (e.g. at least 100, more preferably at least 1000) the mini-beads have a coefficient of variation (CV) of their diameters of 35% or less, optionally 25% or less, for example 15% or less, such as e.g. of 10% or less and optionally of 8% or less, e.g. 5% or less. A particular class of polymer mini-beads has a CV of 25% or less. CV when referred to in this specification is defined as 100 times (standard deviation) divided by average where "average" is mean particle diameter and standard deviation is standard deviation in particle size. Such a determination of CV is performable using a sieve.

The invention includes minibeads having a CV of 35% and a mean diameter of 1 mm to 2 mm, e.g. 1.5 mm. The invention also includes minibeads having a CV of 20% and a mean diameter of 1 mm to 2 mm, e.g. 1.5 mm, as well as minibeads having a CV of 10% and a mean diameter of 1 mm to 2 mm, e.g. 1.5 mm. In one class of embodiments, 90% of beads have a diameter of from 0.5 mm to 2.5 mm, e.g. of from 1 mm to 2 mm.

Another possible form of the composition of the invention is as hemispherical beads two of which may optionally be joined at the flat face to create a single mini-bead with two distinct halves, each having a distinct composition, if that is desired, e.g. each containing different active principles or the same active principles but different excipients e.g. to achieve differing permeability, solubilisation, adsorption, absorption or release profiles as between the two hemispheres. For example, one side may comprise the active principle(s) such as antigens/adjuvants and the other side may comprise bioadhesives. In this example, either or both sides may also comprise pH-modifiers or other protectants e.g. protectants from gastric dissolution.

The embodiment in which the composition of the invention takes the form of mini-beads can be further developed to create a larger mass of mini-beads e.g. via compression (with appropriate oil or powder-based binder and/or filler known to persons skilled in the art of pharmaceutical formulation and with the option of including additional quantities of the same API as in the composition of the invention or a different API) of a plurality of mini-beads which disintegrate at a different rate in different conditions than a unitary moulded form of the same shape. The larger (eg compressed) mass may itself take a variety of shapes including pill shapes, tablet shapes, capsule shapes, suppository shapes etc. A particular problem which this version of the mini-bead embodiment solves is the "dead space" (above the settled particulate contents) and/or "void space" (between the particulate content elements) typically found in hardgel capsules filled with powders or pellets. In such pellet- or powder-filled capsules with dead/void space, a patient is required to swallow a larger capsule than would be necessary if the capsules contained no such dead space. The mini-beads of this embodiment of the invention may readily be compressed into a capsule to adopt the inner form of whichever capsule or shell may be desired leaving much reduced e.g. essentially no dead/void space.

Another possible form of the composition of the invention is as a capsule in which the core of the composition is a solid (eg gastro-retentive float material such as biocarbonate salts) or a fluid (a gas or a liquid). If the core is a liquid, it may contain an active principle and/or excipients which may be the same or different from those described above. Like the hemispherical beads described above, such capsules may have two halves of different constitution and sealed hermetically to retain the internal fluid. An internal layer e.g. internal film layer of non-aqueous material on the inner face of the sphere, may be included if it is desired that the core be an aqueous liquid such that the internal layer prevents the aqueous core from coming into contact with the inner surface of the capsule. With or without an intermediate layer, the core may be a variant of the composition of the invention so that the composition of the invention, in the mini-bead embodiment, comprises a core made from a first composition according to the invention and a capsule made from a second composition according to the invention.

The mini-bead embodiment of the invention, while by itself offering a range of solutions to the issues identified above, may also be used as a starting point for creation of more complex forms for example by using the mini-bead as a nonpareil seed on which additional layers of material can be applied as is well known to a person skilled in the art e.g. of pharmaceutical science. The material of the additional layers may comprise the same or different active principle and/or the same or different excipients as are described in this document. Such variants allow differential release of the same or different active principles and facilitate inclusion of multiple fixed-dose combination vaccines.

The composition of the invention may also be used for sublingual vaccination in which case the mini-beads may be formed, e.g. compressed as described above, into an appropriate flattened shape (eg disc or wafer) for insertion under the tongue. The inclusion of bioadhesives is particularly relevant to this embodiment of the invention. Alternatively, rather than use mini-beads, the pre-beaded formulation may be moulded into a flattened shape e.g. a disc or wafer for insertion under the tongue.

The composition of the invention may have a coat of additional material on its outer surface. This coat may be applied in a number of ways as described more particularly in the section below entitled "coating".

Other Characteristics

The composition of the invention, in certain embodiments, comprises one or more elements, components, excipients, structural features, functional features or other aspects of the prior art described above.

The relative and absolute concentration of the components, including the antigen and adjuvant may be determined by testing the formulations in animals using known methods and models starting with a low dose of the formulation and then increasing the dosage while monitoring the immune response. The following considerations should be made when determining an optimal dose, e.g., breed, age, size and the presence or absence of interfering maternal antibodies.

To summarise a limited number of embodiments of the invention in terms of their physico-chemical characteristics, the composition as described above and elsewhere herein may additionally be one or more of the following: substantially water-free, in a gel state, in a solid state, undissolved, non-powdered, formed, shaped, and not in solution.

Unless geometrically designed to comprise inner aqueous compartments (eg w/o/w format or capsular format with liquid core), it is desirable that the composition of the invention is essentially or substantially dry, e.g. contains less than 5%, preferably less than 1% of free water by weight. The mini-beads are preferably homogeneous although processing conditions may be varied (see below) to achieve for example heterogeneity such as a harder skin and softer core with less than complete immobilization of oil droplets towards the core as opposed to the surface of the bead. Larger (eg non-beaded) forms or shapes of the composition according to the invention may particularly be engineered to embody such heterogeneity.

The low free-water content is a distinguishing feature of certain embodiments of the compositions of the present invention. The free-water content can be measured using thermogravimetic analysis (TGA), for example with commercially available instrumentation, e.g. using a TGA Q 500 of TA Q series instrument. TGA measures changes in weight in relation to a change in temperature. For example, a TGA method can comprise a temperature scan, e.g. from 20 to 400° C. at 20° C. per minute, where the moisture content is obtained from the sample weight loss at about 100 degrees Celsius.

In one embodiment, the oil droplets in the composition of the invention are homogeneously dispersed in the solidified aqueous phase (or in some embodiments the water-soluble polymer matrix material) with substantial absence of coalescence between adjacent oil droplets. Thus the emulsion is preferably maintained during solidification. Coalescence of neighbouring oil droplets, preferably only occurs, if at all, on rehydration of the composition of the invention.

For certain embodiments, the inventors believe that the water soluble polymer matrix e.g. gelatin, may assist in maintaining particles within the desired size range and preventing their aggregation or coalescence.

Depending on process parameters, droplet size can vary broadly e.g. from 10 nm to 100 μm (diameter) e.g. 300-700 nm or 700 nm to 30 μm. However, the inventors/applicants have found that for certain embodiments it is beneficial to maintain droplet size in the range from 100 nm to 10 μm, e.g. from 0.5 μm to 7.5 μm. Particularly preferred ranges in some embodiments are from 0.75 μm to 5 μm e.g. 1 μm to 3 μm or 4 μm. Narrower ranges may apply to droplets with high monodispersity (low polydispersity). A population of droplets is monodisperse if the droplets have largely the same size while a population of droplets which has a broad size distribution is polydisperse.

We do not believe that this paragraph is necessary. It explains the theory of light scattering measurements, which might not be required for a patent regarding vaccine delivery.

In some embodiments high monodispersity (low polydispersity) is preferred and in others low monodispersity (high polydispersity) is preferred. Without wishing to be bound by speculation, the inventors believe that in certain embodiments, a more highly polydisperse system, the smaller droplets (eg in the range from 20 nm to 20 μm) may preferentially be absorbed by cells while the larger droplets (>20 μm) create a concentration gradient in the vicinity of the cells which absorb the smaller droplets and which is conducive to such absorption.

The composition of the invention generally comprises multiple oil drops or droplets within a moulded or shaped form e.g. a mini-bead which might typically contain many hundreds or thousands of droplets as distinct from a powder which generally derives from micron-sized particles incorporating a single or a small number of oil drops or droplets often following coalescence of smaller droplets during spray-drying. While powder embodiments are not excluded, the composition of the invention, if particulate, preferably comprises particles larger than powder particles such that the composition is in a non-powdered form.

In the embodiment in which the invention is in the form of minibeads, a plurality of minibeads may be presented in a single format e.g. contained in a single hardgel capsule which releases the mini-beads eg. in the stomach. Alternatively the minibeads may be presented in a sachet or other container which permits the minibeads to be sprinkled onto food or into a drink or to be administered via a feeding tube such as a naso-gastric tube or a duodenal feeding tube. Alternatively, the mini-beads may be administered as a tablet for example if a plurality of mini-beads are compressed into a single tablet as described elsewhere herein. Alternatively, the mini-beads may be filled e.g. compressed into a specialist bottle cap or otherwise fill a space in a specialised bottle cap or other element of a sealed container (or container to be sealed) such that e.g. on twisting the bottle cap, the mini-beads are released into a fluid or other contents of the bottle or vial such that the beads are dispersed (or dissolve) with or without agitation in such contents. An example is the Smart Delivery Cap manufactured by Humana Pharma International (HPI) S.p.A, Milan, Italy. A related or similar approach is also contemplated for e.g. timed release of mini-capsules into a reactor, feeding environment e.g. tank, incubator etc.

The mini-beads so-presented may be of a single type (or population) or may be of multiple types (or populations) differing between populations in relation to one or more features described herein e.g. different active principle(s) or different excipients or different physical geometry, coated, multiply coated, uncoated etc.

In one embodiment, the invention allows for mini-beads having immediate release (IR) characteristics and/or bearing no coat, enteric-only coat or coat designed to prevent release and/or dissolution of the bead only for a limited time. (Alternatively delayed release capability can be introduced into the body of the composition with or without a coating also being present). In another embodiment, the invention allows for mini-beads having delayed or sustained release (SR) characteristics e.g. bearing a coat as described in more detail elsewhere herein, particularly in the section entitled "coating". The invention also provides for an embodiment in which immediate release mini-beads are produced in combination with a Sustained Release or Controlled Release (CR) mini-beads in varying ratios of IR:SR/CR. The immediate release mini-beads can be combined with a Sustained or Controlled release mini-bead component in the following ratios (w/w by potency) e.g. 10% Immediate Release (IR)+ 90% Sustained (SR)/Controlled Release (CR) minicapsules; 20% IR+80% SR/CR; 30% IR+70% SR/CR; 40% IR+60% SR/CR and 50% IR+50% SR/CR.

Process for Making the Composition of the Invention

The reader is notified that it is important to refer to this section in relation to the Examples.

The basic method for making the composition of the invention is to mix a fluid form (preferably a solution) of the polymer chosen to be the water-soluble polymer matrix material (eg gelatin, gum, alginate etc as described more generally elsewhere herein and in any event optionally in admixture with other components described above) with an oil phase to form an homogeneous fluid emulsion. Taking account of the final composition required (as described elsewhere herein), the oil phase and the aqueous phase may be mixed (mixing may be achieved by stirring or other agitation) in a proportion in the range 1:6-10, preferably approximately 1:7 or 1:8. In general, only gentle stirring of the components is required using a magnetic or mechanical system e.g. overhead stirrer as would be familiar to a person skilled in the art to achieve emulsification. Continuous stirring is preferred. Any appropriate laboratory stirring apparatus or industrial scale mixer may be utilized for this purpose for example the Magnetic Stirrer (manufactured by Stuart) or Overhead Stirrer (by KNF or Fisher).

In the embodiment where the polymer matrix substantially comprises gelatin with the addition of sorbitol, the aqueous phase of polymer matrix is prepared by adding the appropriate quantities of sorbitol (and surfactant if desired) to water, heating to approximately 60-75° C. until in solution and then adding gelatin although the precise order and timing of addition is not critical. A typical "gelatin solution" comprises 15-25% (preferably 17-18%) gelatin; 75%-85% (preferably 77-82%) of water plus from 1-5% (preferably 1.5 to 3%) sorbitol.

The choice of temperature at which the emulsion is formed depends however on various factors include the temperature lability of the active pharmaceutical ingredient and the amount of plasticiser included in the gelatin, the type of gelatin, as well as other factors. Generally however, the gelatin solution (especially in the case of standard or normal gelatin) is maintained at 60° C.-70° C. to maintain it in a fluid state.

Where there are additional hydrophilic or aqueous soluble components for inclusion in the composition of the invention, they may be added to the aqueous phase before emulsification. Examples among the adjuvants are CpG, alpha-Gal-Cer and Poly I:C which are hydrophilic and are commercially supplied as aqueous solutions. Among the surfactants, aqueous soluble entities such as Tween 80 may also be incorporated first into the aqueous phase. However, it is equally possible to incorporate these aqueous soluble components in the oil phase e.g. by initially creating a water-in-oil (w/o) emulsion and thereafter dispersing this w/o emulsion in the aqueous phase proper to create a w/o/w emulsion, the initially-generated w/o emulsion being considered the oil phase for the purposes of this embodiment. In this embodiment, a particularly preferred "oil" phase results from combining the following 4 components (such that this "oil" phase in fact contains aqueous components):

oleoyl macrogolglycerides (polyoxylglycerides)
squalene with mannide monooleate
polyoxyethylene (20) sorbitan monooleate
sorbitan trioleate.

The completed oil phase will normally contain an active principle, e.g. and antigen.

In terms of commercially available components, the "oil" phase may for example comprise from 60-80% Labrafil, from 20%-30% Montanide ISA 720, from 0.01-1% Tween 80 and from 0.01-1% Span 85.

The oil phase may for example comprise fatty acid macrogolglyceride and particularly oleoyl macrogolglyceride, e.g. in an amount of at least 15% by weight and optionally in an amount of at least 20%, at least 30%, at least 40%, at least 50% by weight, or at least 60% of the oil phase, e.g. 15%-60%, 20%-50%, 30%-50% or 30%-40%. The balance of the oil phase may comprise squalene, surfactants and one or more active ingredients e.g. selected from antigens and adjuvants. The oil phase may consist of a single oleo-phase or be a water-in-oil emulsion.

One class of oil phases disclosed herein comprises squalene, e.g. in an amount of at least 10% by weight and optionally in an amount of at least 20%, at least 30%, at least 40% or at least 50% by weight of the oil phase, e.g. 10%-50%, 10%-40%, 15%-40% or 20%-30%. The balance of the oil phase may comprise fatty acid macrogolglyceride and particularly oleoyl macrogolglyceride, surfactants and one or more active ingredients e.g. selected from antigens and adjuvants. The oil phase may consist of a single oleo-phase or be a water-in-oil emulsion.

It will be appreciated, therefore, that the oil phase, whether having a single oleo-phase or being a water-in-oil emulsion, may comprise a combination of macrogolglyceride and hydrocarbon (e.g. terpene) oil together with one or more surfactants, e.g. non-ionic surfactants. Particular oil phases whether having a single oleo-phase or being a water-in-oil emulsion comprise a combination of macrogolglyceride, e.g. oleoyl macrogolglyceride, and squalene together with one or more surfactants, e.g. non-ionic surfactants.

The disclosure includes oil phases which contain the surfactant mannide oleate, and the inclusion of mannide oleate is an option for all compositions and oil phases described or claimed herein.

The antigen and or adjuvant may also be added to this "oil" phase. This method is preferred for certain ingredients which may be thermolabile as it allows higher processing temperatures e.g. for emulsification without (or with limited) degradation occurring.

Where gelatine is the water soluble polymer matrix, the processing temperature for the emulsification step can however be reduced to a desirable target temperature e.g. 37° C. by use of lower melting-point gelatin (or gelatin derivatives or mixtures of gelatins with melting point reducers) or other polymer matrix material such as sodium alginate for example when the active principle to be incorporated in the composition of the invention is temperature-labile. Alternatively, temperature-labile active principles may be processed at higher temperatures by using appropriate apparatus or machinery which limits the time during which the temperature-labile active principle is in contact with the higher temperature medium. For example, if gelatin droplets are being formed by machine extrusion and immediately cooled e.g. in a cooling bath, additional appropriate inlet tubing can be used to introduce temperature-sensitive active principle into the fluid gelatin solution (and the mixture can be immediately homogenized) very shortly before ejection from a beading nozzle or other droppletting process such that the duration of exposure of the active principle to the higher temperature gelatin is limited so reducing the degree of any heat-dependent degradation of the active principle. This process may use any appropriate device such as a homogenizer, e.g. a screw homogenizer, in conjunction with an extrusion-type apparatus as described for example in WO 2008/132707 (Sigmoid Pharma) the entirety of which is incorporated herein by reference.

Additional surfactant, e.g. anionic surfactant, may be added to the aqueous phase conveniently at the same time the other components are added to the aqueous phase solution e.g. polymer matrix material and plasticiser if included e.g. at the beginning of the processing session (before mixing with the oil phase). The physical form of the surfactant at the point of introduction into the aqueous phase during preparation may play a role in the ease of manufacture of the composition according to the invention. As such, although liquid surfactants can be employed, it is preferred to utilize a surfactant which is in solid form (eg crystalline or powder) at room temperature, particularly when the aqueous phase comprises gelatin. Surfactant is added in the appropriate amount required to achieve the proportion desired and as described above. In general this leads to presence of surfactant in an amount between 0.8% and 1% (by weight) of the aqueous phase.

As noted, the aqueous phase may also include one of the polymers described below in the section on coatings whether or not the final composition is to bear a coating. Thus one or more derivatives of hydroxypropyl methylcellulose (HPMC) such as hydroxypropyl methylcellulose phthalate (HPMCP) may be added to the aqueous phase conveniently at the same time the other components are added to the aqueous phase solution before mixing with the oil phase.

One or more bases such as sodium bicarbonate ($NaHCO_3$) or sodium hydroxide (NaOH) or a mixture of more than one such base, may be added to the aqueous phase conveniently at the same time the other components are added to the aqueous phase solution e.g. polymer matrix material, plasticiser and additional surfactant, if included, e.g. at the beginning of the processing session (before mixing with the oil phase). Base may be included in the aqueous phase to enable an enteric material (e.g. an enteric polymer, for example HPMCP) to be dissolved. It has been found in one embodiment (see Example 22) that inclusion of NaOH is undesirable and it is speculated that high pH may in this case have been detrimental in particular to the adjuvant alphaGalCer. It is therefore desirable not to use alphaGalCer in aqueous formulations having a high pH. In one embodiment the pH of an alphaGalCer-containing aqueous phase does not exceed 10; in another embodiment, the pH does not exceed 9; in a further embodiment, the pH does not exceed 8. The invention includes embodiments in which an alphaGalCer-containing aqueous phase is free of inorganic base and embodiments in which it is free of base.

It may be desirable across all embodiments of the invention to avoid a high pH aqueous phase because of the possibility of detrimental consequences. In one embodiment the pH of the aqueous phase does not exceed 10; in another embodiment, the pH does not exceed 9; in a further embodiment, the pH does not exceed 8. The invention includes embodiments in which the aqueous phase is free of inorganic base and embodiments in which it is free of base. The invention includes embodiments in which the formulation is free of inorganic base. The invention includes embodiments in which the aqueous phase is free of base. The invention includes embodiments in which the formulation is free of base.

It is contemplated that it might also be detrimental for the aqueous phase to have a very low pH, for example of no lower than 4 or, in other embodiments, no lower than 5 or no lower than 6. The aqueous phase, and optionally the formulation, may be free of acid therefore. It may be desirable, therefore, that the aqueous phase should have a pH close to neutral, e.g. from 4 to 10, optionally from 5 to 9 as in the case of, for example, 6 to 8.

Where it is desired to include an enteric protectant in the formulation and to avoid having an aqueous phase with a sufficiently high pH to dissolve the enteric protectant, an enteric material (e.g. a combination of enteric materials) may provided in the polymer matrix and/or be comprised in a coating.

Generally (but this is not mandatory), the oil phase need not be heated and active principles and other oil phase components as described above are added at room temperature with stirring until clear. The appropriate amount of oil phase active principle (eg antigen and/or adjuvant) is added to achieve the target proportion as described elsewhere herein and in the examples. Stirring can continue for a few minutes to a few hours, even overnight, depending on the active principle.

The emulsion is formed by addition of the oil phase to the heated aqueous phase with stirring as described above, the aqueous phase being heated where solidification involves cooling as in, for example, the case of gelatin. The resultant emulsion then has the composition of the solidified minibeads described above but with water still present.)

The emulsion is then poured or introduced into a mould or other vessel or poured onto sheets or between sheets or delivered dropwise (or extruded) into another fluid such that the polymer matrix-containing aqueous phase, on solidification, takes the form of the mould, vessel, sheet or droplet/bead intended. It is preferred to progress to mould-forming e.g. beading without delay.

Alternatively to moulding, specialised machinery can be employed for example to create the hemispherical beads described above (see section above entitled "Shape, Size and Geometry") in which the invention takes the form of hemispherical beads. It is possible to manufacture a single bead made from joining two such hemispheres (ie. a single bead having two distinct halves) by using specialist apparatus in which two tubes through which two different emulsions are flowing, normally of circular cross section, are joined shortly before an extrusion point or nozzle (which may be vibrating) into a single dual lumen tube with a flat wall separating the two emulsion flows and which prevents the two emulsions from coming into contact until the point of extrusion. The cross-section of the joined dual-lumen tube up to the point of extrusion therefore appears as two semicircles. In operation, the two hemispherical emulsion flows combine to form a single, substantially spherical, bead on extrusion such that normal droplets are ejected/extruded for solidification. It is also possible to use a specialist pipette in which two lumens are joined shortly before the nozzle to force together expelled fluid emulsion from two lumens simultaneously.

Solidification can occur in a variety of ways depending on the polymer of the matrix, for example by changing the temperature around the mould, vessel, sheet, droplet/bead etc or by applying a solidification fluid or hardening solution so that the moulded shape is gelled or solidified.

In the preferred embodiment in which the composition of the invention takes the form of mini-beads, the mini-beads may be formed for example by using a pipette and dropping the fluid emulsion manually dropwise into a fluid which effects solidification.

In the case where solidification can be achieved by raising or reducing temperature, the temperature of the solidification fluid can be adapted to achieve solidification at the desired rate. For example, when gelatin is used as the polymer matrix, the solidification fluid is at a lower temperature than the temperature of the emulsion thus causing solidification of the polymer matrix. In this case, the solidification fluid is termed a cooling fluid.

In the case where solidification can be achieved chemically, e.g. by induction of cross-linking on exposure to a component of the solidification fluid, the concentration of such component in the solidification fluid and/or its temperature (or other characteristic or content) can be adjusted to achieve the desired rate and degree of solidification. For example, if alginate is chosen as the polymer matrix, one component of the solidification fluid may be a calcium-containing entity (such as calcium chloride) able to induce cross-linking of the alginate and consequent solidification. Alternatively, the same or similar calcium-containing entity may be included (eg dispersed) in the aqueous phase of the fluid emulsion prior to beading and triggered to induce cross-linking e.g. by applying a higher or lower pH to a solidification fluid into which droplets of emulsion fall dropwise or are introduced. Such electrostatic cross-linking can be varied as to the resulting characteristics of the mini-bead by control of calcium ion availability (concentration) and other physical conditions (notably temperature). The solidification fluid may be a gas (such as air) or a liquid or both. For example, when gelatin is used as the polymer matrix, the solidification fluid can be initially gaseous (eg droplets passing through cooling air) and then subsequently liquid (eg droplets passing into a cooling liquid). The reverse sequence may also be applied while gaseous or liquid cooling fluids alone may also be used. Alternatively, the fluid may be spray-cooled in which the emulsion is sprayed into a cooling gas to effect solidification.

In the case of gelatin or other water-soluble polymer destined to form the immobilization matrix, it is preferred that the solidification fluid be a non-aqueous liquid (such as medium chain triglycerides, mineral oil or similar preferably with low HLB to ensure minimal wetting) which can conveniently be placed in a bath (cooling bath) to receive the droplets of emulsion as they solidify to form beads. Use of a non-aqueous liquid allows greater flexibility in choice of the temperature at which cooling is conducted.

Where a liquid cooling bath is employed, it is generally maintained at less than 20° C., preferably maintained in the range 5-15° C., more preferably 8-12° C. when standard gelatin is used as the polymer matrix. If a triglyceride is chosen as the cooling fluid in the cooling bath, a preferred example is Miglyol 810 from Sasol.

If gelatin is selected as the polymer matrix, respect for appropriate temperature ranges ensures solidification of the gelatin at an appropriate rate to avoid destruction e.g. of tertiary protein structure in the case where the active principle is a protein.

If alginate is selected as the polymer matrix, a typical method of making mini-beads involves dropwise addition of a 3% sodium alginate solution in which oil droplets are dispersed as described above into a 4° C. crosslinking bath containing 0.1 M calcium chloride to produce calcium alginate (this method can be referred to as "diffusion setting" because the calcium is believed to diffuse into the mini-beads to effect cross-linking or setting). Using a syringe pump, manual pipette or Inotech machine, droplets can be generated or extruded (eg at 5 mL/h if a pump is used) through a sterile needle or other nozzle (described elsewhere herein) which can be vibrating as discussed elsewhere herein. Airflow of between 15 and 20 L/min through 4.5 mm tubing can be applied downwards over the needle to reduce droplet size if desired. Newly formed mini-beads can then be stirred in the calcium chloride bath for up to an hour.

An alternative approach when using alginate is internal gelation in which the calcium ions are dispersed in the aqueous phase prior to their activation in order to cause gelation of hydrocolloid particles. For example, this can be achieved by the addition of an inactive form of the ion that will cause crosslinking of the alginate, which is then activated by a change in e.g. pH after sufficient dispersion of the ion is complete (see Glicksman, 1983a; Hoefler, 2004 which are both incorporated herein by reference). This approach is particularly useful where rapid gelation is desired and/or where the diffusion approach may lead to loss of API by diffusion thereof into the crosslinking bath.

Following shape-forming, moulding or beading, the resultant shapes or forms may be washed then dried if appropriate. In the case of mini-beads solidified in a solidification fluid, an optional final step in the method of production described above therefore comprises removal of the solidified mini-beads from the solidification fluid. This may be achieved e.g. by collection in a mesh basket through which the solidification fluid (eg MCT) is drained and the beads retained. Excess fluid may then be removed using a centrifuge followed by optional washing of the mini-beads (eg using ethyl acetate) then drying of the beads to remove water or free water. This can be achieved by any suitable process known in the art such as use of a drum drier (eg Freund Drum dryer which may be part of the Spherex equipment train if used) with warm air at between 15° C. and 25° C., preferably around 20° C. leading to evaporation or entrainment of the water by the air. Use of gelatin as the polymer matrix (eg as principal constituent of the aqueous immobilisation phase) in most cases requires a drying step and for mini-beads this is preferably achieved by drying in air as above described. The resultant composition (the composition of the invention) is essentially dry as described in more detail above.

In terms of the way in which emulsion droplets may be formed in the first step of the beading process described above, variations of the above described method are possible including manual and automated pipetting of droplets into a variety of solidification fluids.

In general, the mini-beads may be generated by the application of surface tension between the fluid o/w (or w/o/w) emulsion and an appropriate solidification fluid such as gas or liquid in order to create the spherical or substantially spherical shape of the ultimate beads.

Alternatively, the mini-beads may be produced through ejection or extrusion of the fluid o/w emulsion through an orifice or nozzle with a certain diameter and optionally subject to selected vibrational frequencies and/or gravitational flow. Examples of machines which may be used are the Freund Spherex, ITAS/Lambo, Globex or Inotech processing equipment. Alternative extruders are applicable where the materials are suitable for low temperature and low pressure extrusion.

Operation of the Spherex machine manufactured by Freund as may be desired to manufacture mini-beads according to the present invention is described in U.S. Pat. No. 5,882,680 (Freund), the entire contents of which are incorporated herein by reference. It is preferred to select a vibrational frequency in the region of 10-15 RPM although the ultimate choice (and separately the amplitude of vibration selected) depends on the viscosity of the emulsion to be beaded. If the polymer matrix is chosen to solidify at lower temperature, it may be appropriate to maintain the lines to the orifice/nozzle at a certain temperature to maintain the fluidity of the solution.

The Spherex machine (and others) may be adapted to make use of a dual concentric lumen nozzle to ensure simultaneous extrusion of two fluids, the fluid in the inner lumen forming a core and the fluid of the outer lumen forming a capsule. The fluid forming the capsule is solidified according to one of the methods described. It may or may not be desirable for the fluid forming the core to be susceptible of solidification to yield a particular embodiment of the composition of the invention.

The above machinery adapted in this way can be used to manufacture the composition of the invention in the form of a capsule in which the core of the composition is filled with a fluid (a gas or a liquid) as described in the section above entitled "Shape, Size and Geometry" (noting that the core, like the capsular material, may be a composition, albeit optionally a distinct composition, according to the invention ie. susceptible of solidification according to one of the methods described above). A three-lumen nozzle and appropriate tubing may be employed if it is desired to include an intermediate internal layer e.g. internal film layer of non-aqueous material on the inner face of the sphere with the intermediate layer conveniently being solid at room temperature. Thus, in terms of the softness/hardness of successive layers, the composition may for example be described as solid:solid in the case of two layers or solid:solid:solid in the case of 3 layers or liquid/semi-liquid:solid:solid in the case of 3 layers.

The preceding paragraphs describe the formation of uncoated beads. It is a preferred embodiment of the present invention to have coated beads which are described in more detail elsewhere herein. Such coatings may be single or multiple and may be applied in a number of ways (see separate section).

Figure 7:
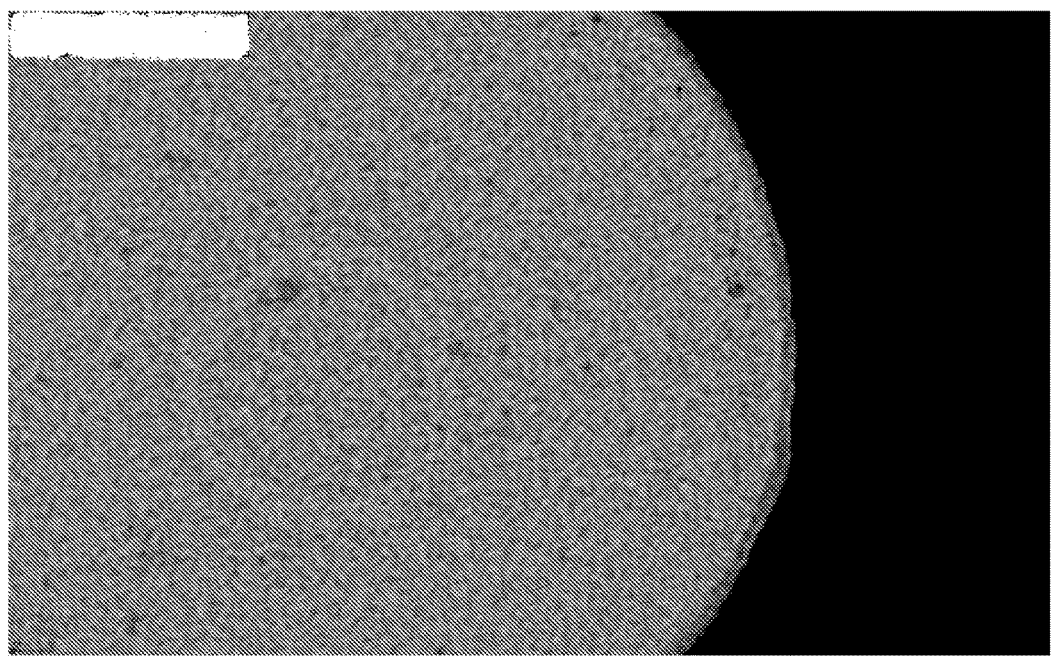
FIG. 7 is an X-ray tomography image of a coated mini-bead made by a process comprising ejection of emulsion through an optionally vibrating nozzle.

FIG. 7 is an X-ray tomography image of a coated mini-bead (in this case not comprising an active principle of the invention) made by a process comprising ejection of emulsion through an optionally vibrating nozzle as described above, from which it can be seen that the internal structure is essentially homogeneous.

With regard to one of the methods described above (ejection of emulsion through an optionally vibrating nozzle) with two concentric orifices (centre and outer), the outer fluid may form a coat (outside the mini-bead) of e.g. polymeric material (polymeric coating) which may contain an active principle or may impart controlled release characteristics to the mini-bead and the inner layer (core) may be a composition according to the invention. The Spherex machine manufactured by Freund (see U.S. Pat. No. 5,882,680 to Freund) is preferably used (the entire contents of this patent is incorporated herein by reference).

Use of the Spherex machine achieves very high monodispersity of bead size (diameter). The disclosure therefore includes monodisperse mini-beads, namely mini-beads having a coefficient of variation (CV) of their diameters of less than 20%, for example less than 15%, typically of less than 10% and optionally of less than 8%, e.g. less than 5%. For example, in a typical 100 g, batch 97 g of mini-beads were between 1.4 to 2 mm diameter. Desired size ranges can be achieved by methods known in the art for rejecting/screening different sized particles. For example, it is possible to reject/screen out the larger/smaller beads by passing a batch first through e.g. a 2 mm mesh and subsequently through a 1.4 mm mesh.

The 1.4 to 2 mm diameter range is a good size if it is desired to coat the mini-beads (if smaller, the spray of the coating machine may bypass the mini-bead; if too large, the beads may be harder to fluidise which is necessary to achieve consistent coating).

The mini-beads are preferably internally (ie. cross-sectionally) homogeneous ie. monolithic although processing conditions may be varied for example by altering the temperature of the fluid emulsion, the solidification fluid and the concentration of components in these fluids and the time allowed for certain processing steps to occur including drying. Although not currently preferred, such variations may be applied in the case of mini-bead manufacture to achieve heterogeneity such as a harder skin and softer core with less than complete immobilization of oil droplets towards the core as opposed to the surface of the bead. Larger (eg non-beaded) forms or shapes of the composition according to the invention may particularly be engineered to embody such heterogeneity. However, it is currently preferred to have internally homogenous compositions according to the invention and within the mini-bead embodiment, this can be favoured by conducting the beading/droplet ting using a homogeneous medium eg. a well dispersed emulsion. Such homogeneity in the emulsion to be beaded can help avoid the drying conditions affecting symmetry.

Coating

The composition of the invention may be used for a number of applications as discussed elsewhere herein. For example, the composition of the invention may be used for the vaccination of animals, for example humans, other mammals, birds or fish. Where it is desired to add the composition to the water in which fish dwell in order to vaccinate the fish, the composition of the invention may include excipients or components in the matrix polymer to slow or prevent dissolution of the vaccine in the water before consumption by the fish. Alternatively a coating may be applied to prevent or slow or delay release of the vaccine and/or delay or prevent dissolution of the water-soluble matrix.

When added to feed (eg for vaccination of animals) or administered directly by oral administration (oral delivery of active vaccine components or principles), the principles may be advantageously released immediately (immediate release profile) or be released after some delay and/or over an extended period (delayed and/or extended release profile). For immediate release, the composition, e.g. in the form of mini-beads, may be uncoated, contain a retardant/protectant or be coated enterically to protect against stomach acid for immediate release in the small intestine.

Alternatively or in addition, if controlled release is desired (ie. delayed, extended or site-targeted release etc), or if media-independent release is desired, it is possible, according to the invention to apply a coat to the composition e.g. in the form of mini-beads. Application of the appropriate coat may, for example if colonic release is required, allow for say less than 10% of the active principle to be dissolved (in dissolution medium) at 4 hours and then a burst (sudden release) towards a maximum dissolution (approaching 100%) in the subsequent 24 hours. Many alternative target profiles are possible and this example is purely for illustration.

Thus according to one embodiment of the present invention, the composition is in the form of mini-spheres at least some of which bear a coat (ie. are coated) in order to control release of active principle from the composition, e.g. in the form of mini-beads. In one embodiment, the coat is a film and in another embodiment, it is a membrane. The coat, film or membrane comprises one or more substances preferably of a polymeric nature (eg methacrylates etc; polysaccharides etc as described in more detail below) or combination of more than one such substance, optionally including other excipients or active principles described e.g. in the sections above on active principles. More than one coat may be applied with additional coats being of the same or different polymeric category as the first coat. Poly-A-lysine is such a coat e.g. secondary coat. Also perfluorocarbons may be used as coating e.g. secondary coating. Perfluorocarbons can act as stabilizing films.

In the case of combinations of polymers, combinations may be selected in order to achieve the desired delay (or other change) in the release of the drug and/or poration of the coating and/or exposure of the mini-bead within the coating to allow egress of drug and/or dissolution of the immobilization matrix. In one embodiment, two types of polymers are combined into the same polymeric material, or provided as separate coats that are applied to the mini-beads.

It has previously been stated that the composition of the invention may comprise more than one population of mini-beads. Within the coating embodiment, the differences between populations may lie in the coat ie. two (or more) populations of mini-beads may differ in a number of respects one of which is the coating (e.g. as to its presence or composition, or the number of coatings).

The coat may be applied as described below and may vary as to thickness and density. The amount of coat is defined by the additional weight added to (gained by) the dried composition (eg mini-bead) of the invention. Weight gain is preferably in the range 0.1% to 50%, preferably from 1% to 15% of the dry weight of the bead, more preferably in the range 3% to 10%.

The polymeric coating material may comprise methacrylic acid co-polymers, ammonio methacrylate co-polymers, or mixtures thereof. Methacrylic acid co-polymers such as EUDRAGIT™ S and EUDRAGIT™ L (Evonik) are particularly suitable. These polymers are gastroresistant and enterosoluble polymers. Their polymer films are insoluble in pure water and diluted acids. They may dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit solubility at a variety of pH levels, e.g. between the pHs at which EUDRAGIT™ L and EUDRAGIT™ S are separately soluble.

The trademark "EUDRAGIT" is used hereinafter to refer to methacrylic acid copolymers, in particular those sold under the EUDRAGIT™ by Evonik.

The coating can comprise a polymeric material comprising a major proportion (e.g., greater than 50% of the total polymeric coating content) of at least one pharmaceutically acceptable water-soluble polymer, and optionally a minor proportion (e.g., less than 50% of the total polymeric content) of at least one pharmaceutically acceptable water insoluble polymer. Alternatively, the membrane coating can comprise a polymeric material comprising a major proportion (e.g., greater than 50% of the total polymeric content) of at least one pharmaceutically acceptable water insoluble polymer, and optionally a minor proportion (e.g., less than 50% of the total polymeric content) of at least one pharmaceutically acceptable water-soluble polymer.

Ammonio methacrylate co-polymers such as EUDRAGIT™ RS and EUDRAGIT™ RL (Evonik) are suitable for use in the present invention. These polymers are insoluble in pure water, dilute acids, buffer solutions, and/or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and trimethylammonioethyl methacrylate chloride (TAMCI) groups in the polymer. For example, those polymers having EA:MMA:TAMCI ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability.

The amino methacrylate co-polymers can be combined in any desired ratio, and the ratio can be modified to modify the rate of active principle release. For example, a ratio of EUDRAGIT™ RS: EUDRAGIT™ RL of 90:10 can be used. Alternatively, the ratio of EUDRAGIT™ RS: EUDRAGIT™ RL can be about 100:0 to about 80:20, or about 100:0 to about 90:10, or any ratio in between. In such formulations, the less permeable polymer EUDRAGIT™ RS generally comprises the majority of the polymeric material with the more soluble RL, when it dissolves, permitting gaps to be formed through which solutes can come into contact with the mini-bead allowing pre-dissolved pharmaceutical actives to escape in a controlled manner.

The amino methacrylate co-polymers can be combined with the methacrylic acid co-polymers within the polymeric material in order to achieve the desired delay in the release of the active principle and/or poration of the coating and/or exposure of the mini-bead within the coating to allow egress of drug and/or dissolution of the immobilization or water-soluble polymer matrix. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the mini-beads.

Eudragit™ FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques.

In addition to the EUDRAGIT™ polymers described above, a number of other such copolymers can be used to control drug release. These include methacrylate ester co-polymers such as the EUDRAGIT™ NE and EUDRAGIT™ NM ranges. Further information on the EUDRAGIT™ polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg 109-114 the entirety of which is incorporated herein by reference.

Several derivatives of hydroxypropyl methylcellulose (HPMC) also exhibit pH dependent solubility and may be used in the invention for coating (this is instead of or in addition to their use as retardants/protectants as described above). These include hydroxypropyl methylcellulose phthalate (HPMCP), which rapidly dissolves in the upper intestinal tract and hydroxypropyl methylcellulose acetate succinate (HPMCAS) in which the presence of ionizable carboxyl groups causes the polymer to solubilize at high pH (>5.5 for the LF grade and >6.8 for the HF grade). These polymers are commercially available from Shin-Etsu Chemical Co. Ltd.

It is particularly preferred according to the invention to use a polmeric coating substance which is pH-independent in its dissolution profile and/or in its ability to release active principles incorporated in the mini-beads of the invention. Examples have already been given (e.g., Eudragit RS and RL). Another example of a pH-independent polymeric coating substance is ethylcellulose, in particular a dispersion of ethylcellulose in a sub-micron to micron particle size range, e.g. from about 0.1 to 10 microns in size, homogeneously suspended in water with the aid of an emulsification agent, e.g. ammonium oleate. The ethylcellulose dispersion may optionally and preferably contain a plasticizer, for example dibutyl sebacate or medium chain triglycerides. Such ethylcellulose dispersions may, for example, be manufactured according to U.S. Pat. No. 4,502,888, which is incorporated herein by reference. One such ethylcellulose dispersion suitable for use in the present invention and available commercially is marketed under the trademark Surelease®, by Colorcon of West Point, Pa. USA. In this marketed product, the ethylcellulose particles are, e.g., blended with oleic acid and a plasticizer, then optionally extruded and melted. The molten plasticized ethylcellulose is then directly emulsified, for example in ammoniated water optionally in a high shear mixing device, e.g. under pressure. Ammonium oleate can be formed in situ, for instance to stabilize and form the dispersion of plasticized ethylcellulose particles. Additional purified water can then be added to achieve the final solids content. See also U.S. Pat. No. 4,123,403, which is incorporated herein by reference.

The trademark "Surelease®" is used hereinafter to refer to ethylcellulose coating materials, for example a dispersion of ethylcellulose in a sub-micron to micron particle size range, e.g. from about 0.1 to 10 microns in size, homogeneously suspended in water with the aid of an emulsification agent, e.g. ammonium oleate. In particular, the trademark "Surelease®" is used herein to refer to the product marketed by Colorcon under the Surelease® trademark.

Surelease® dispersion is an example of a combination of film-forming polymer, plasticizer and stabilizers which may be used as a coating to adjust rates of active principle release with reproducible profiles that are relatively insensitive to pH. The principal means of drug release is by diffusion through the Surelease® dispersion membrane and is directly controlled by film thickness. Use of Surelease® is particularly preferred and it is possible to increase or decrease the quantity of Surelease® applied as coating in order to modify the dissolution of the coated mini-bead.

The invention also contemplates using combinations of Surelease with other coating components, for example pectin or sodium alginate, e.g. sodium alginate available under the trade name Nutrateric™.

In addition to the EUDRAGIT™ and Surelease® polymers discussed above, other enteric, or pH-dependent, polymers can be used. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate. Additionally, where compatible, any combination of polymer may be blended to provide additional controlled- or targeted-release profiles.

The coating can further comprise at least one soluble excipient to increase the permeability of the polymeric material. Suitably, the at least one soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose, and sucrose, sugar alcohols such as lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The at least one soluble excipient can be used in an amount ranging from about 1% to about 10% by weight, based on the total dry weight of the polymer.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566 all of which are incorporated herein by reference in their entirety.

The coating (or any additional or secondary coating) may also include, particularly in embodiments suitable for animal (including fish) vaccines, taste-masking or taste-promoting excipients e.g. excipients which mask or promote the taste of the vaccine composition. Taste-masking or taste-promoting excipients for children ie. for paediatric vaccine formulations may also be included in the composition and/or the coating. Colour (eg dyes, especially dyes acceptable for foodstuffs or for pharmaceuticals) may be included in the coating or the composition within the coating e.g. to make the composition attractive to children or animals e.g. colour for poultry and glitter for fish. Integrins or integrin-like entities, such as lactadherin etc which bind to exosomes, dendritic cells etc may also be included in the coating (or indeed in the body of the composition of the invention).

Polymers having functional groups which react with or have an affinity for the surface of the minibeads may be used to coat the minibeads ie. as coatings. In particular, where the bead comprises alginate, polymers having affinity for alginate may be used as coatings. Polylysine is an example of such a coating polymer and may advantageously be selected when the antigen and/or adjuvant comprises a nucleic acid antigen.

As noted above, Surelease is a particularly preferred polymer coating owing to its pH-independent dissolution character. However, the inventors/applicants have found that it is difficult to select the appropriate amount (weight gain) of Surelease to achieve optimal dissolution. It has been found that too much Surelease leads to incomplete (or over slow) dissolution while too little leads to over fast dissolution.

in a particular embodiment, it is preferred to add to Surelease™ a second polymer (eg a polysaccharide, especially a heteropolysaccharide) which is normally degraded by bacterial enzymes (and optionally or alternatively by pancreatic or other relevant enzymes).

The invention therefore also provides compositions intended to release their active payload (antigens and/or adjuvants) in the colon which is a combination of ethylcellulose (preferably formulated with an emulsification agent such as ammonium oleate and/or a plasticizer such as dibutyl sebacate or medium chain triglycerides) and a polysaccharide susceptible of degradation by a bacterial enzyme normally found in the colon. Such polysaccharides include chondroitin sulphate, pectin, dextran, guar gum and amylase, chitosan, lectins, etc and derivatives of any of the foregoing. A particularly preferred polysaccharide in this embodiment of the present invention is pectin.

The coating may comprise a combination of ethylcellulose (preferably formulated with an emulsification agent such as ammonium oleate and/or a plasticizer such as dibutyl sebacate or medium chain triglycerides) and a polysaccharide susceptible of degradation by a bacterial enzyme normally found in the colon; the composition may include a liquid vehicle, e.g. water.

Where the water-soluble polysaccharide (WSP) is pectin, the proportion of Surelease™ to pectin is ideally in the range 90:10 to 99:1, preferably, 95:5 to 99:1, more preferably 98:2 to 99:1. The weight gain and ratio between Surelease™ and WSP can be varied to refine the behaviour of the coating and the composition of the invention when it bears such a coat. It is preferred to select a weight gain in the range 0 to 30% (preferably 5 to 10%) and a Surelease to pectin ratio in the range 95:5 to 99.5:0.5 preferably 97:3 to 99:1 inclusive.

Although the focus above has been on extending and/or sustaining release of active principles from mini-beads according to the invention, also contemplated are uncoated or simple enteric coated mini-beads providing early, small intestinal API release with sufficient enteric coating and/or retardant/protectant content merely to protect the minibeads from dissolution in the stomach.

It is preferred to dry the mini-beads before they are coated with a suitable polymeric coat (as described in more detail elsewhere herein) and before any additional coating is applied.

The coating process can be carried out by any suitable means such as by use of a coating machine which applies a solution of a polymer coat (as described above in particular) to the mini-beads. Polymers for coating are either provided by the manufacturer in ready-made solutions for direct use or can be made up before use following manufacturers' instructions.

Appropriate coating machines are known to persons skilled in the art and include, for example, a perforated pan or fluidized-based system such as the GLATT, Vector, ACCELACOTA, Diosna, O'Hara and/or HICOATER processing equipment. Most preferred is the MFL/01 Fluid Bed Coater (Freund) used in the "Bottom Spray" configuration.

Typical coating conditions are as follows:

| Process Prameter | Values |
| --- | --- |
| Fluidising airflow (lpm (liters per minute)) | 150-200 |
| Inlet air temperature (° C.) | 30-70 |
| Exhaust air temperature (° C.) | 26-42 |
| Product temperature (° C.) | 26-42 |
| Atomizing air pressure (psi) | 10/13 |
| Spray rate (RPM) | 25 |

Whether as part of the polymeric coat or independently thereof, the mini-beads of the invention may be coated with additional drug layers using methods conventional in the art of pharmaceutical science to produce a composition having one or more layer(s), each layer containing one or more active pharmaceutical or other ingredient/excipient as described elsewhere herein. The polymeric coat(s), if desired, may be applied before or after such drug layering. This approach leads to vaccine compositions comprising other active principles or drugs with synergistic or simply additive therapeutic benefit or in can allow increase in antigen load.

The optionally coated mini-beads of the invention may be formulated directly following their manufacture in the ways described above. In an alternative embodiment, it may be desired to impart different properties to the mini-beads and/or to a final solid dosage product. One way of achieving this according to the invention is through granulation eg. to improve the flow of powder mixtures of mini-beads with other components as e.g. described above in relation to binders. Granules of intact or broken mini-beads may be obtained by adding liquids (eg binder or solvent solutions) and effecting a granulating step as described in the prior art. Larger quantities of granulating liquid produce a narrower particle size range and coarser and harder granules, i.e. the proportion of fine granulate particles decreases. The optimal quantity of liquid needed to get a given particle size may be chosen in order to minimise batch-to-batch variations. According to this embodiment, wet granulation is used to improve flow, compressibility, bio-availability, homogeneity, electrostatic properties, and stability of the composition of the invention presented as a solid dosage form. The particle size of the granulate is determined by the quantity and feeding rate of granulating liquid. Wet granulation may be used to improve flow, compressibility, bio-availability, and homogeneity of low dose blends, electrostatic properties of powders, and stability of dosage forms. A wet granulation process according to this embodiment may employ low or high shear mixing devices in which a low viscosity liquid (preferably water) is added to a powder blend containing binder previously dry mixed with the rest of the formulation including mini-beads. Alternative granulation approaches which may be utilized include high-shear, extrusion and conventional wet granulation.

EXAMPLES

The following examples are intended to further illustrate the invention and its preferred embodiments. They are not intended to limit the invention in any manner. Unless otherwise specified, all percentages and ratios in the examples and elsewhere in this specification are by weight.

The beads made or tested in the examples have a diameter of between about 1 mm and about 2 mm.

Example 1

The following components were combined as described: Montanide and Squalene as oils with Labrafil M 1944 CS, Span 85 and Tween 80 as surfactants to form an oil phase with aqueous elements as a w/o emulsion.

Example 1a

Oil 1 was composed of: Squalene (49.5% w/w), Labrafil M 1944 CS (49.5%), Tween 80 (0.5%) and Span 85 (0.5%). Labrafil M 1944 CS is described as oleoyl macrogolglycerides (polyoxylglycerides) having an HLB value of 4 and is reported to be composed largely of triglycerides based on oleic and linoleic acid (C18) and pegylated derivatives. Tween 80 is a registered trade mark for polysorbate 80 (CAS Registry Number 9005-65-6), TWEEN 80 is a polyethylene sorbitol ester, with a calculated molecular weight of 1,310 daltons, assuming 20 ethylene oxide units, 1 sorbitol, and 1 oleic acid as the primary fatty acid. SPAN 85 (CAS Registry Number 26266-58-0) is based on nonionic surfactants (sorbitan esters and ethoxylated sorbitan esters) and has an HLB value of 1.8. SPAN is a registered trademark of Croda International PLC.

Example 1b

Oil 2: Montanide ISA 720 (24%), Squalene (24%), Labrafil M 1944 CS (51%), Tween 80 (0.5%) and Span 85 (0.5%). MONTANIDE ISA 720 is a metabolisable oil adjuvant. It contains mannide oleate in natural metabolisable oil and is a squalene based water-in-oil mannide oleate formulation.

Example 1c

Oil 3 is composed of about 75% Labrafil M 1944 CS, 24.8% Montanide ISA 720, 0.1% Tween 80 and 0.1% Span 85.

Example 1d

Oil 4 is composed of about 67.2% Labrafil M 1944 CS, 24% Montanide ISA 720, 4% Tween 80 and 4.8% Span 85.

Examples 2-6

Using oil 3 (Example 1c) the following uncoated vaccine compositions were manufactured as described in the section above on manufacturing. In the following examples, ovalbumin (OVA) is used as a model antigen as it is known to stimulate an immune response in animals, albeit weak. The endotoxin content is less than 1 EU/mg.

Example 2

Ovalbumin (OVA) was dissolved in NaHCO3/NaOH buffer (pH=9.6) at room temperature and at a concentration of 0.04% by weight, then HPMCP (1.79% by weight), and D-Sorbitol (2.55% by weight) were added. After all the above mentioned components were dissolved, the solution was heated up to 65° C. and gelatin was added at a concentration of 16.91% by weight. The percentages mentioned in this paragraph are % by weight of the total aqueous solution.

After the gelatin completely dissolved, oil 3 was added with stirring to the gelatin solution at a weight ratio of 1:7. The obtained emulsion was then extruded by pipette and cooled/solidified in medium chain triglyceride to form beads which were then extracted for drying.

In the table below the composition of the formulation after drying is given.

| OVA 001/B Dried Beads | mg/g |
|---|---|
| Ovalbumin | 8.03 |
| Labrafil M 1944 CS | 291.65 |
| Montanide ISA 720 | 94.60 |
| Span 85 | 2.07 |
| Tween 80 | 1.99 |
| D-Sorbitol | 71.14 |
| NaHCO3 | 8.33 |
| NaOH | 0.85 |
| HPMCP | 49.79 |
| Gelatin | 471.56 |

Example 3

Poly I:C (polyinosinic:polycytidylic acid) and CpG (cytosine phosphate guanine) were used as adjuvants. They were used as commercially supplied, i.e. as aqueous solution and were incorporated into the oil phase (oil 3) by initially creating a water in oil (w/o) emulsion and thereafter dispersing this emulsion into the aqueous phase containing OVA, D-Sorbitol, HPMCP and gelatin.

The composition of the gelatin solution was the same as that described in Example 2. Gelatin solution and oil phase (containing the adjuvants aqueous solution) were mixed in a 7:1 ratio. Beads were produced according to the technique described in Example 2. The table below gives the composition of the beads on dry basis.

| OVA 002/B Dried Beads | mg/g |
|---|---|
| Ovalbumin | 8.33 |
| Labrafil M 1944 CS | 255.04 |
| Montanide ISA 720 | 82.75 |
| Span 85 | 1.79 |
| Tween 80 | 1.74 |
| CpG | 2.06 |
| Poly I:C | 2.53 |
| NaHCO3 | 8.94 |
| NaOH | 0.92 |
| D-Sorbitol | 76.35 |
| HPMCP | 53.44 |
| Gelatin | 506.12 |

Example 4

AlphaGalCer was used as adjuvant. It was dispersed into the oil 3 at room temperature and at a concentration of 0.1% w/w. The oil phase was then mixed with the aqueous phase (having the same composition described in Example 2) at a 1:7 ratio (w/w). Beads were produced according to the technique described in Example 2.

| OVA 003/B Dried Beads | mg/g |
| --- | --- |
| Ovalbumin | 8.06 |
| alpha GalCer | 0.04 |
| Labrafil M 1944 CS | 291.92 |
| Montanide ISA 720 | 94.70 |
| Span 85 | 2.03 |
| Tween 80 | 1.99 |
| NaHCO3 | 8.33 |
| NaOH | 0.85 |
| D-Sorbitol | 71.09 |
| HPMCP | 49.76 |
| Gelatin | 471.24 |

Example 5

MPLA was used as adjuvant. It was dispersed in the oil 3 at room temperature and at a concentration of 0.3% by weight. The oil phase was then added to the aqueous (1:7 ratio) and the beads were produced as described above.

| OVA 004/B Dried Beads | mg/g |
| --- | --- |
| Ovalbumin | 8.02 |
| MPLA | 1.19 |
| Labrafil M 1944 CS | 291.27 |
| Montanide ISA 720 | 94.50 |
| Span 85 | 2.06 |
| Tween 80 | 1.98 |
| NaHCO3 | 8.32 |
| NaOH | 0.85 |
| D-Sorbitol | 71.06 |
| HPMCP | 49.73 |
| Gelatin | 471.02 |

Example 6

Quil A (*Quillaja saponaria* A) was used as adjuvant. It was dispersed in oil 3 at room temperature and at a concentration of 2% by weight. The oil phase was then added to the aqueous (1:7 ratio) and the beads were produced as described above.

| OVA 005/B Dried Beads | mg/g |
| --- | --- |
| Ovalbumin | 8.56 |
| Quil A | 8.01 |
| Labrafil M 1944 CS | 286.51 |
| Montanide ISA 720 | 92.19 |
| Span 85 | 2.00 |
| Tween 80 | 1.95 |
| NaHCO3 | 8.32 |
| NaOH | 0.85 |
| D-Sorbitol | 71.03 |
| HPMCP | 49.71 |
| Gelatin | 470.86 |

Example 7

In this example, the mini-beads of examples 2-6 were administered to mice (to examine immunogenicity of the model antigen ovalbumin) and to compare the immune responses induced to either OVA alone in solution or with the potent, established mucosal adjuvant cholera toxin (CT).

BALB/c mice were immunized orally on 2 consecutive days with ovalbumin (200 µg/mouse) either alone or with cholera toxin (CT; 10 µg/mouse) in bicarbonate buffer or with 4 mini-beads/mouse per day ovalbumin (OVA) placebo, OVA in Oil3, OVA+MPLA in Oil3, OVA+alphaGalCer in Oil3, OVA+QuilA in Oil3, OVA+CpG+Poly (I:C) in Oil3. All mice were boosted 2.5 weeks later with an identical series of immunizations. 2.5 weeks post the second round of oral immunizations all mice were boosted intraperitoneally (i.p.) with ovalbumin (50 µg/mouse) and alum. One group of mice was immunized i.p. with OVA and alum as a control. OVA-specific IgG antibody responses were determined by ELISA on serum samples recovered immediately prior to the second round of oral immunizations ((a) post first series of oral immunizations), immediately prior to the final boost with OVA and alum i.p. ((b) post second series of oral immunizations) or one week post the final boost i.p. ((c) post i.p. boost with OVA and alum). Results are expressed as individual and mean end-point titres (+S.E.) for three to five mice per group (see FIGS. 1 and 2).

Example 8

BALB/c mice were immunized and OVA-specific IgG antibody titres were determined on serum samples recovered as described as above in Example 7. Results are expressed as IgG end-point titres for individual mice with the mean value for each group of mice represented as a solid line.

Figure 3:
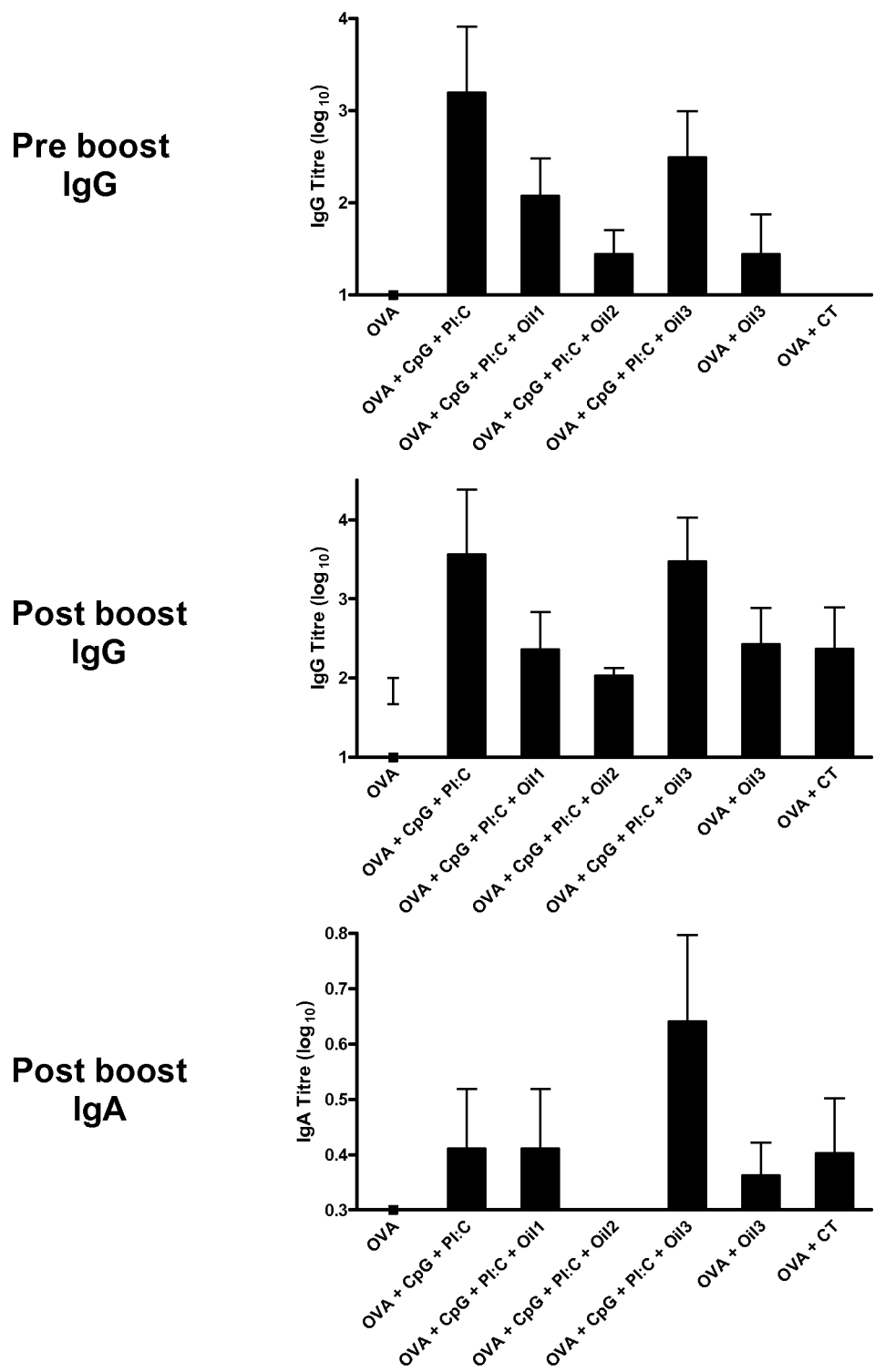
FIG. 3 comprises plots of mean end-point IgG titres of BALB/c mice immunised orally with mini-bead compositions of the invention and with comparative solutions, as described in Example 8.
Figure 4:
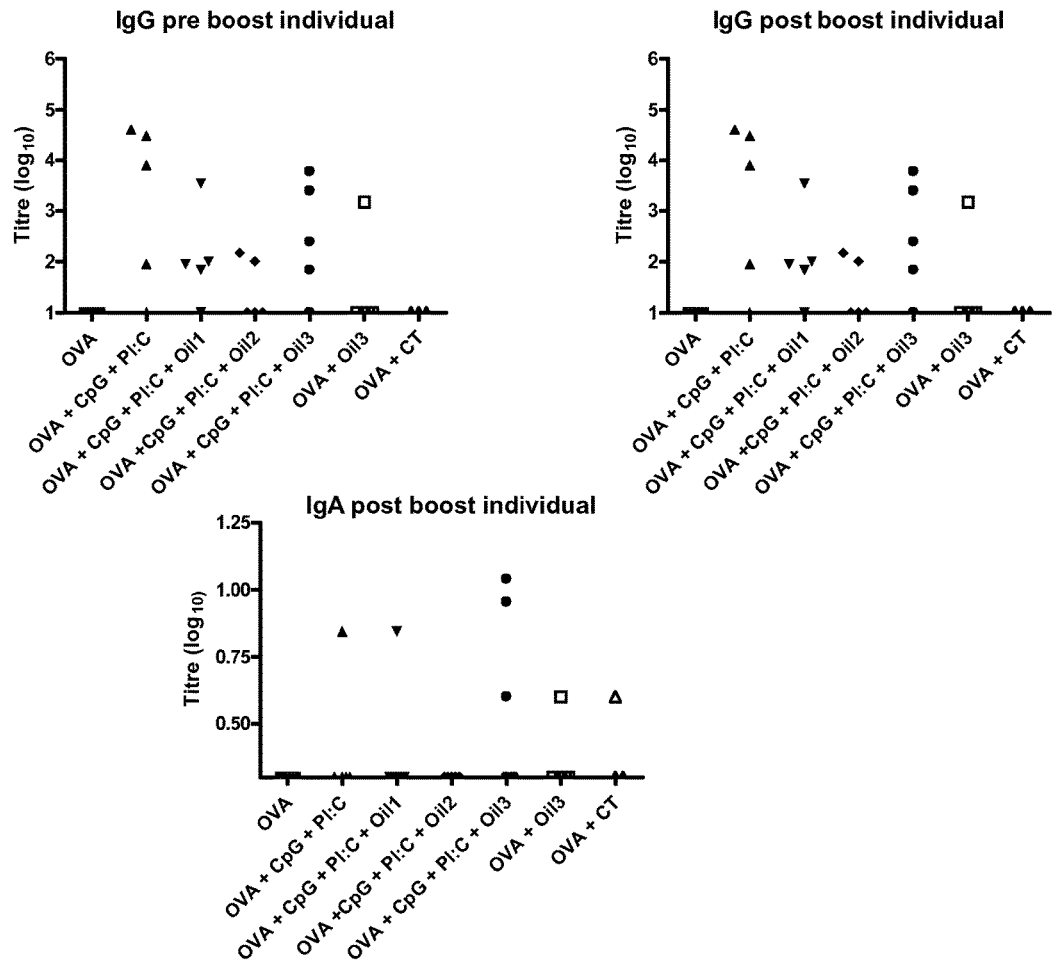
FIG. 4 comprises plots of individual end-point IgG titres of BALB/c mice immunised orally with mini-bead compositions of the invention and with comparative solutions, as described in Example 8.

After just one series of oral immunizations, a slight enhancement of ovalbumin-specific IgG antibodies was seen in the sera of mice immunized with mini-beads containing ovalbumin and Oil3 with either MPLA, alphaGalCer or QuilA as adjuvant (FIGS. 3a and 4a).

After two rounds of oral immunizations, there was strong enhancement of OVA-specific IgG antibodies from all mice immunized orally with mini-beads containing Oil3. In contrast, there was no enhancement of IgG in the sera of mice immunized orally with mini-beads and OVA in placebo, indicating that the presence of Oil3 in the mini-bead formulations induces a strong IgG response (FIGS. 3b and 4b).

The alphaGalCer adjuvant in particular was found to be effective adjuvant in the mini-beads after two rounds of oral immunizations. In contrast, oral immunizations with either ovalbumin alone or with CT in solution gave variable IgG antibody responses. (FIGS. 3b and 4b).

17 days after the second round of oral immunizations, all mice were boosted intraperitoneally (i.p.) with OVA and alum. The strongest anti-ovalbumin IgG antibody responses were seen from mice primed orally with mini-beads containing OVA and Oil3 with alphaGalCer as adjuvant and boosted i.p. All mice immunized with this formulation showed strong IgG antibody responses. Mice immunized orally with mini-beads formulations containing OVA and oil3 with either no adjuvant or MPLA or QuilA as adjuvant and boosted i.p. also had strong IgG titres, although the responses were more variable than those seen from mice primed orally with mini-beads and alphaGalCer (FIGS. 3c and 4c).

Example 9

In the following example the oil phase and the aqueous phase are mixed in a proportion in the range 1:6-10, preferably approximately 1:7 or 1:8 with gentle continuous stirring of the components using a Magnetic Stirrer (manufactured by Stuart). The aqueous phase (gelatine, sorbitol, HPMCP, NaHCO3 and NaOH) was prepared by adding the appropriate quantities of sorbitol, HPMCP, NaHCO3 and NaOH to water, heating to approximately 60-75° C. until in solution and then adding gelatin. The "gelatin solution"

comprised 15-25% (preferably 17-18%) of gelatin; 75%-85% (preferably 77-82%) of water plus from 1-5% (preferably 1.5 to 3%) sorbitol. The gelatin solution was maintained at 60° C.-70° C. to maintain it in a fluid state. The oil phase was made at room temperature by addition to the oils of surfactant (eg Span 85 and/or Tween 80) with stirring. The appropriate amount of ovalbumin (see table below) was added to achieve the target proportion. An emulsion was formed by addition of the oil phase (or w/o emulsion) to the heated aqueous phase (gelatine solution) with stirring for 1 to 2 hours. The resultant emulsion (or w/o/w emulsion) then had the composition of the solidified mini-beads but with water still present. Once the emulsion was formed, the beading step was begun without delay by using a pipette and dropping the fluid emulsion manually into MCT (cooling fluid) maintained in the range 8-12° C. which effected solidification. Beads were then collected in a mesh basket through which the oil was drained and the beads retained, excess oil removed by centrifugation then washed with ethyl acetate then dried. Drying was with the Freund Drum dryer with warm air at between 15° C. and 25° C. Uncoated minibeads with the following composition were made:

| Components | Lower limit (mg/g) | Upper limit (mg/g) |
|---|---|---|
| Ovalbumin | 8.0 | 8.6 |
| Gelatin | 470 | 510 |
| D-Sorbitol | 71 | 76 |
| HPMCP | 49 | 54 |
| NaHCO₃ | 8.0 | 9.0 |
| NaOH | 0.8 | 0.9 |
| Montanide ISA 720 VG | 82 | 95 |
| Labrafil M 1944 CS | 255 | 300 |
| Span 85 | 1.8 | 2.0 |
| Tween 80 | 1.7 | 2.0 |
| CpG | 0 | 2.0 |
| Poly I:C | 0 | 2.5 |
| αGalCer | 0 | 0.04 |
| MPLA | 0 | 1.2 |
| Quil A | 0 | 8.0 |

The preferred formulation containing OVA as model antigen is the following:

| Components | Lower limit (mg/g) | Upper limit (mg/g) |
|---|---|---|
| Ovalbumin | 8.0 | 8.6 |
| Gelatin | 470 | 490 |
| D-Sorbitol | 71 | 73 |
| HPMCP | 49 | 51 |
| NaHCO₃ | 8.0 | 9.0 |
| NaOH | 0.8 | 0.9 |
| Montanide ISA 720 VG | 90 | 95 |
| Labrafil M 1944 CS | 285 | 295 |
| Span 85 | 1.9 | 2.1 |
| Tween 80 | 1.9 | 2.1 |
| αGalCer | 0.04 | 0.61 |

Examples 10-13

These examples were produced in the same way as for Example 9 and the oil 3 as in Example 1c. AlphaGalCer was dissolved in the NaHCO₃/NaOH buffer (pH=9.64) at a temperature of approximately 70° C., and then OVA, D-Sorbitol, HPMCP and gelatin were added. The concentrations used changed slightly for the different examples and will be indicated for each example.

Example 10

The concentrations used for the components of the aqueous phase were the following:

| Components | Concentration (% w/w) |
|---|---|
| Gelatin | 22.97 |
| HPMCP | 2.39 |
| D-Sorbitol | 3.39 |
| aGalCer | 0.19 |
| OVA | 3.91 |

Note: No oil phase was used to produce the beads of this example.

| | | g | mg/g | % |
|---|---|---|---|---|
| OVA 012/B Control | Gelatin | 0.574 | 780.70 | 78.07 |
| | HPMCP | 0.060 | 81.46 | 8.15 |
| | D-Sorbitol | 0.085 | 115.41 | 11.54 |
| | NaOH | 0.001 | 1.36 | 0.14 |
| | NaHCO₃ | 0.005 | 6.79 | 0.68 |
| | OVA | 0.010 | 13.60 | 1.36 |
| | aGalCer | 0.001 | 0.68 | 0.07 |
| | Total | 0.74 | | 100.00 |

Example 11

The concentrations used for the components of the aqueous phase were the following:

| Components | Concentration (% w/w) |
|---|---|
| Gelatin | 22.97 |
| HPMCP | 2.39 |
| D-Sorbitol | 3.39 |
| aGalCer | 0.29 |
| OVA | 3.94 |

The gelatin phase described above and the oil phase (oil 3) were mixed at a ratio of 6.5:1

| | | g | mg/g | % |
|---|---|---|---|---|
| OVA 013/B oil 3 | Montanide ISA 720 | 0.118 | 95.98 | 9.60 |
| | Labrafil M1944CS | 0.367 | 299.53 | 29.95 |
| | Tween 80 | 0.002 | 2.00 | 0.20 |
| | Span 85 | 0.003 | 2.40 | 0.24 |
| | Gelatin | 0.574 | 468.34 | 46.83 |
| | HPMCP | 0.060 | 48.87 | 4.89 |
| | D-Sorbitol | 0.085 | 69.23 | 6.92 |
| | NaOH | 0.001 | 0.81 | 0.08 |
| | NaHCO₃ | 0.005 | 4.07 | 0.41 |
| | OVA | 0.010 | 8.16 | 0.82 |
| | aGalCer | 0.001 | 0.61 | 0.06 |
| | Total | 1.23 | | 100.00 |

Example 12

In this example, the oil phase is referred to as oil MF59. This refers to the MF59 adjuvant known in the literature (see eg. Schultze et al, Vaccine 26 (2008) 3209-3222, the entirety of which is incorporated herein by reference). The squalene used in the Example was purchased from Sigma-Aldrich. In this example, the oil components from the literature adjuvant (which is made in water) were extrapolated to a water-free composition and the resultant composition was as follows:

| | | % |
|---|---|---|
| MF59 oil | Squalene | 81.14 |
| | Tween 80 | 9.43 |
| | Span 85 | 9.43 |

The concentrations used for the components of the aqueous phase were the following:

| Components | Concentration (% w/w) |
|---|---|
| Gelatin | 22.97 |
| HPMCP | 2.39 |
| D-Sorbitol | 3.39 |
| aGalCer | 0.17 |
| OVA | 3.98 |

The oil phase and the aqueous phase were mixed at a ratio of 1:5.6

| | | g | mg/g | % |
|---|---|---|---|---|
| OVA 014/B | Squalene | 0.398 | 324.48 | 32.45 |
| oil MF59 | Tween 80 | 0.046 | 37.71 | 3.77 |
| | Span 85 | 0.046 | 37.71 | 3.77 |
| | Gelatin | 0.574 | 468.34 | 46.83 |
| | HPMCP | 0.060 | 48.87 | 4.89 |
| | D-Sorbitol | 0.085 | 69.23 | 6.92 |
| | NaOH | 0.001 | 0.81 | 0.08 |
| | NaHCO$_3$ | 0.005 | 4.07 | 0.41 |
| | OVA | 0.010 | 8.16 | 0.82 |
| | aGalCer | 0.001 | 0.61 | 0.06 |
| | Total | 1.23 | | 100.00 |

Example 13

In this example a thiol derivative of aGalCer (indicated as aGalCer-S) was used as adjuvant. A 0.1 M NaOH solution was used instead of the NaHCO$_3$/NaOH buffer to prepare the aqueous phase The concentrations used for the components of the aqueous phase were the following:

| Components | Concentration (% w/w) |
|---|---|
| Gelatin | 22.53 |
| HPMCP | 2.38 |
| D-Sorbitol | 3.33 |
| aGalCer-S | 0.19 |
| OVA | 3.95 |

Oil phase (oil 3) and aqueous phase were mixed at a 1:7 ratio

| | | g | mg/g | % |
|---|---|---|---|---|
| OVA 015/B | Montanide ISA 720 | 0.118 | 96.56 | 9.66 |
| oil 3 | Labrafil M1944CS | 0.367 | 301.36 | 30.14 |
| | Tween 80 | 0.002 | 2.01 | 0.20 |
| | Span 85 | 0.003 | 2.41 | 0.24 |
| | Gelatin | 0.566 | 464.82 | 46.48 |

| | | g | mg/g | % |
|---|---|---|---|---|
| | HPMCP | 0.060 | 49.13 | 4.91 |
| | D-Sorbitol | 0.084 | 68.68 | 6.87 |
| | NaOH | 0.007 | 5.92 | 0.59 |
| | OVA | 0.010 | 8.29 | 0.83 |
| | aGalCer-S | 0.001 | 0.82 | 0.08 |
| | Total | 1.22 | | 100.00 |

Examples 14-21

In the following examples CTB (rCTB—recombinant subunit B of cholera toxin), used as antigen/adjuvant, was obtained from SBL Vaccin AB and employed as commercially supplied, i.e. PBS buffer solution at 9 mg/ml.

The preferred formulation using rCTB as antigen is presented in the table below:

| Components | Lower limit (mg/g) | Upper limit (mg/g) |
|---|---|---|
| rCTB | 2.1 | 6.9 |
| Gelatin | 470 | 560 |
| D-Sorbitol | 46 | 58 |
| Montanide ISA 720 VG | 85 | 100 |
| Labrafil M 1944 CS | 230 | 250 |
| Span 85 | 10 | 18 |
| Tween 80 | 30 | 45 |
| αGalCer | 0.8 | 1.9 |

Example 14

As per Example 13, a 0.1M NaOH solution was used as aqueous phase. The concentrations used for the components of the aqueous phase were the following:

| Components | Concentration (% w/w) |
|---|---|
| Gelatin | 22.52 |
| HPMCP | 2.39 |
| D-Sorbitol | 3.33 |
| aGalCer | 0.17 |

The aqueous phase and the oil phase (oil 3) were mixed at a 1:7 ratio, then the 0.211 ml of the rCTB solution, corresponding to 1.9 mg of solid rCTB, were added and the resulting mixture was further stirred and then beads were produced according to the technique previously described.

| | | g | mg/g | % |
|---|---|---|---|---|
| CTB 001/B | Montanide ISA 720 | 0.119 | 98.07 | 9.81 |
| oil 3 | Labrafil M1944CS | 0.371 | 306.06 | 30.61 |
| | Tween 80 | 0.002 | 2.04 | 0.20 |
| | Span 85 | 0.003 | 2.45 | 0.25 |
| | Gelatin | 0.564 | 465.24 | 46.52 |
| | HPMCP | 0.060 | 49.18 | 4.92 |
| | D-Sorbitol | 0.083 | 68.74 | 6.87 |
| | NaOH | 0.007 | 5.93 | 0.59 |
| | CTB | 0.0019 | 1.57 | 0.16 |
| | aGalCer | 0.001 | 0.72 | 0.07 |
| | Total | 1.21 | | 100.00 |

Example 15

This example was prepared as for example 14, with the only difference being the use of alphaGalCer-S instead of alphaGalCer as adjuvant.

| | | g | mg/g | % |
|---|---|---|---|---|
| CTB 002/B | Montanide ISA 720 | 0.119 | 98.01 | 9.80 |
| oil 3 | Labrafil M1944CS | 0.372 | 305.87 | 30.59 |
| | Tween 80 | 0.002 | 2.04 | 0.20 |
| | Span 85 | 0.003 | 2.45 | 0.25 |
| | Gelatin | 0.565 | 465.37 | 46.54 |
| | HPMCP | 0.060 | 49.19 | 4.92 |
| | D-Sorbitol | 0.084 | 68.76 | 6.88 |
| | NaOH | 0.007 | 5.93 | 0.59 |
| | CTB | 0.0019 | 1.56 | 0.16 |
| | aGalCer-S | 0.001 | 0.82 | 0.08 |
| | Total | 1.21 | | 100 |

Example 16

In this example oil 4 (the composition of which is described in example 1d) was used as oil phase. In the aqueous phase a 0.1 M NaOH solution containing 0.5% Tween 80 as surfactant was used. AlphaGalCer was used as adjuvant and dissolved in the aqueous phase at approximately 70° C. and at a concentration of 0.04%, then HPMCP (1.71%), D-Sorbitol (1.7%) and gelatin (17.03%) were added and dissolved keeping the same temperature. Oil phase and aqueous phase were mixed at a 1:7 ratio and finally the rCTB solution (0.300 ml, corresponding to 2.7 mg) was added. The beads were then produced according to the technique previously described.

| | | g | mg/g | % |
|---|---|---|---|---|
| CTB 003/B | Montanide ISA 720 | 0.123 | 98.67 | 9.87 |
| oil 4 | Labrafil M1944CS | 0.336 | 268.09 | 26.8 |
| | Tween 80 | 0.042 | 33.56 | 3.36 |
| | Span 85 | 0.019 | 15.53 | 1.55 |
| | Gelatin | 0.596 | 476.35 | 47.64 |
| | HPMCP | 0.060 | 48.11 | 4.81 |
| | D-Sorbitol | 0.061 | 47.95 | 4.79 |
| | NaOH | 0.011 | 8.79 | 0.88 |
| | CTB | 0.0027 | 2.16 | 0.22 |
| | aGalCer | 0.001 | 0.80 | 0.08 |
| | Total | 1.25 | | 100 |

Example 17

This example was prepared as Example 16. The only difference is the concentration of alphaGalCer, which was doubled.

| | | g | mg/g | % |
|---|---|---|---|---|
| CTB 004/B | Montanide ISA 720 | 0.123 | 98.43 | 9.84 |
| oil 4 | Labrafil M1944CS | 0.335 | 267.42 | 26.74 |
| | Tween 80 | 0.042 | 33.65 | 3.37 |
| | Span 85 | 0.019 | 15.49 | 1.55 |
| | Gelatin | 0.595 | 474.83 | 47.48 |
| | HPMCP | 0.060 | 48.11 | 4.81 |
| | D-Sorbitol | 0.062 | 49.55 | 4.96 |
| | NaOH | 0.011 | 8.78 | 0.88 |
| | CTB | 0.003 | 2.15 | 0.22 |
| | aGalCer | 0.002 | 1.6 | 0.16 |
| | Total | 1.25 | | 100.00 |

Example 18

In this example the aqueous phase had the same composition as described in example 16. No oil phase was used

| | | g | mg/g | % |
|---|---|---|---|---|
| CTB 005/B | Tween 80 | 0.019 | 21.09 | 2.11 |
| No oil phase | Gelatin | 0.754 | 828.45 | 82.85 |
| | HPMCP | 0.060 | 65.9 | 6.59 |
| | D-Sorbitol | 0.061 | 66.34 | 6.63 |
| | NaOH | 0.014 | 15.27 | 1.52 |
| | CTB | 0.002 | 2.2 | 0.22 |
| | aGalCer | 0.0007 | 0.77 | 0.08 |
| | Total | 0.91 | | 100.00 |

Example 19

This example was prepared as described in Examples 17 and 18, the only difference being that no alphaGalCer was used. The concentrations of the components of the aqueous phase were the following:

| Components | % w/w |
|---|---|
| Gelatin | 17.12 |
| D-Sorbitol | 1.72 |
| HPMCP | 1.72 |
| Tween 80 | 0.43 |
| NaOH | 0.32 |

Oil phase (oil 4) and aqueous phase were mixed at a 1:7 ratio. 0.300 ml of rCTB solution were finally added.

| | | g | mg/g | % |
|---|---|---|---|---|
| CTB 006/B | Montanide ISA 720 | 0.120 | 96.48 | 9.65 |
| oil 4 | Labrafil M1944CS | 0.334 | 267.9 | 26.79 |
| | Tween 80 | 0.040 | 32.03 | 3.2 |
| | Span 85 | 0.022 | 17.32 | 1.73 |
| | Gelatin | 0.596 | 478.87 | 47.88 |
| | HPMCP | 0.060 | 48.2 | 4.82 |
| | D-Sorbitol | 0.060 | 48.2 | 4.82 |
| | NaOH | 0.011 | 8.84 | 0.88 |
| | CTB | 0.0027 | 2.17 | 0.22 |
| | Total | 1.24 | | 100 |

Example 20

In this example a PBS buffer containing 0.5% Tween 80 was used as aqueous phase. AlphaGalCer (0.06% w/w) was dissolved at 70° C., then D-Sorbitol (1.74%) and gelatin (17.51%) were added. Oil phase (oil 4) was added to the above aqueous phase at a ratio of 1:9. Finally 0.300 ml of rCTB solution were added to the above mixture and beads were produced.

|  |  | g | mg/g | % |
| --- | --- | --- | --- | --- |
| CTB 008/B oil 4 | Montanide ISA 720 | 0.095 | 87.5 | 8.75 |
|  | Labrafil M1944CS | 0.256 | 236.83 | 23.68 |
|  | Tween 80 | 0.037 | 34.28 | 3.43 |
|  | Span 85 | 0.015 | 13.73 | 1.37 |
|  | Gelatin | 0.604 | 557.71 | 55.77 |
|  | D-Sorbitol | 0.060 | 55.45 | 5.55 |
|  | Salts (from PBS buffer) | 0.011 | 10.17 | 1.02 |
|  | CTB | 0.0027 | 2.5 | 0.25 |
|  | aGalCer | 0.002 | 1.85 | 0.19 |
|  | Total | 1.08 |  | 100 |

The above beads were then coated with Eudragit L30-D 55 to achieve a 5.5% weight gain.

Example 21

In this example purified water was used as aqueous phase, which contained Tween 80 (0.52%), D-Sorbitol (1.67%) and gelatin (17.25%). The oil phase was represented by oil 4, where alphaGalCer (0.51%) and freeze-dried rCTB (1.83%) were dispersed at room temperature. Oil phase and aqueous phase were then mixed at a ratio of 1:9.

|  |  | g | mg/g | % |
| --- | --- | --- | --- | --- |
| CTB 009/B oil 4 | Montanide ISA 720 | 0.096 | 85.29 | 8.53 |
|  | Labrafil M1944CS | 0.262 | 232.05 | 23.21 |
|  | Tween 80 | 0.047 | 41.6 | 4.16 |
|  | Span 85 | 0.020 | 17.89 | 1.79 |
|  | Gelatin | 0.63 | 560.47 | 56.05 |
|  | D-Sorbitol | 0.061 | 54.11 | 5.41 |
|  | CTB | 0.0076 | 6.73 | 0.67 |
|  | aGalCer | 0.002 | 1.86 | 0.19 |
|  | Total | 1.12 |  | 100 |

As in the previous example, beads were then coated with Eudragit L 30-D 55. The weight gain achieved was 6.3%.

Example 22

This example demonstrates by a murine intestinal loop assay using cholera toxin that formulations of the invention are effective in providing immunological protection against challenge by an antigen. The example uses a cholera toxin challenge as described by Tokuhara D et al., (2010) *Proc. Natl. Acad. Sci. USA* 107: 8794-8799.

Mice were immunised orally with various cholera toxin B subunit (CTB) formulations. In certain formulations, α-galactosylceramide, also known as alphaGalCer, is used as an adjuvant. The formulations tested were:
(i) PBS
(ii) CTB in solution alone
(iii) CTB in solution with cholera toxin (the most powerful mucosal adjuvant)
(iv) CTB in solution with alphaGalCer
(v) CTB in oil 3 without alphaGalCer in a bead formulation
(vi) CTB in oil 3 with alphaGalCer in an NaOH-containing bead format
(vii) CTB in oil 3 in with alphaGalCer in a bead formulation where NaOH is not used.

The formulation (v) is CTB 006/B (Example 19). Formulation (vi) is CTB 004/B (Example 17). Formulation (vii) is CTB 009/B (Example 21).

Figure 5:
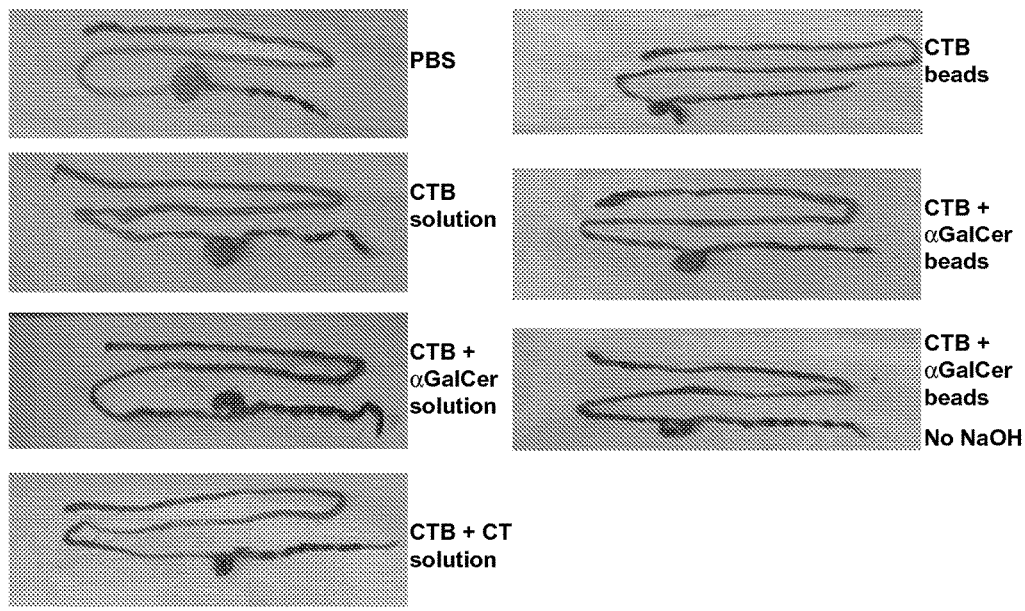
FIG. 5 comprises photographs of digestive tracts of mice which underwent an intestinal loop assay.
Figure 6:
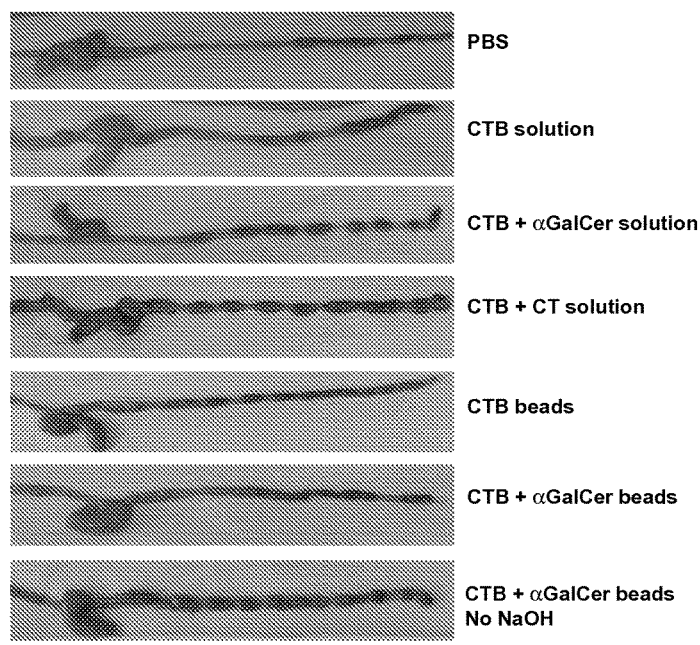
FIG. 6 comprises photographs of the large intestine of mice which underwent an intestinal loop assay.

BALB/c mice were immunized orally on 2 consecutive days at weeks 0, 2 and 4 with CTB (20 µg/mouse) alone or mixed with cholera toxin (CT; 10 µg/mouse) or alphaGalCer (15 µg/mouse) in solution or with the formulations indicated above. One week after the final vaccination, 20 µg of cholera toxin was administered by oral gavage to all mice. After 12 hours, mice were sacrificed and the digestive tracts were removed. The removed digestive tracts and, respectively, the removed large intestine are shown in FIGS. 5 and 6. FIG. 5 shows fluid accumulation, particularly in the caecum of the mice. Unless mice are effectively vaccinated the delivery of cholera toxin leads to significant fluid accumulation in the intestine (a surrogate for diarrhea in humans). In FIG. 5, it can be seen that in mice immunized with PBS or CTB only, significant fluid accumulation occurred. In contrast, mice immunised with formulations of the invention had less fluid accumulation. Especially mice immunised with beads containing CTB+GalCer in Oil3 formulated without NaOH, there was considerably less fluid accumulation; this effect was comparable to the effects seen using the positive control adjuvant, cholera toxin. FIG. 6 shows the large intestine of the same mice. Normal pellet formation is indicative of protection whereas in groups (i) and (ii) (PBS, CTB) it can been seen that there is poor pellet formation, again indicative of diarrhea. In FIG. 6 it can also be seen that mice immunised with bead formulations containing CTB+GalCer in Oil3 formulated without NaOH had normal pellet formation in the large intestine indicative of protection against cholera toxin.

The invention also relates to the subject matter of the following clauses:

1. A pharmaceutical composition comprising a water-soluble polymer matrix in which are dispersed droplets of oil, the composition comprising at least one active principle for immune modulation selected from an adjuvant, an antigen or a combination thereof.

2. A composition according to clause 1, wherein the immune modulation is vaccination, tolerisation or immunotherapy.

3. A composition according to clause 2 wherein the active principle is included in at least some of the oil droplets.

4. A composition according to any preceding clause wherein the oil droplets are released as the matrix containing them dissolves in an aqueous medium.

5. A composition according to any preceding clause wherein the composition is for oral administration.

6. A composition according to any preceding clause wherein the composition of the invention comprises at least one antigen and at least one adjuvant.

7. An orally administrable composition according to any preceding clause for intestinal/colonic mucosal delivery and/or for immunomodulation e.g. the induction of oral tolerance.

8. A composition according to any preceding clause wherein release of the active principle(s) is along the entire intestinal and colonic/rectal tract or to pre-specified sites along same.

9. A composition according to any preceding clause wherein the composition bears a coat such that the rate and manner of dissolution is modified.

10. A composition according to any preceding clause which further includes a retardant/protectant e.g. HPMC derivatives.

11. A composition according to any preceding clause which comprises a plurality of optionally coated mini-beads of a water-soluble polymer matrix which contains oil droplets wherein the at least one active principle comprises at least one vaccine active principle.

12. A composition according to any preceding clause wherein the composition comprises a plurality of mini-beads of dried oil-in-water emulsion wherein the composition comprises at least one vaccine active principle.

13. A composition according to any preceding clause which comprises a plurality of optionally coated mini-beads of dried oil-in-water emulsion, wherein at least some of the mini-beads (eg a first population) comprise an active principle (or more than one) and optionally other beads (eg a second population) which comprise an active principle (or more than one) or one population may be free of active principles 14. A composition according to any preceding clause wherein the composition includes a component to protect the at least one active principle from exposure to gastric fluid e.g. a polymer which is water-soluble or substantially water-soluble only above a certain pH such as derivatives of hydroxypropyl methylcellulose (HPMC).

15. A composition according to any preceding clause wherein the composition comprises one or more surfactants, preferably non-ionic surfactants.

16. A composition according to any preceding clause wherein the composition has a polymeric coating e.g. of a polymer which degrades in the presence of bacterial enzymes present in the colon.

17. A composition according to the preceding clause wherein the composition comprises a pore-former with a pH-independent polymer.

18. A composition according to any preceding clause wherein the composition comprises one or more agents to enhance adsorption of vaccine antigen onto, and absorption by, mucosal surfaces and/or the underlying mucosal lymphoid tissue, M-cells, Peyer's patches or other immune relevant cells or cell systems.

19. A composition according to any preceding clause wherein the composition is in the form of a suppository, a pessary, a pill, a tablet, a paste or a fluid.

20. A vaccine delivery composition that adsorbs the vaccine onto a mucosal surface of a mammal, and optionally, following absorption of some or all of the components of the vaccine composition, that brings the vaccine into contact with mucosal-associated lymphoid tissue (MALT).

21. A method for the treatment or prevention of a gastro-intestinal condition exacerbated or caused directly or indirectly by an infectious agent, comprising administering the composition according to any preceding clause to an animal e.g. orally.

22. A method of boosting immune response comprising orally administering the vaccine composition according to of clauses 1 to 20 to an animal having received such priming vaccination non-orally.

23. A method of making the composition according to any of clauses 1 to 20 in which a liquid aqueous external phase in which is dispersed oil droplets undergoes solidification e.g. by cross-linking, cooling or heating.

24. A method of vaccination comprising bringing the composition of any of clauses 1 to 20 into contact with a mucosal surface, such as oral cavity, gut, nasal, rectal, or vaginal surfaces.

25. A method of vaccination comprising administering the composition according to any preceding clause as part of feed or drink to animals or introduced into the water in which fish reproduce, eat or otherwise dwell.

26. A method of vaccinating or inducing an immune response in an animal e.g. fish or mammal and/or one or more of the diseases described elsewhere herein comprising administering to the animal the composition according to any of clauses 1 to 20.

27. A method for preparing an immune modulating (eg vaccine) composition comprising mixing an aqueous solution of a water-soluble polymer matrix with an oil-based liquid to form a water-in-oil emulsion and then causing or allowing the resultant suspension to solidify into one or more shaped elements e.g. beads.

28. A vaccine delivery composition that adsorbs the vaccine onto a mucosal surface of a mammal, and optionally, following absorption of some or all of the components of the vaccine composition, that brings the vaccine into contact with mucosal-associated lymphoid tissue (MALT).

29. Oral administration of a vaccine against a gut pathogen comprising presentation or delivery of the vaccine to the gut-associated lymphoid tissue (GALT).

30. Oral administration of a vaccine against an upper respiratory pathogen comprising presentation or delivery of the vaccine to the mucosal-associated lymphoid tissue in the oral cavity or nasal passages.

The invention claimed is:

1. A pharmaceutical composition in the form of a seamless mini-bead comprising a water-soluble polymer matrix, wherein the water soluble polymer matrix provides a substantially solid phase in which are dispersed droplets of oil comprising an ester of polyethylene glycol and a hydrocarbon oil, the composition comprising at least one adjuvant and at least one antigen and at least one of the at least one adjuvant and the at least one antigen being included in at least some of the oil droplets, wherein the adjuvant is a ceramide and the composition is in a form for oral administration.

2. The composition of claim 1 wherein the mini-bead has a diameter of from 0.5 mm to 5 mm.

3. A population of minibeads consisting essentially of minibeads of claim 2.

4. A product comprising a first population of minibeads comprising a water-soluble polymer matrix in which are dispersed droplets of oil and a second population of minibeads comprising a water-soluble polymer matrix in which are dispersed droplets of oil, wherein the first and second populations of minibeads are different and at least the minibeads of the first population are according to claim 2.

5. A composition according to claim 1 wherein the composition is in the form of a plurality of mini-beads having a diameter of from 0.5 mm to 5 mm, the plurality of minibeads forming a product selected from a capsule, a suppository, a pessary, a sachet, a pill, a tablet, a paste or a fluid.

6. A composition according to claim 1 which is a dried oil-in-water emulsion.

7. A composition according to claim 1 which is adapted for oral administration and for release of the oil droplets in the intestine.

8. A composition according to claim 1 wherein the composition comprises one or more surfactants, optionally selected from non-ionic surfactants.

9. A composition according to claim 8 wherein at least a portion of the one or more surfactants and optionally the whole surfactant content of the composition is in the oil droplets.

10. A composition according to claim 1 wherein the composition comprises one or more agents to enhance adsorption of vaccine antigen onto, and absorption by, mucosal surfaces and/or the underlying mucosal lymphoid tissue, M-cells, Peyer's patches or other immune relevant cells or cell systems.

11. A composition according claim 1 wherein the oil comprises macrogolglyceride and hydrocarbon oil together with one or more surfactants.

12. A composition according to claim 1 wherein the droplets of oil comprise ester of polyethylene glycol and/or fatty acid ester.

13. A composition according to claim 12 wherein the fatty acid ester is the ester of a long chain $C_{12}$-$C_{24}$ fatty acid.

14. A composition according to claim 12 wherein the droplets of oil comprise fatty acid macrogolglycerides which are mixtures of fatty acid monoesters, diesters and triesters of glycerol and fatty acid monoesters and diesters of polyethylene glycol.

15. A composition according to claim 11 wherein the fatty acid macrogolglycerides are selected from oleoyl macrogolglycerides or linoeoyl macrogolglycerides.

16. A composition according to claim 1 wherein the adjuvant is α-galactosylceramide.

17. A composition according to claim 1 wherein the antigen is an antigenic substance selected from a killed microorganism or a modified-live microorganism.

18. A composition according to claim 17 wherein the antigenic substance is derived or based on an infectious agent selected from: *Helicobacter pylori, Vibrio cholerae*, enterotoxigenic *Escherichia coli* (ETEC), *Shigella* spp., *Clostridium difficile*, rotaviruses and calici viruses; causative agents of respiratory infections including those caused by *Mycoplasma pneumoniae*, influenza virus, and respiratory syncytial virus; causative agents of sexually transmitted genital infections including those caused by HIV, *Chlamydia trachomatis, Neisseria gonorrhoeae* and herpes simplex virus; *Streptococcus* spp; *Staphylococcus* spp e.g. *S. aureus*; or the poliomyelitis virus (polio).

19. A composition according to claim 1 wherein the water soluble polymer is one or more of those selected from gelatin, agar, a polyethylene glycol, starch, casein, chitosan, soya bean protein, safflower protein, alginates, gellan gum, carrageenan, xanthan gum, phthalated gelatine, succinated gelatine, cellulosephthalate-acetate, oleoresin, polyvinylacetate, hydroxypropyl methyl cellulose, polymerisates of acrylic or methacrylic esters and polyvinylacetate-phthalate or any derivative thereof.

20. A composition according claim 19 wherein the water soluble polymer is selected from gelatin, agar and carrageenan, or is a combination of two or all three thereof.

21. A composition according to claim 19 wherein the water soluble polymer is gelatin.

22. A composition according to claim 1 wherein the water-soluble polymer matrix comprises gelatin and a plasticizer or softener.

23. A composition according to claim 22 wherein the water-soluble polymer matrix comprises gelatin and a plasticizer selected from glycerin, D-sorbitol, sorbitol BP or an aqueous solution of D-sorbitol and sorbitans.

24. A composition according to claim 1 wherein the mini-bead bears a coat to provide controlled or targeted release of the oil droplets.

25. A composition according to claim 1 comprising one or more coatings on the matrix wherein the coating is a polymeric coating, an enteric coating or wherein both polymeric and enteric coatings are present.

26. A composition according to claim 24, wherein the coating comprises a pore-former with a pH-independent polymer.

27. A composition according to claim 1 wherein the mini-bead has a polymeric coating which degrades in the presence of bacterial enzymes present in the colon.

28. A composition according to claim 2 wherein the mini-bead has one or more coatings on the matrix and is selected from:
a) mini-beads which have a polymeric coating
b) mini-beads which include HPMC;
c) mini-beads which bear a coat in order to control release of active principle from the composition, the coat comprising one or more substances of a polymeric nature, the polymeric coating material comprising a methacrylic acid co-polymer, ammonio methacrylate co-polymer, or a mixtures thereof;
d) mini-beads where hydroxypropyl methylcellulose phthalate (HPMCP) is used for coating; or
e) mini-beads which have a coating comprising a combination of ethylcellulose and a polysaccharide susceptible of degradation by a bacterial enzyme normally found in the colon.

29. A mini-bead according to claim 2 wherein:
a) the water soluble polymer is one or more of those selected from gelatin, agar, a polyethylene glycol, starch, casein, chitosan, soya bean protein, safflower protein, alginates, gellan gum, carrageenan, xanthan gum, phthalated gelatine, succinated gelatine, cellulosephthalate-acetate, oleoresin, polyvinylacetate, hydroxypropyl methyl cellulose, polymerisates of acrylic or methacrylic esters and polyvinylacetate-phthalate or any derivative thereof;
b) the droplets of oil comprise esters of polyethylene glycols and/or fatty acid esters and optionally comprise polyethylene glycols, wherein the fatty acid ester is the ester of a long chain $C_{12}$-$C_{24}$ fatty acid; and
c) the mini-bead comprises one or more coatings on the matrix wherein the coating is a polymeric coating, an enteric coating or wherein both polymeric and enteric coatings are present.

30. A mini-bead according to claim 29 wherein the adjuvant is α-galactosylceramide.

31. A mini-bead composition according to claim 29 wherein the antigenic substance comprises a killed microorganism or a modified-live microorganism.

32. A mini-bead according to claim 29 wherein the antigen is an antigenic substance derived or based on an infectious agent selected from: *Helicobacter pylori, Vibrio cholerae*, enterotoxigenic *Escherichia coli* (ETEC), *Shigella* spp., *Clostridium difficile*, rotaviruses and calici viruses; causative agents of respiratory infections including those caused by *Mycoplasma pneumoniae*, influenza virus, and respiratory syncytial virus; causative agents of sexually transmitted genital infections including those caused by HIV, *Chlamydia trachomatis, Neisseria gonorrhoeae* and herpes simplex virus; *Streptococcus* spp; *Staphylococcus* spp e.g. *S. aureus*; or the poliomyelitis virus (polio).

33. A mini-bead according to claim 29 wherein the coating on the minibead comprises one or more coatings selected from:
a) a polymeric coating;
b) a coat in order to control release of active principle from the composition, the coat comprising one or more substances of a polymeric nature, the polymeric coating material comprising a methacrylic acid co-polymer, ammonio methacrylate co-polymer, or a mixtures thereof;
c) a hydroxypropyl methylcellulose phthalate (HPMCP) coating; or
d) a coating comprising a combination of ethylcellulose and a polysaccharide susceptible of degradation by a bacterial enzyme normally found in the colon.

34. A pharmaceutical composition in the form of a seamless mini-bead comprising a water-soluble polymer matrix, wherein the water soluble polymer matrix provides a substantially solid phase in which are dispersed droplets of oil, the composition comprising an antigenic substance and an adjuvant; wherein the antigenic substance comprises a killed microorganism or a modified-live microorganism; the adjuvant is a ceramide; and wherein the droplets of oil comprise esters of polyethylene glycols and/or fatty acid esters and the composition is in a form for oral administration.

35. A composition according to claim 34 wherein the droplets of oil comprise esters of polyethylene glycols.

36. A composition according to claim 34 which is a dried oil-in-water emulsion.

37. A composition according to claim 34 wherein the droplets of oil comprise fatty acid macrogolglycerides which are mixtures of fatty acid monoesters, diesters and triesters of glycerol and fatty acid monoesters and diesters of polyethylene glycol; for examples oleoyl macrogolglycerides and linoeoyl macrogolglycerides.

38. A composition according to claim 34 wherein the droplets of oil comprise polyethylene glycols.

39. A composition according to claim 34 wherein the fatty acid ester is the ester of a long chain $C_{12}$-$C_{24}$ fatty acid.

40. A composition according to claim 34 wherein the adjuvant is α-galactosylceramide.

41. A composition according to claim 34 wherein the antigenic substance is derived or based on an infectious agent selected from: *Helicobacter pylori, Vibrio cholerae*, enterotoxigenic *Escherichia coli* (ETEC), *Shigella* spp., *Clostridium difficile*, rotaviruses and calici viruses; causative agents of respiratory infections including those caused by *Mycoplasma pneumoniae*, influenza virus, and respiratory syncytial virus; causative agents of sexually transmitted genital infections including those caused by HIV, *Chlamydia trachomatis, Neisseria gonorrhoeae* and herpes simplex virus; *Streptococcus* spp; *Staphylococcus* spp e.g. *S. aureus*; or the poliomyelitis virus (polio).

42. A composition according to claim 34 wherein the water soluble polymer is one or more of those selected from gelatin, agar, a polyethylene glycol, starch, casein, chitosan, soya bean protein, safflower protein, alginates, gellan gum, carrageenan, xanthan gum, phthalated gelatine, succinated gelatine, cellulosephthalate-acetate, oleoresin, polyvinylacetate, hydroxypropyl methyl cellulose, polymerisates of acrylic or methacrylic esters and polyvinylacetate-phthalate or any derivative thereof.

43. A composition according claim 42 wherein the water soluble polymer is selected from gelatin, agar and carrageenan, or is a combination of two or all three thereof.

44. A composition according to claim 42 wherein the water soluble polymer is gelatin.

45. A composition according to claim 34 claim which is in the form of a mini-bead wherein the mini-bead has a diameter of from 0.5 mm to 5 mm.

46. A composition according to claim 45 wherein the mini-bead has one or more coatings on the matrix and is selected from:
  a) mini-beads which have a polymeric coating;
  b) mini-beads which include HPMC;
  c) mini-beads which bear a coat in order to control release of active principle from the composition, the coat comprising one or more substances of a polymeric nature, the polymeric coating material comprising a methacrylic acid co-polymer, ammonio methacrylate co-polymer, or a mixtures thereof;
  d) mini-beads where hydroxypropyl methylcellulose phthalate (HPMCP) is used for coating; or
  e) mini-beads which have a coating comprising a combination of ethylcellulose and a polysaccharide susceptible of degradation by a bacterial enzyme normally found in the colon.

47. A composition according to claim 34 wherein the mini-bead has a diameter of from 0.5 mm to 5 mm; and wherein
  the droplets of oil comprise esters of polyethylene glycols;
  the water soluble polymer is selected from gelatin, agar and carrageenan, or is a combination of two or all three thereof; and optionally
  the composition bears a coat to provide controlled or targeted release of the oil droplets.

48. A composition according to claim 1 wherein the adjuvant is a ceramide which stimulates natural killer T (NKT) cells.

49. A composition according to claim 1 wherein the adjuvant is a ceramide selected from an agelasphin, α-galactosylceramide or a thiolated derivative of α-galactosylceramide in which the glycosidic oxygen atom has been replaced by a sulphur atom, or a racemate, enantiomer or diastereoisomer thereof.

50. A composition according to claim 1 wherein the droplets of oil comprise mono- or di-esters of polyethylene glycols.

51. A composition according to claim 28 wherein the mini-bead comprises a polymeric coating and wherein the minibead releases the antigen and adjuvant substantially in the colon.

52. A composition according to claim 28 wherein the mini-bead comprises a polymeric coating and wherein the minibead releases the antigen and adjuvant substantially in the intestine.

53. A composition according to claim 28 wherein the coating is a polymeric coating selected from a polymeric coating which degrades in the presence of bacterial enzymes present in the colon and a polymeric coating which comprises a pore-former.

54. A composition according to claim 28 wherein the coating comprises a combination of ethylcellulose and a polysaccharide selected from chondroitin sulphate, pectin, dextran, guar gum, amylase, chitosan or a lectin.

55. A composition according to claim 28 wherein the coating comprises a combination of ethylcellulose and pectin.

56. A pharmaceutical composition in the form of a seamless mini-bead comprising a water-soluble polymer matrix, wherein the water soluble polymer matrix provides a substantially solid phase in which are dispersed droplets of oil, the composition comprising an antigenic substance and an adjuvant; wherein the antigenic substance comprises a killed microorganism or a modified-live microorganism; the adjuvant is α-galactosylceramide; and wherein the droplets of oil comprise mono- or di-esters of polyethylene glycols and the composition is in a form for oral administration.

57. A composition according to claim 56 which is in the form of a mini-bead wherein the mini-bead has a diameter of from 0.5 mm to 5 mm.

58. A composition according to claim 56 wherein the mini-bead has one or more coatings on the matrix and is selected from:
  a) mini-beads which have a polymeric coating
  b) mini-beads which include HPMC;

c) mini-beads which bear a coat in order to control release of active principle from the composition, the coat comprising one or more substances of a polymeric nature, the polymeric coating material comprising a methacrylic acid co-polymer, ammonio methacrylate co-polymer, or a mixtures thereof;

d) mini-beads where hydroxypropyl methylcellulose phthalate (HPMCP) is used for coating; or e) mini-beads which have a coating comprising a combination of ethylcellulose and a polysaccharide susceptible of degradation by a bacterial enzyme normally found in the colon.

59. A composition according to claim 1, wherein the oil comprises a water in oil emulsion.

60. A composition according to claim 59, wherein the water-in-oil emulsion is a 30:70 aqueous to oil based on volume water-in-squalene oil emulsion which also contains mannide monooleate emulsifier.

61. A composition according claim 11 wherein the macrogolglyceride is an oleoyl macrogol glyceride and the hydrocarbon oil is squalene.

62. A composition according to claim 17 wherein the antigenic substance is derived or based on an infectious agent selected from: *Helicobacter pylori, Vibrio cholerae*, enterotoxigenic *Escherichia coli* (ETEC), *Shigella* spp., *Clostridium difficile*, rotaviruses and calici viruses; causative agents of sexually transmitted genital infections including those caused by HIV, *Chlamydia trachomatis, Neisseria gonorrhoeae* and herpes simplex virus; *Streptococcus* spp; *Staphylococcus* spp e.g. *S. aureus*; or the poliomyelitis virus (polio).

63. A composition according to claim 17 wherein the antigenic substance is derived or based on an infectious agent selected from: *Helicobacter pylori, Vibrio cholerae*, enterotoxigenic *Escherichia coli* (ETEC), *Shigella* spp., *Clostridium difficile*, rotaviruses and calici viruses; *Streptococcus* spp; *Staphylococcus* spp e.g. *S. aureus*; or the poliomyelitis virus (polio).

64. A composition according to claim 17 wherein the composition comprises a coating which comprises a pH-independent polymer to release the antigen and the adjuvant in the colon and the antigenic substance is derived or based on an infectious agent selected from: causative agents of sexually transmitted genital infections including those caused by HIV, *Chlamydia trachomatis, Neisseria gonorrhoeae* and herpes simplex virus.

* * * * *